US008580941B2

(12) United States Patent
Lareyre et al.

(10) Patent No.: US 8,580,941 B2
(45) Date of Patent: Nov. 12, 2013

(54) EPIDIDYMAL LIPOCALIN GENE AND USES THEREOF

(75) Inventors: Jean-Jacques Lareyre, Rennes Cedex (FR); Marie-Claire Orgebin-Crist, Nashville, TN (US); Robert J. Matusik, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 1242 days.

(21) Appl. No.: 11/890,842

(22) Filed: Aug. 8, 2007

(65) Prior Publication Data

US 2009/0118210 A1 May 7, 2009

Related U.S. Application Data

(62) Division of application No. 10/451,867, filed as application No. PCT/US01/49639 on Dec. 27, 2001, now abandoned.

(60) Provisional application No. 60/258,655, filed on Dec. 29, 2000.

(51) Int. Cl.
*C07H 21/04* (2006.01)
*C12N 15/63* (2006.01)
*C12N 15/85* (2006.01)

(52) U.S. Cl.
USPC ........................ 536/24.1; 435/320.1; 435/325

(58) Field of Classification Search
None
See application file for complete search history.

(56) References Cited

U.S. PATENT DOCUMENTS

| | | | |
|---|---|---|---|
| 4,196,265 | A | 4/1980 | Koprowski et al. |
| 4,554,101 | A | 11/1985 | Hopp |
| 4,736,866 | A | 4/1988 | Leder et al. |
| 4,769,331 | A | 9/1988 | Roizman et al. |
| 5,162,215 | A | 11/1992 | Bosselman et al. |
| 5,234,933 | A | 8/1993 | Marnett et al. |
| 5,260,203 | A | 11/1993 | Ladner et al. |
| 5,279,833 | A | 1/1994 | Rose |
| 5,286,634 | A | 2/1994 | Stadler et al. |
| 5,326,902 | A | 7/1994 | Seipp et al. |
| 5,399,346 | A | 3/1995 | Anderson et al. |
| 5,489,742 | A | 2/1996 | Hammer et al. |
| 5,550,316 | A | 8/1996 | Mintz |
| 5,573,933 | A | 11/1996 | Seamark et al. |
| 5,614,396 | A | 3/1997 | Bradley et al. |
| 5,625,125 | A | 4/1997 | Bennett et al. |
| 5,641,484 | A | 6/1997 | Hung et al. |
| 5,643,567 | A | 7/1997 | Hung et al. |
| 5,646,008 | A | 7/1997 | Thompson et al. |
| 5,648,061 | A | 7/1997 | Bernstein et al. |
| 5,651,964 | A | 7/1997 | Hung et al. |
| 5,741,957 | A | 4/1998 | Deboer et al. |
| 5,834,228 | A | 11/1998 | Becker et al. |
| 5,837,479 | A | 11/1998 | Young et al. |
| 5,872,011 | A | 2/1999 | Burley et al. |
| 6,087,111 | A | 7/2000 | Tinsley et al. |
| 6,096,318 | A | 8/2000 | Stevens |
| 6,132,720 | A | 10/2000 | Grimes et al. |
| 2004/0086903 | A1 | 5/2004 | Lareyre |

FOREIGN PATENT DOCUMENTS

| | | |
|---|---|---|
| WO | WO93/25521 | 12/1993 |
| WO | WO97/47763 | 12/1997 |

OTHER PUBLICATIONS

AQ927854 entered into database on Dec. 21, 1999.*
Baird and Glasier, "Contraception, BMJ.com. Clinical Review Science, Medicine, and the future" 319:969-972 (Oct. 9, 1999).
Costa et al., "Biol Reprod", 56:985-990 (1997).
Database DNA, Accession No. AF110520, Rowen, L., Sequence of the Mouse Major Histocompatibility Complex Class II Region. Direct Submission. (Dec. 23, 1998).
Database DNA, Accession No. AP001469, Hattori et al., *Homo sapiens* 47,859 Genomic DNA of 21q22.3. Direct Submission. (May 9, 2000).
Database mRNA, Accession No. AF073785, Pena et al., Sequencing and Relative Quantitation by Fluorescent-ratio PCR of Feline beta-lactoglobulin I, II, and III cDNAs. Mamm. Genome Sep. 2, 100, vol. 10, No. 6, pp. 560-564.
Fidler and Bernstein, "Infertility: From a Personal Public Health to a Problem, Public Health Reports" 114:494-511 (Nov./Dec. 1999).
Fouchecourt et al., "Identification, Immunolocalization, Regulation, and Postnatal Development of the Lipocalin EP17 (Epididymal Protein of 17 Kilodaltons) in the Mouse and Rat Epididymis", 144(3), 887-900 (2003).
International Preliminary Examination Report for PCT/US01/49639.
Kamischke and Nieschlag, "Analysis of medical treatment of male infertility, Human Reproduction" 14 (Supp 1): 1-23 (1999).
Krull et al., "Mol Reprod Dev", 34:16-34 (1993).
Lareyre J., et al., "Gene Duplication Gives Rise to a new 17 Kilodalton Lipocalin That Shows Epididymal Region-Specific Expression and Testicular Factor Regulation", Endocrinology 142(3): 1296-1308 (2001).
Lareyre, J.J., et al "J. Biol Chem.", 274:8282-8290 (1999).
Lareyre et al., "Endocrinology", 142:1296-1308 (2001).
Lufkin et al., "Proc Natl Acad Sci USA", 90:7225-7229 (1993).
Mendelsohn et al., "Development", 120:2749-2771 (1994).
Sonnenberg-Riethmacher et al., "Genes Dev", 10:1184-1193 (1996).
Yeung et al., "Biol Reprod", 61:1062-1069 (1999).
Skerra, A., "Alternative binding proteins: Anticalins—harnessing the structural plasticity of the lipocalin ligand pocket to engineer novel binding activities," FEBS Journal, vol. 275 pp. 2677-2683 ((2008).
Adelman et al., "In Vitro Deletional Mutagenesis for Bacterial Production of the 20,000-Dalton Form of Human Pituitary Growth Hormone," DNA, vol. 2, No. 3, pp. 183-193 (1983).

(Continued)

*Primary Examiner* — Celine Qian
(74) *Attorney, Agent, or Firm* — Jenkins, Wilson, Taylor & Hunt, P.A.

(57) ABSTRACT

Isolated nucleic acids comprising a lipocalin gene promoter region, isolated nucleic acids comprising a human lipocalin gene, isolated nucleic acids encoding a lipocalin polypeptide, isolated lipocalin polypeptides, and uses thereof. The disclosed lipocalin nucleic acids and polypeptides can be used to generate a mouse model of male infertility, for drug discovery screens, and for therapeutic treatment of fertility-related conditions.

5 Claims, 21 Drawing Sheets

(56) References Cited

OTHER PUBLICATIONS

Alam and Cook, "Review: Reporter Genes: Application to the Study of Mammalian Gene Transcription," Anal. Biochem., vol. 188, pp. 245-254 (1990).
Altschul et al., "Basic Local Alignment Search Tool," J. Mol. Biol., vol. 215, pp. 403-410 (1990).
Astraudo et al., "In Vivo Regulation of Rat Epididymal Proteins by Retinoids: Analysis by Two-Dimensional Electrophoresis," Arch. Androl., vol. 35, pp. 247-259 (1995).
Barber and Fayrer-Hosken, "Possible mechanisms of mammalian immunocontraception," J. Reprod. Immunol., vol. 46, pp. 103-124 (2000).
Barton, "Protein Sequence Alignment Techniques," Acta Cryst., vol. D54, pp. 1139-1146 (1998).
Batzer et al., "Amplification dynamics of human-specific (HS) alu family members," Nucleic Acid Res., vol. 19, pp. 3619-3623 (1991).
Brookes, "Review: The essence of SNPs," Gene, vol. 234, No. 2, pp. 177-186 (1999).
Chomczynski and Sacchi, "Single-Step Method of RNA Isolation by Acid Guanidinium Thiocyanate-Phenol-Chloroform Extraction," Anal. Biochem., vol. 162, pp. 156-159 (1987).
Conner et al., "Detection of sickle cell $\beta^S$-globin allele by hybridization with synthetic oligonucleotides," Proc. Natl. Acad. Sci. USA, vol. 80, pp. 278-282 (1983).
Cooper and Yeung, "Recent biochemical approaches to post-testicular, epididymal contraception," Hum. Reprod. Update, vol. 5, pp. 141-152 (1999).
Cubitt et al., "Understanding, improving and using green fluorescent proteins," Trends Biochem. Sci., vol. 20, pp. 448-455 (1995).
Diekman et al., "Evidence for a unique N-linked glycan associated with human infertility on sperm CD52: a candidate contraceptive vaccinogen," Immunol. Rev., vol. 171, pp. 203-211 (1999).
Feng et al., "Development of an Immunocontraceptive Vaccine," J. Reprod. Med., vol. 44, pp. 759-765 (1999).
Gorman et al., "The Igκ versus Igλ B Lymphocytes," Immunity, vol. 5, pp. 241-252 (1996).
Hall et al., "Direct Exposure of Mouse Spermatogenic Cells to High Doses of Adenovirus Gene Therapy Vector Does Not Result in Germ Cell Transduction," Hum. Gene Ther., vol. 11, No. 12, pp. 1705-1712 (2000).
Henikoff and Henikoff, "Amino acid substitution matrices from protein blocks," Proc. Natl. Acad. Sci. USA, vol. 89, pp. 10915-10919 (1992).
Henikoff and Henikoff, "Amino Acid Substitution Matrices," Adv. Protein Chem., vol. 54, pp. 73-97 (2000).
Henikoff et al., "Blocks-based methods for detecting protein homology," Electrophoresis, vol. 21, No. 9, pp. 1700-1706 (2000).
Huang et al., "Integrated Tools for Structural and Sequence Alignment and Analysis," Pac. Symp. Biocomput., vol. 230-241 (2000).
Hutchens and Yip, "New Desorption Strategies for the Mass Spectromic Analysis of Macromolecules," Rapid Commun. Mass Spectrom. vol. 7, pp. 576-580 (1993).
Karlin and Altschul, "Applications and statistics for multiple high-scoring segments in molecular sequences," Proc. Natl. Acad. Sci. USA, vol. 90, pp. 5873-5887 (1993).
Kestila, et al., "Positionally Cloned Gene for a Novel Glomerular Protein-Nephrin-Is Mutated in Congential Nephrotic Syndrome," Mol. Cell, vol. 1, pp. 575-582 (1998).
Kyte et al., "A Simple Method for Displaying the Hydropathic Character of a Protein," J. Mol. Biol., vol. 157, pp. 105-132 (1982).
Landgren et al., "A Ligase-Mediated Gene Detection Technique," Science, vol. 241, pp. 1077-1080 (1988).
Landgren et al., "DNA Diagnostics—Molecular Techniques and Automation," Science, vol. 242, pp. 229-237 (1988).
Li and Herskowitz, "Isolation of *ORC6*, a Component of the Yeast Origin Recognition Complex by a One-Hybrid System," Science, vol. 262, pp. 1870-1874 (1993).
Liedberg et al., "Surface Plasmon Resonance for Gas Detection and Biosensing," Sensors Actuators, vol. 4, pp. 299-304 (1983).
Luckow and Schutz, "CAT constructions with multiple unique restriction sites for the functional analysis of eukaryotic promoters and regulatory elements," Nucleic Acids Res., vol. 15, p. 5490 (1987).
Luo et al., "Cloning and Analysis of DNA-Binding Proteins by Yeast One-Hybrid and One-Two-Hybrid Systems," Biotechniques, vol. 20, No. 4, pp. 564-568 (1996).
Luyckx et al., "Diet-dependent hypercalciuria in transgenic mice with reduced CLC5 chloride channel expression," Proc. Natl. Acad. Sci. USA, vol. 96, No. 21, pp. 12174-12179 (1999).
Madge et al., "Thermodynamic Fluctuations in a Reacting System-Measurement by Fluorescence Correlation Spectroscopy," Phys. Rev. Lett., vol. 29, pp. 705-708 (1972).
Maiti et al., "Fluorescence correlation spectroscopy: Diagnostics for sparse molecules," Proc. Natl. Acad. Sci. USA, vol. 94, pp. 11753-11757 (1997).
Malmqvist, "Biospecific interaction analysis using biosensor technology," Nature, vol. 361, pp. 186-187 (1993).
Nachtigal et al., "Human chorionic somatomammotropin and growth hormone gene expression in rat pituitary tumour cells is dependent on proximal promoter sequences," Nuc. Acid Res., vol. 17, No. 11, pp. 4327-4337 (1989).
Naz, "Vaccine for contraception targeting sperm," Immunol. Rev., vol. 171, pp. 193-202 (1999).
Needleman and Wunsch, "A General Method Applicable to the Search for Similarities in the Amino Acid Sequence of Two Proteins," J. Mol. Biol., vol. 48, pp. 443-453 (1970).
Nikkanen et al., "Effect of Local Epididymal Levonorgestrel on the Fertilizing Ability of Male Rat, A Model for Post-Testicular Contraception," Contraception, vol. 61, pp. 401-406 (2000).
Office Communication corresponding to U.S. Appl. No. 10/451,867dated Jul. 13, 2007.
Office Communication corresponding to U.S. Appl. No. 10/451,867dated Feb. 8, 2007.
Ohtsuka et al., "An Alternative Approach to Deoxyoligonucleotides as Hybridization Probes by Insertion of Deoxyinosine at Ambiguous Codon Positions," J. Biol. Chem., vol. 260, pp. 2605-2608 (1985).
Ong et al., "Review: Epididymal retinoic acid-binding protein," Biochimica Biophysica Acta, vol. 1482, pp. 209-217 (2000).
Orita et al., "Detection of polymorphisms of human DNA by gel electrophoresis as single-strand conformation polymorphisms," Proc. Natl. Acad. Sci. USA, vol. 86, No. 8, pp. 2766-2770 (1989).
Palmiter and Brinster, "Transgenic Mice," Cell, vol. 41, pp. 343-345 (1985).
Paterson et al., "Immunocontraception with Zona pellucida Proteins," Cells Tissues Organs, vol. 166, pp. 228-232 (2000).
Pearson and Lipman, "Improved tools for biological sequence comparison," Proc. Natl. Acad. Sci. USA, vol. 85, pp. 2444-2448 (1988).
Postic et al., "Dual Roles for Glucokinase in Glucose Homeostasis as Determined by Liver and Pancreatic β Cell-specific Gene Knock-outs Using Cre Recombinase," J. Biol. Chem., vol. 275, No. 1, pp. 305-315 (1999).
Rose and Botstein, "Construction and Use of Gene Fusions to *lacZ* (β-Galactosidase) That are Expressed in Yeast," Meth. Enzymol., vol. 101, pp. 167-180 (1983).
Rossolini et al., "Use of deoxyinosine-containing primers vs degenerate primers for polymerase chain reaction based on ambiguous sequence information," Mol. Cell Probes, vol. 8, pp. 91-98. (1994).
Saiki et al., "A Novel Method for the Detection of Polymorphic Restriction Sites by Cleavage of Oligonucleotide Probes: Application to Sickle-Cell Anemia," Bio/Technology, vol. 3, pp. 1008-1012 (1985).
Saqi et al., "Protein Analyst—a distributed object environment for protein sequence and structure analysis," Bioinformatics, vol. 15, pp. 521-522 (1999).
Sauer, "Inducible Gene Targeting in Mice Using the Cre/lox System," Methods, vol. 14, No.4, pp. 381-392 (1998).
Singh et al., "Molecular Cloning of Sequence-Specific DNA Binding Proteins Using Recognition Site Probes," Biotechniques, vol. 7, pp. 252-261 (1989).
Smith and Waterman, "Comparison of Biosequences," Adv. Appl. Math., vol. 2, p. 482 (1981).

(56) References Cited

OTHER PUBLICATIONS

Srivastav, "Maturation-dependent glycoproteins containing both N- and O-linked oligosaccharides in epididymal sperm plasma membrane of rhesus monkeys (*Macaca mulatta*)," J. Reprod. Fertil., vol. 119, pp. 241-252 (2000).

Stoneking et al., "Population variation of human mtDNA control region sequences detected by enzymatic amplication and sequence-specific oligonucleotide probes," Am. J. Hum. Genet., vol. 48, No. 2, pp. 370-382 (1991).

Talwar, "Vaccines and passive immunological approaches for the control of fertility and hormone-dependent cancers," Immunol. Rev., vol. 171, pp. 173-192 (1999).

Tegtmeyer, "Function of Simian Virus 40 Gene A in Transforming Infection," J. Virol., vol. 15, No. 3, pp. 613-618 (1975).

Tobin et al., "Electrophoretic transfer of proteins from polyacrylamide gels to nitrocellulose sheets: Procedure and some applications," Proc. Natl. Acad. Sci. USA 76:4350-4354 (1979).

Vidal et al., "Reverse two-hybrid and one-hybrid systems to detect dissociation of protein-protein and DNA-protein interactions," Proc. Natl. Acad. Sci. USA, vol. 93, No. 19, pp. 10315-10320 (1996).

von Heiji, "A new method for predicting signal sequence cleavage sites," Nucleic Acid Res., vol. 14, pp. 4683-4690 (1986).

Wang et al., "Large-Scale Identification, Mapping, and Genotyping of Single-Nucleotide Polymorphisms in the Human Genome," Science, vol. 280, No. 5366, pp. 1077-1082 (1998).

Wolbach, "Tissue Changes Following Deprivation of Fat-Soluble A Vitamin," J. Exp. Med., vol. 42, pp. 753-777 (1925).

Wolf and Inoue, "Sperm Concentration Dependency in the Fertilization and Zonae Sperm Binding Properties of Mouse Eggs Inseminated In Vitro," J. Exp. Zool., vol. 196, pp. 27-38 (1976).

Worrall et al., "Purification of Contaminated Peptides and Proteins on Synthetic Membrane Surfaces for Matrix-Assisted Laser Desorptionnonization Mass Spectrometry," Anal. Biochem., vol. 70, pp. 750-756 (1998).

Yuan et al., "Comparison of Heteroduplex Analysis, Direct Sequencing, and Enzyme Mismatch Cleavage for Detecting Mutations in a Large Gene, FBN1," Hum. Mutat., vol. 14, No. 5, pp. 440-446 (1999).

* cited by examiner

```
Sequences producing significant alignments:

                                                                          Bits  Value
sp|P06911|ERBP_RAT  EPIDIDYMAL-RETINOIC ACID BINDING PROTEIN...            73   2e-12
gb|AAA41127.1|  (M12790) secretory protein B prepeptide [Rat...            73   2e-12
pdb|1EPA|B  Chain B, Epididymal Retinoic Acid-Binding Protei...            71   8e-12
gb|AAD09351.1|  (U68381) epididymal retinoic acid binding pr...            70   1e-11
ref|NP_031973.1|  epididymal retinoic acid-binding protein; ...            64   8e-10
sp|O02853|PGHD_BOVIN  PROSTAGLANDIN-H2 D-ISOMERASE PRECURSOR...            50   2e-05
gb|AAG30028.1|AF281353_1  (AF281353) prostaglandine D syntha...            49   3e-05
dbj|BAA12075.1|  (D83712) Prostaglandin D Synthase [Xenopus ...            49   4e-05
ref|NP_000945.1|  prostaglandin D2 synthase (21kD, brain) [H...            48   5e-05
pir||S52354  gene cpl-1 protein - African clawed frog >gi|66...            48   5e-05
gb|AAA36494.1|  (M61900) prostaglandin D synthase [Homo sapi...            46   3e-04
dbj|BAA86198.1|  (AB032480) prostaglandin D synthase [Macaca...            46   3e-04
sp|P35578|ESP4_LACVV  EPIDIDYMAL SECRETORY PROTEIN IV PRECUR...            44   0.001
sp|Q9XSM0|PGHD_SHEEP  PROSTAGLANDIN-H2 D-ISOMERASE PRECURSOR...            44   0.001
sp|Q29487|PGHD_FELCA  PROSTAGLANDIN-H2 D-ISOMERASE PRECURSOR...            43   0.002
gb|AAB27607.1|  beta-trace protein, prostaglandin D synthase...            43   0.002
prf||1917182A  androgen-dependent epididymal protein [Lacert...            43   0.002
dbj|BAA94343.1|  (AB040991) prostaglandin D synthase [Orycto...            42   0.004
sp|Q01584|LIPO_BUFMA  LIPOCALIN PRECURSOR >gi|104284|pir||S2...            42   0.004
pir||A45542  beta-lactoglobulin I - pig >gi|406773|emb|CAA38...            42   0.005
ref|NP_037147.1|  prostaglandin D synthase [Rattus norvegicu...            42   0.005
sp|O09114|PGHD_MOUSE  PROSTAGLANDIN-H2 D-ISOMERASE PRECURSOR...            42   0.005
gb|AAC62487.1|  (AF093791) androgen-regulated epipidymal sec...            41   0.007
gb|AAA53371.1|  (M25784) quiescence-specific protein [Gallus...            41   0.007
sp|Q9XS65|PGHD_CANFA  PROSTAGLANDIN-H2 D-ISOMERASE PRECURSOR...            41   0.007
gb|AAF35894.1|AF229030_1  (AF229030) lipocalin Q83 [Coturnix...            41   0.007
sp|P04939|MUPM_MOUSE  MINOR MAJOR URINARY PROTEIN 15 PRECURS...            41   0.009
sp|P07380|LACA_HORSE  BETA-LACTOGLOBULIN II PRECURSOR, MINOR...            41   0.009
sp|Q29095|PGHD_PIG  PROSTAGLANDIN-H2 D-ISOMERASE PRECURSOR (...            41   0.011
```

Predicted amino acid sequence comparison between MEP17 and sequence from human chromosome 9q

FIG. 11A

```
GATATCTAGCATGTTTCCAGTTTCTGGATATTTTGAATAAAGCTACTATGAACACAGTTGAGCCAGTGTCCTTGTGGGATGGTGGAGTATCTTTTGGGTATATGCCCAGGAGTGATATAG   -5174
CAGGGTCTTGGGGTAGAACTATTTCCAGTTTATTGAGAAACTGCCACATTGATTTTCAGAGTGGTTGTACCAGTTTTACTCCCACCAGCAATGGAGGAGTGTTCCCTTGTGTTCCATA   -5054
CCCTGTCACTTGAGGTGTTTTTTTGTTTTGTTTTAAGATTTTTTTTTCGAGACAGGGTTTCTCTGTATAGTCCTGTCTGTCCTGGAACTCACTTTGTAGACTAGGCTGGCCTAGAACT   -4934
                                                                                          ARBS
CAGAAATCCGCCTGCCTCTGCCTCCCAAGTGCTGGGATTAAAGGCGTGCGCCACCACACCCGGCTGTTTTAAGATTTTTTTAAAAAAAGATTTATTTATAATAATAAATATCTAAGTACA   -4814
                                                                                                                 Oct-1
CTGTAGCTGTCTTCAGACACACCAGAAGAGGGCATCAGATCTCATTACAGATGGTTGTGAGCCACCATGTGGTTGCTGGGATTTGAACTCAGGATCTTTGGAAGAGCAGTCAGTGCTCTT   -4694
                                       Oct-1                                                                       ARBS
AACCACTGAGCCATCTCTACAGCCCATCACTTGAGTTTTGAATCTTATCCATTCTGACAGTTGTAAGATGGAATCTCAGAGTCCTTTTGATTTGCATCTCCCTGATAACTAAGGACGTT   -4574
                                                                                                        Oct-1
GAACATTTCTTTAAGGGCTTCTCAGCCATTCGAGATTCCTGTTTAACTAGGAAACTCTTTACTAACTCCTTTCTTGCCTGTCACAGCCACTGTGAAGGGTTCACACATAATCGCTTCTCT   -4454
GCATCGCGTAGGTCCTAAGACCCCAGTCCCCAGGCCCTCAAGGCCTTTTCAGACTTCTACCCAACAATGGGTCTTCTGGGTAACATGATGGTAACACCACCCAAATCAGTTACTAGTTGA   -4334
GCTAGCCCACCAGAGCACCTGCCTAGGTCATCCCTTCAGTTCTGGAGCATGTAGGTCTACATTGCCTAGACCCCCTTCTATCTCCAGCACCGGTGAGGAGCCCCTGATGGGGATAATTCT   -4214
CTAACCAGCTCTGTGGGGATTGTAGGGGTGAGCAGGACCCAAGCACCTAGTGGGTGTGTCTGAGAGAAAGGAGGAAAATCAATGATCTTCCCATGTGCGTTTCTCTGGGTAAGGAGGTAC   -4094
TCAGGTGTCCTGAGTGACCAGTGCCAACATTCTCGGGCTATGTGCAGGGTGAGTTTTCTTCTGAGCTTGGGTCAGCAAGATCCTATCCCTGAAATCTGTGATCCCTACTACCTGTCGAGT   -3974
CTCATGCTTATGGTTTAGCTTAGACATGTCTGGTAGAAGATGCCACCCTGGTGTCTTGGGGCCATCATAATAAGCCAAGGCAAAGAGACAGAAAGAATTCTCTTTTAGTCCAAGAGACC   -3854
                                                                                       Oct-1
GAAGTCAGGAATCCATGTGTGTGGAGGCTAGAGGAGGGCTCTTGCCAATCTGCACCCCCAACCCCCAGCTTCTGGTCTTTCTTCTGTTCTGGGCAGTCTTAATCTTGACTGCATCACTAA   -3734
TATCTGCCTCTTTCTTCTGCCCATCTGTGTCTGAATTCTTCCATTCATAAGGATGCTGTCTTTGGGTTAGGGCCATCTGAACCTGTCTGCAGAAACCTTGTCTTCAAGTAAGATATTGTT   -3614
TGGAGGTTCTGGGTGGGGGATACTATTCAATCCAGTGTACCCCATGTTTTGCTAACCTTTGGGCCCCCCTTCTCAGGGCTTGTACCATATCTTTAATTGTATCATCCTGTTCCCAAGAAC   -3494
CCTGAAAGGGCAGAACTATTTTTCATCTACTGCTCCACTACAGGGTTAGGGTAGAAGTCCTTGGCATCTTGATACAGGCAGGTTCATGGGGAGGCCTACCCAACCAAACCAATGTAGAAA   -3374
                                                                                                    RARE
GCTGCCCAATTCCTACCCAAGCTCATTGCTAACAATTTTGGCACTCACAAAGCCACAGTAGTAGATGACATGTGAGTGTATAAAAGTCAGTGGATAGAGGGGGTGGGTGTAATACCGTAT   -3254
                                                                                                                SP-1
GGCTTATCCTGGGATGGAGACTTTGTGGTATTTCTTGTTCTTTTCCCAGCCTCCTAGTTCTCTGCATGCTGGTACTTTGCAGGTCATGATAGGCCTCTTATTATCCTTTCCTCTTGCCTG   -3134
                                                      SP-1                                                   Oct-1
CTTACCCTGAATGCCTGCTGTTTTGACAGTCCATGGATCTAAACACCTGTGCTGAGCTTACATGTTCTCCACTATCAGGTAGTTTTGAAAACGTAAGAAGTTAGACTCAATGTCAAATCA   -3014
CCCTGTCATTTTTCCTGTTACTATGGTCTTGGTCTCTCTTCTCAGGGCCTGGCAAGGCTTAGGGGTTACTAGTCCTGTAAGAATTAGGGATCCAGAAGTATGGCAGGTCTCTATGGTCTC   -2894
                                                                                                                      ARBS
TGGGAAGGTGCCTTGGAGAGGCATCTCTAGTCGGGTCAGTGGCAGTGTGGGAAGTTTTTACTGGTTTATAGATGCTTTGGTGACAGGATTATCTTTCCTTGCCTTTGTGGGTTGGCAGCC   -2774
TTGGGGGGCAGTGCCTAGCTTGTGGGGAGTATGGAGGATGTTTGACAAAGGACTGGTGATGGAGTGATTGTGCCCTTTTAGGGTAGGATGAACCTGGAGTTGCCAACCTCAAGAGTGTCA   -2654
CTCTCACTGTGATCTTTAGGGACTGAGAGATCCTCTTGGGTCCCACCTCCTTCCGTCCTGTGTTCCTTCTCTTGCTCTTCTCCTTTCACCCAATAAACAGATTCAGCATCCGCATGGCTC   -2534
```

FIG. 11B

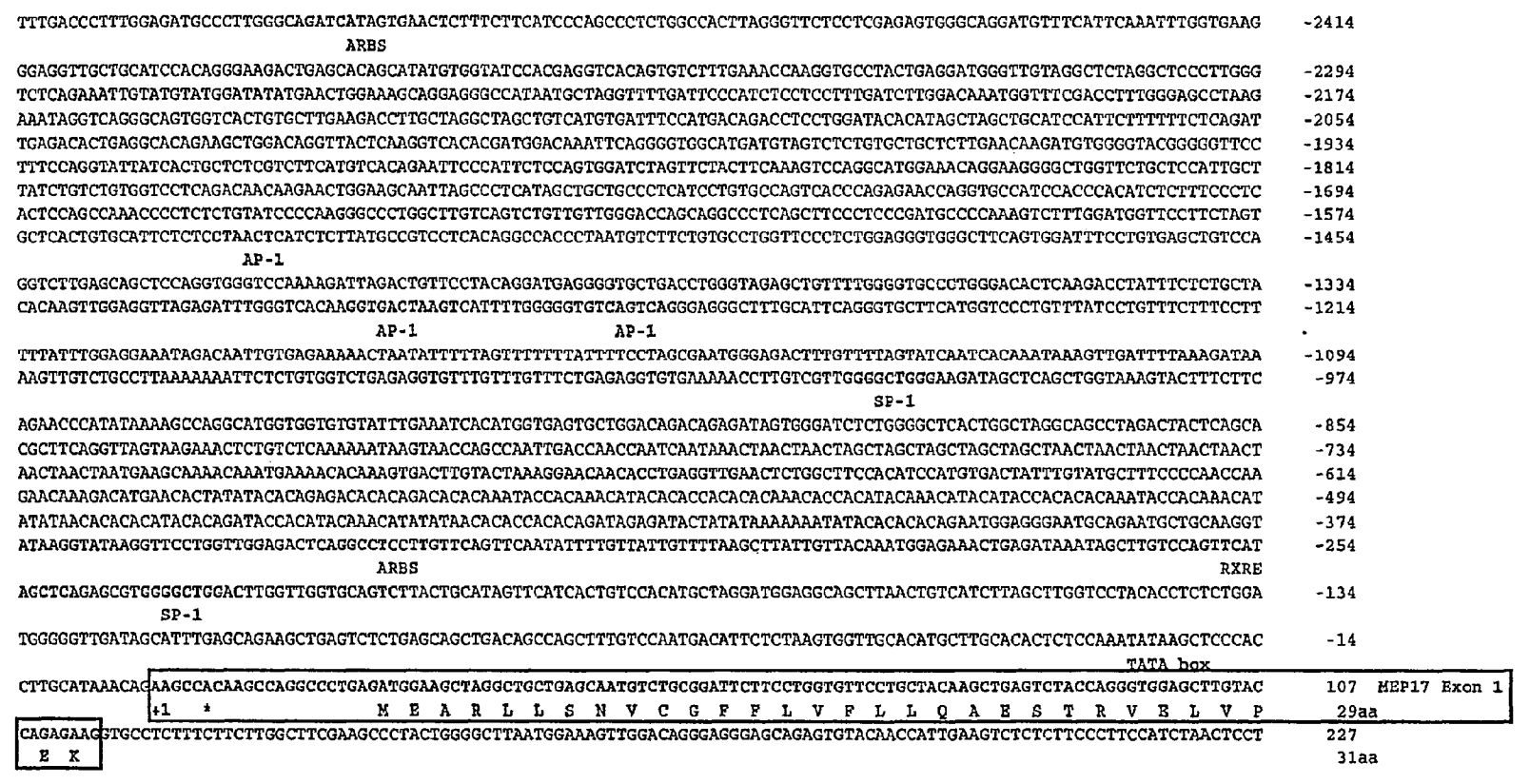

```
TTTGACCCTTTGGAGATGCCCTTGGGCAGATCATAGTGAACTCTTTCTTCATCCCAGCCCTCTGGCCACTTAGGGTTCTCCTCGAGAGTGGGCAGGATGTTTCATTCAAATTTGGTGAAG     -2414
                           ARBS
GGAGGTTGCTGCATCCACAGGGAAGACTGAGCACAGCATATGTGGTATCCACGAGGTCACAGTGTCTTTGAAACCAAGGTGCCTACTGAGGATGGGTTGTAGGCTCTAGGCTCCCTTGGG     -2294
TCTCAGAAATTGTATGTATGGATATATGAACTGGAAAGCAGGAGGGCCATAATGCTAGGTTTTGATTCCCATCTCCTCCTTTGATCTTGGACAAATGGTTTCGACCTTTGGGAGCCTAAG     -2174
AAATAGGTCAGGGCAGTGGTCACTGTGCTTGAAGACCTTGCTAGGCTAGCTGTCATGTGATTTCCATGACAGACCTCCTGGATACACATAGCTAGCTGCATCCATTCTTTTTTCTCAGAT     -2054
TGAGACACTGAGGCACAGAAGCTGGACAGGTTACTCAAGGTCACACGATGGACAAATTCAGGGGTGGCATGATGTAGTCTCTGTGCTGCTCTTGAACAAGATGTGGGGTACGGGGGTTCC     -1934
TTTCCAGGTATTATCACTGCTCTCGTCTTCATGTCACAGAATTCCCATTCTCCAGTGGATCTAGTTCTACTTCAAAGTCCAGGCATGGAAACAGGAAGGGGCTGGTTCTGCTCCATTGCT     -1814
TATCTGTCTGTGGTCCTCAGACAACAAGAACTGGAAGCAATTAGCCCTCATAGCTGCTGCCCTCATCCTGTGCCAGTCACCCAGAGAACCAGGTGCCATCCACCCACATCTCTTTCCCTC     -1694
ACTCCAGCCAAACCCCTCTCTGTATCCCCAAGGGCCCTGGCTTGTCAGTCTGTTGTTGGGACCAGCAGGCCCTCAGCTTCCCTCCCGATGCCCCAAAGTCTTTGGATGGTTCCTTCTAGT     -1574
GCTCACTGTGCATTCTCTCCTAACTCATCTCTTATGCCGTCCTCACAGGCCACCCTAATGTCTTCTGTGCCTGGTTCCCTCTGGAGGGTGGGCTTCAGTGGATTTCCTGTGAGCTGTCCA     -1454
                 AP-1
GGTCTTGAGCAGCTCCAGGTGGGTCCAAAAGATTAGACTGTTCCTACAGGATGAGGGGTGCTGACCTGGGTAGAGCTGTTTTGGGGTGCCCTGGGACACTCAAGACCTATTTCTCTGCTA     -1334
CACAAGTTGGAGGTTAGAGATTTGGGTCACAAGGTGACTAAGTCATTTTGGGGGTGTCAGTCAGGGAGGGCTTTGCATTCAGGGTGCTTCATGGTCCCTGTTTATCCTGTTTCTTTCCTT     -1214
                              AP-1                    AP-1                                                                     .
TTTATTTGGAGGAAATAGACAATTGTGAGAAAAACTAATATTTTTAGTTTTTTTATTTTCCTAGCGAATGGGAGACTTTGTTTTAGTATCAATCACAAATAAAGTTGATTTTAAAGATAA     -1094
AAGTTGTCTGCCTTAAAAAAATTCTCTGTGGTCTGAGAGGTGTTTGTTTGTTTCTGAGAGGTGTGAAAAACCTTGTCGTTGGGGCTGGGAAGATAGCTCAGCTGGTAAAGTACTTTCTTC      -974
                                                                                      SP-1
AGAACCCATATAAAAGCCAGGCATGGTGGTGTGTATTTGAAATCACATGGTGAGTGCTGGACAGACAGAGATAGTGGGATCTCTGGGGCTCACTGGCTAGGCAGCCTAGACTACTCAGCA      -854
CGCTTCAGGTTAGTAAGAAACTCTGTCTCAAAAAATAAGTAACCAGCCAATTGACCAACCAATCAATAAACTAACTAACTAGCTAGCTAGCTAGCTAGCTAACTAACTAACTAACTAACT      -734
AACTAACTAATGAAGCAAAACAAATGAAAACACAAAGTGACTTGTACTAAAGGAACAACACCTGAGGTTGAACTCTGGCTTCCACATCCATGTGACTATTTGTATGCTTTCCCCAACCAA      -614
GAACAAAGACATGAACACTATATACACAGAGACACACAGACACACAAATACCACAAACATACACACCACACACAAACACCACATACAAACATACATACCACACACAAATACCACAAACAT      -494
ATATAACACACACATACACAGATACCACATACAAACATATATAACACACCACACAGATAGAGATACTATATAAAAAAATATACACACACAGAATGGAGGGAATGCAGAATGCTGCAAGGT      -374
ATAAGGTATAAGGTTCCTGGTTGGAGACTCAGGCCTCCTTGTTCAGTTCAATATTTTGTTATTGTTTTAAGCTTATTGTTACAAATGGAGAAACTGAGATAAATAGCTTGTCCAGTTCAT      -254
                              ARBS                                                                                     RXRE
AGCTCAGAGCGTGGGGCTGGACTTGGTTGGTGCAGTCTTACTGCATAGTTCATCACTGTCCACATGCTAGGATGGAGGCAGCTTAACTGTCATCTTAGCTTGGTCCTACACCTCTCTGGA      -134
          SP-1
TGGGGGTTGATAGCATTTGAGCAGAAGCTGAGTCTCTGAGCAGCTGACAGCCAGCTTTGTCCAATGACATTCTCTAAGTGGTTGCACATGCTTGCACACTCTCCAAATATAAGCTCCCAC       -14
                                                                                                                  TATA box
CTTGCATAAACAGAAGCCACAAGCCAGGCCCTGAGATGGAAGCTAGGCTGCTGAGCAATGTCTGCGGATTCTTCCTGGTGTTCCTGCTACAAGCTGAGTCTACCAGGGTGGAGCTTGTAC      107  MEP17 Exon 1
             +1   *                M  E  A  R  L  L  S  N  V  C  G  F  F  L  V  F  L  L  Q  A  E  S  T  R  V  E  L  V  P       29aa
CAGAGAAGGTGCCTCTTTCTTCTTGGCTTCGAAGCCCTACTGGGGCTTAATGGAAAGTTGGACAGGGAGGGAGCAGAGTGTACAACCATTGAAGTCTCTCTTCCCTTCCATCTAACTCCT      227
  E  K                                                                                                                          31aa
```

Chimeric constructs of MEP 17 promoter ligated to the CAT reporter gene

FIG. 13A

Oct-1 Oct-1

TGTTTATTTTATTATTTTTTTTTTTAAATTTATTTAACATAATTTTATTAATAATAATAATAAATATAGTTTGTAAATTTTAAAAATA-5041

GATA

AAAGAGAAGAGATAAAGAATAGATTAAATGAATTATATAAATGAATTAAGGTAATACTCAATCCTTTGGATATGTGGGATTATACACCATATAATTTTGTTATATTTAATAT-4929

TAGTATATATGGTAGGGTGTATGTGAGAAAAGGTAAAACTTAAAAAAGCGGTGAATTACAAGATCGGTAACGAAGGTCGAAAAGAAAGGAAATAGCGGGTGTCTGGTGATGT-4817

SP1

CTTGGATTTGAGGGTCGGGGGTTTCGAACTCTTTTTAAGGTCCATTATTTAGGCGCGGCGGGGAGAGAGGTATGTAAAACCGCAAGATGGGGTCCTTATCAGGATAAGGACC-4705

ACGAGTGACTGTTAGCAGAAAGTAATATCATGAGGAAACAGTAAAAAAAATACTTATGAGTTGGGTTGGGAGGGGACTGAGCTCTGAGAAAGGACCCCAGTTCACTATGTCA-4593

Lyf-1

AAAACGAAAAAAAGGCAAGGCGCAGTGGCTCACGCCTGTAATCCCGGCACTTTGGGAGGCCAAGGAGGGCAGATCACCTGAGGTCAGGAGTTTGAGACCAGCCTGACCAACA-4481

TGGTGAAATCCTGTCTCTACTAAAAATGCAAAAAAAATTAGACGGGCATGGTGGCTACTGTTATCCCAGCTACATGGGAGGCTGAGGCAGGAGAATCGCTTGAACCCGGGAG-4369

C/EBP SRY

GTGGAGATTGCAGTGAGCTGAGATTGCACCACTGCACTCCAGCCTGAGTGACAGAGTGAGACCCCGTCTTAAAAAACAAAACAAGGCCAGGCACGGTGGCTCATGCCTGCAA-4257

TCCCAGCACTCTGGGAGGCTGAGGCAGGTGGATCACAAGGTCAGGAGATCGAGACCATCCTGGCTAACATGGTGAAACCCTGTCTCTACTAAAAATACAAAGAATTATCCCA-4145

GCATGGTGGTGGACGCCTGTGGTCCCAGCTACTCCGGAGGCTGAGGTGGGAGAATGGCGTGAACCCAGGAGGTGGAGCTTGCAGTGAGCTGAGATTGCGCCACAGCACTCCA-4033

GCCTGGGCGACAGAGCGAGACTCCATCTCAAAAAAAGAAAAAAAAAAAAAAAAAAAAAAAGAAAAAAAAGAAAAAAGAAAAAAAGAAAAGAAAACGAAGAAAAACCACAAATA-3921

AATAAAAGTTGAGGTATGATGTATGCACAGCTGCATTCGCCCCTTTGAGGGCACAGTTGTGTGAGTTTAGACAAATGCAAATGTTCATGGAACCACTGCAAGTGCGACACAG-3809

CAGCTCTGGTGCCCACAAAGCTTCCTCGAGGTCCCTTGCGGTCAATCACTGCCCGCACCTCAGCCCTCAGAGCCACTGGGAAGCCCCCTGCCCTGTGGGCTCACCTGTCCTA-3697

GAACGTCGTATAAAAGGAGTCGCAGATCGCAGCCTTTTCCACCTGGCTTCTGTCCCTCTGCAGGCTGCACCTGGGATTCAGCCACCTTCGTTCCTTTTACTGCTGAGTGTCC-3585

ATCACGTGCTGCTCATGCAGAAGTGCTCAAGTTCGCTGTAAACGTAGTTTTCATTTCTCCCGGGTGGAGACCTCCATAAGTAGGTAGGTTGGTGGAATGTTTCACTGCATGA-3473 c-Ets GATA

GAGTCTGCCAGGAAGTTTTGCAGTGTGGTCCCGTCTTGTTCTTCGCGCAGAGGGTGATAGCTCTGCTGACTCCCAGCCCTCACAGGCTCTAGGGATTGAGCCTGTTTCTGTG-3361

FIG. 13B

GAACGCCTTCCATGGTCTGCGAGGTGCACAGAGGGGTCTCAAAAAGCTTCCAGGTTGCATCTTCCCATGGACTGATGCTGAGCGTGTTCTCATGTCCCATCCGGATGTTTTC-3249

SRY

TTTGGTGGAGTATCTTTTCAGATCTCTTGCCTTTTTATTTTTATTTGTTTATATATATATTTTGAGACGGAATTTTGCTCTTTCACTTAGGTTGGAGTGCAACGGCGCGATC-3137

TTGGCTCACTGCAACCTCCCCCCACCCACCTCACTTTGGGTTCAAGCGATTCTCCTGCCTCAGCCTCCCGAGTAGCTGGGACTACAGGCGCCCGCCACCATGCCCGGCTAAT-3025

GATA Lyf-1

TTTTGTATTTTGAGAAGAGATAGGGTTTCACCATGTTGGCCAGGCTGGTCTCGAACTCCTGACCTCAGGTGATCCACCCGCCTCGGCCTCCCAAAATGCGAGGATCACAGGC-2913

AP-1

GTGAGATGCCACACCTGGCCTCTTTTTATTTTTAATGGAGTGGCTTGTTTTCTTATTACTCAGTCTTGGGAGTTCCTCATGGATGCTGGATTTCAGTCTCGTCTCAGGTGTA-2801

TGCGTTTTGTAGATGTTTTCTGTAGGGACCAGCCCCACAGGGTTGGTGAGTTTCTCCCTGTGTGCTGAGATGAGAGGGCATAGAAATAAGGACACAAGAAAAAGACATAAAA-2689

GAAAAGACAGCTGGGCCTGGGGACCACTACCACCAAGACGTGGAGACCGGTAGTGGCCCCGAATGTCTGGCTGTGCTGATATTTATTGGATACAAAGCAAAAGGGACAGGGT-2577

AP-1 CREB AP-1

AAAGAGTGTGAGTCATCTCCAATGATAGGTAAGGTGACGTGAGTCACGTGTCCACCGGATGGGGGGCCCTTCCCTGTTTGGCAGCCAAGGCGGAGAGAGAGAGAGAGAGACA-2465

Oct-1 GATA

GCTTACATCATTATTTCTGCATATCAGAGACTTTTAGTACTTTCACTAATTGACTACTGCTATCTAGAAGGCAGAGCCAGGTGTACAGGATGGAACATGAAGGCGGACTACG-2353

GATA AP-1

AGCGTGACCACTGAAGCACAGCATCACAGGGAGACGGTTAGGCCTCTGGATAACTGCGGGCAGGTCTGACTGATGTCAGGCCCTCCACAGGAGGTGGAGGAGTAGAGTCCTC-2241

TCTAAGCTCCCCCGGGGGAAAGGGAGACTCCCTTTCCCTGTCTGCTAAGTAGCAGGTGTTTTCCCTTGACACTGACGCTACTGCTAGATCACGGTCCGCTTGGCAACCGGTG-2129

CREB

TCTTCCCAGACGCTGGCGTCACCACTAGACCAAGGAGCCCTCTGGTGGCCCTGTCCGGCGTAACAGAAGGCTCGCACTCTTGTCTTCTGGTCACTTCTCACTATGTCCCCTC-2017

GATA Oct-1

AGCTCCTATCTCTGTATGGCCTGGTTTTTCCTAGGTTATAATTGTAGAGCAAGGATTATTATAATATTGGAATAAAGAGTAATTGCTACAAGCTAATGATTAATAATATTCA-1905

Oct-1

TATATAATCATGTCTATGATCTAGATCTAGTATAACTCTTGTTATTTTATATATTTTATTAAACTGGAACAGCTCGTGCCCTCGGTCTCTTGCTTCGGCATCTGGGTGGCTT-1793

SP1

GCTGACCACAGTTTTCCTGCTGTATCTAACTGCTGGCTTAGGTGAACCTGTCAGGGGCGTGGCTGGGAACTGGAACCTCCTGAAGACCAGTGGAGGCCACAAGCAGAAGCCC-1681

TCGGCTCCTTCCCTTCCCCGATGCTGGGGGCCAAGGTCTTTCTCTGACCCTGTCCCCCCCTCACGTTACCAGTGGAGGGTGTCCAGGTTCTTGGCATTTTGAACAAAGAAT-1569

FIG. 13C

SRY
TGGACAAAACACACAAACAAAGCAAGGAAAGAATGAAGCAACAAAAGCAGAAATTTATTGAAAATGAAAGCACTCTTTACAGGGTGGGAGCGGGCTGAGCAAGCAGCTCAAG-1457

GGCCCCGGTTACAGAATTTTCTGGTGTTTCAATATCCTCTAGCGGTTTACCATTGGTTACTTGGTGTATGCCCTATGTAAATGAAGAGGATGAAGTCAAAGTCATTTTCTCG-1345

Lyf-1
GCTGAGCATACTGTCACGCCTGTAATCCCAGTACTTTGGGAGGCTGAGGTGGGTGTATCACCTGAGGTCGGGAGTTCAAGACCAGCCTGATGAACATGGAGAAACCCCGTCT-1233

GATA
CTACTAAAAATACAAAATTAGCTGGGTGTGGTGGCGGGTGCCTGTAATCCCAGATAGTCAGGAGGCTGAGGCAGGAAAATCGCTTAAACCCGGGAGGCAGAGGCTGCAGAGA-1121

SRY SRYSRY
GCCAAGGAGTGCACCACTGCACTCCAGCCTGGGCAACAAGAGCAAAACTCCATCTCAAAAAACAAACAAACAAAACGAAGTCATGTACTCGGTATGAGCCCTACGTAAACGG-1009

AGAGGATGGAGTGAAGGTACAAAGCCATTCACATTCCCGTCATCGTTAGTGTTTCCAGTTGATTTGGTTCTAGGATGCCCTTGGGCTCCCTGCGTCCAGGCCCTCTTCTCCT -897

GCCTCACTCTCACTCCAGAGGACTGGCAGTGCTGGCCTCCCTGGCAGGACTCCCGCCCCTGACCAGAGGGGTCTGGGCGTGCTCCGAGGCCACCTGCTGCTCCTTGCCCAGT -785

CREB
GTCCCTGGGTGCTCTGTGGGGACACAGAGAGGTCACTTGGGAGGTTCCTGCCTCTGCCAGACTGCGGCGCCTTCCTGGCGTCATTGCCCCCTGCACGCTTATACAACCAGTG -673

GATA GATA
ATAAGGCGGTATCCAATGCCGTAATCCTCCCCAGGGCCAGCCCAGCCCTGTCCGGTCCCGTCCGGTCCCTGGCCTGCTTGCTGGGAGCCCAGCTGGGGGCTGCATCGGGGGT -561

SP1
GGTGGGGGTCTGGAGTGAGGGGTGCCCAGGCCTCTCTCACAGTGTGGGGGCACAAGCTCTGCCCTGGACACTCTGCCAGTGTGACCCTACCCCCCATGTTGGGGGTGAGAGA -449

AGGGGGCTTTCTGGGTGGCCAGATCCCAGGAGAGGGGGCCTAGCCAGACCAACCCCAGCCCAGCTCTCTGCAGCTGTACCCCAAAGGCCCTGGCCCAGCCCAGCCAGACAGA -337

GTGTGGACAGAGGGGCTTGGGTGCGAGTCCAGGCAAGGCAGGACAAGTCTCTGCTGTGGCTTGGCAGTGGCCCCGTGACTGGTGACATAGTCTGGCAGGCCTAGGGGACAAA -225

SP1 Sox5
TCCTCAGCCCGGGTGCATCAGGCCAGAGCCTGGCTGTCTGGAGCCCTCCAGGAAATGACCCCCCGGGCTGGGGGACATCCGAGTGATTGTGCCAAACAATGGACAAGGGGGC -113

TATA box
CGGAGTCTCAGAGCCGAAGTGCCTTCCGCTTCCATCTGCTCCGCCCAGGAGCAGGTGCACCCAGGTGGTGGCCTGGGCTATAAAGCTGGCCCCCTGGGGCTTGGGGACTCAG -1 mEP17 targeting vector construction

| FIG. 16A | FIG. 16B |
|---|---|

Expression of the recombinant MEP17

SEQUENCE LISTING

<160> NUMBER OF SEQ ID NOS: 11

<210> SEQ ID NO 1
<211> LENGTH: 5315
<212> TYPE: DNA
<213> ORGANISM: Mus musculus
<220> FEATURE:
<221> NAME/KEY: 5'UTR
<222> LOCATION: (1)..(5315)

<400> SEQUENCE: 1

```
gatatctagc atgtttccag tttctggata ttttgaataa agctactatg aacacagttg      60

agccagtgtc cttgtgggat ggtggagtat cttttgggta tatgcccagg agtgatatag     120

cagggtcttg gggtagaact atttccagtt tattgagaaa ctgccacatt gatttttcag     180

agtggttgta ccagttttta ctcccaccag caatggagga gtgttccctt gtgttccata     240

ccctgtcact tgaggtgttt ttttgttttt gttttaagat tttttttttc gagacagggt     300

ttctctgtat agtcctgtct gtcctggaac tcactttgta gactaggctg gcctagaact     360

cagaaatccg cctgcctctg cctcccaagt gctgggatta aaggcgtgcg ccaccacacc     420

cggctgtttt aagatttttt taaaaaaaga tttatttata ataataaata tctaagtaca     480

ctgtagctgt cttcagacac accagaagag ggcatcagat ctcattacag atggttgtga     540

gccaccatgt ggttgctggg atttgaactc aggatctttg gaagagcagt cagtgctctt     600

aaccactgag ccatctctac agcccatcac ttgagttttt gaatcttatc cattctgaca     660

gttgtaagat ggaatctcag agtccttttg atttgcatct ccctgataac taaggacgtt     720

gaacatttct ttaagggctt ctcagccatt cgagattcct gtttaactag gaaactcttt     780

actaactcct ttcttgcctg tcacagccac tgtgaagggt tcacacataa tcgcttctct     840

gcatcgcgta ggtcctaaga ccccagtccc caggccctca aggccttttc agacttctac     900

ccaacaatgg gtcttctggg taacatgatg gtaacaccac ccaaatcagt tactagttga     960
```

-continued

```
gctagcccac cagagcacct gcctaggtca tcccttcagt tctggagcat gtaggtctac   1020
attgcctaga ccccttcta tctccagcac cggtgaggag cccctgatgg ggataattct   1080
ctaaccagct ctgtggggat tgtaggggtg agcaggaccc aagcacctag tgggtgtgtc   1140
tgagagaaag gaggaaaatc aatgatcttc ccatgtgcgt ttctctgggt aaggaggtac   1200
tcaggtgtcc tgagtgacca gtgccaacat tctcgggcta tgtgcagggt gagttttctt   1260
ctgagcttgg gtcagcaaga tcctatccct gaaatctgtg atccctacta cctgtcgagt   1320
ctcatgctta tggttttagc ttagacatgt ctggtagaag atgccaccct ggtgtcttgg   1380
ggccatcata ataagccaag gcaaagagac agaaagaatt ctcttttagt ccaagagacc   1440
gaagtcagga atccatgtgt gtggaggcta gaggagggct cttgccaatc tgcaccccca   1500
acccccagct tctggtcttt cttctgttct gggcagtctt aatcttgact gcatcactaa   1560
tatctgcctc tttcttctgc ccatctgtgt ctgaattctt ccattcataa ggatgctgtc   1620
tttgggttag ggccatctga acctgtctgc agaaaccttg tcttcaagta agatattgtt   1680
tggaggttct gggtggggga tactattcaa tccagtgtac cccatgtttt gctaaccttt   1740
gggccccct tctcagggct tgtaccatat ctttaattgt atcatcctgt tcccaagaac   1800
cctgaaaggg cagaactatt tttcatctac tgctccacta cagggttagg gtagaagtcc   1860
ttggcatctt gatacaggca ggttcatggg gaggcctacc caaccaaacc aatgtagaaa   1920
gctgcccaat tcctacccaa gctcattgct aacaattttg gcactcacaa agccacagta   1980
gtagatgaca tgtgagtgta taaaagtcag tggatagagg gggtgggtgt aataccgtat   2040
ggcttatcct gggatggaga ctttgtggta tttcttgttc ttttcccagc ctcctagttc   2100
tctgcatgct ggtactttgc aggtcatgat aggcctctta ttatcctttc ctcttgcctg   2160
cttaccctga atgcctgctg ttttgacagt ccatggatct aaacacctgt gctgagctta   2220
catgttctcc actatcaggt agttttgaaa acgtaagaag ttagactcaa tgtcaaatca   2280
ccctgtcatt tttcctgtta ctatggtctt ggtctctctt ctcagggcct ggcaaggctt   2340
aggggttact agtcctgtaa gaattaggga tccagaagta tggcaggtct ctatggtctc   2400
tgggaaggtg ccttggagag gcatctctag tcgggtcagt ggcagtgtgg gaagttttta   2460
ctggtttata gatgctttgg tgacaggatt atctttcctt gcctttgtgg gttggcagcc   2520
ttgggggggca gtgcctagct tgtggggagt atggaggatg tttgacaaag gactggtgat   2580
ggagtgattg tgccctttta gggtaggatg aacctggagt tgccaacctc aagagtgtca   2640
ctctcactgt gatctttagg gactgagaga tcctcttggg tcccacctcc ttccgtcctg   2700
tgttccttct cttgctcttc tcctttcacc caataaacag attcagcatc cgcatggctc   2760
tttgaccctt tggagatgcc cttgggcaga tcatagtgaa ctctttcttc atcccagccc   2820
tctggccact tagggttctc ctcgagagtg ggcaggatgt ttcattcaaa tttggtgaag   2880
ggaggttgct gcatccacag ggaagactga gcacagcata tgtggtatcc acgaggtcac   2940
agtgtctttg aaaccaaggt gcctactgag gatgggttgt aggctctagg ctcccttggg   3000
tctcagaaat tgtatgtatg gatatatgaa ctggaaagca ggagggccat aatgctaggt   3060
tttgattccc atctcctcct ttgatcttgg acaaatggtt tcgacctttg ggagcctaag   3120
aaataggtca gggcagtggt cactgtgctt gaagaccttg ctaggctagc tgtcatgtga   3180
tttccatgac agacctcctg gatacacata gctagctgca tccattcttt tttctcagat   3240
tgagacactg aggcacagaa gctggacagg ttactcaagg tcacacgatg gacaaattca   3300
ggggtggcat gatgtagtct ctgtgctgct cttgaacaag atgtggggta cgggggttcc   3360
```

```
tttccaggta ttatcactgc tctcgtcttc atgtcacaga attcccattc tccagtggat   3420

ctagttctac ttcaaagtcc aggcatggaa acaggaaggg gctggttctg ctccattgct   3480

tatctgtctg tggtcctcag acaacaagaa ctggaagcaa ttagccctca tagctgctgc   3540

cctcatcctg tgccagtcac ccagagaacc aggtgccatc cacccacatc tctttccctc   3600

actccagcca aacccctctc tgtatcccca agggccctgg cttgtcagtc tgttgttggg   3660

accagcaggc cctcagcttc cctcccgatg ccccaaagtc tttggatggt tccttctagt   3720

gctcactgtg cattctctcc taactcatct cttatgccgt cctcacaggc caccctaatg   3780

tcttctgtgc ctggttccct ctggagggtg ggcttcagtg gatttcctgt gagctgtcca   3840

ggtcttgagc agctccaggt gggtccaaaa gattagactg ttcctacagg atgaggggtg   3900

ctgacctggg tagagctgtt ttggggtgcc ctgggacact caagacctat ttctctgcta   3960

cacaagttgg aggttagaga tttgggtcac aaggtgacta agtcattttg gggggtgtcag   4020

tcagggaggg ctttgcattc agggtgcttc atggtccctg tttatcctgt ttctttcctt   4080

tttatttgga ggaaatagac aattgtgaga aaaactaata tttttagttt ttttattttc   4140

ctagcgaatg ggagactttg ttttagtatc aatcacaaat aaagttgatt ttaaagataa   4200

aagttgtctg ccttaaaaaa attctctgtg gtctgagagg tgtttgtttg tttctgagag   4260

gtgtgaaaaa ccttgtcgtt ggggctggga agatagctca gctggtaaag tactttcttc   4320

agaacccata taaaagccag gcatggtggt gtgtatttga aatcacatgg tgagtgctgg   4380

acagacagag atagtgggat ctctggggct cactggctag gcagcctaga ctactcagca   4440

cgcttcaggt tagtaagaaa ctctgtctca aaaaataagt aaccagccaa ttgaccaacc   4500

aatcaataaa ctaactaact agctagctag ctagctagct aactaactaa ctaactaact   4560

aactaactaa tgaagcaaaa caaatgaaaa cacaaagtga cttgtactaa aggaacaaca   4620

cctgaggttg aactctggct tccacatcca tgtgactatt tgtatgcttt ccccaaccaa   4680

gaacaaagac atgaacacta tatacacaga gacacacaga cacacaaata ccacaaacat   4740

acacaccaca cacaaacacc acatacaaac atacatacca cacacaaata ccacaaacat   4800

atataacaca cacatacaca gataccacat acaaacatat ataacacacc acacagatag   4860

agatactata taaaaaaata tacacacaca gaatggaggg aatgcagaat gctgcaaggt   4920

ataaggtata aggttcctgg ttggagactc aggcctcctt gttcagttca atattttgtt   4980

attgttttaa gcttattgtt acaaatggag aaactgagat aaatagcttg tccagttcat   5040

agctcagagc gtggggctgg acttggttgg tgcagtctta ctgcatagtt catcactgtc   5100

cacatgctag gatggaggca gcttaactgt catcttagct tggtcctaca cctctctgga   5160

tgggggttga tagcatttga gcagaagctg agtctctgag cagctgacag ccagctttgt   5220

ccaatgacat tctctaagtg gttgcacatg cttgcacact ctccaaatat aagctcccac   5280

cttgcataaa cagaagccac aagccaggcc ctgag                              5315


<210> SEQ ID NO 2
<211> LENGTH: 30865
<212> TYPE: DNA
<213> ORGANISM: Homo sapiens

<400> SEQUENCE: 2

tgtttatttt tattattttt ttttttaaa tttatttaac ataattttta ttaataataa     60

taataaatat agtttgtaaa ttttaaaaat aaaagagaag agataaagaa tagattaaat    120

gaattatata aatgaattaa ggtaatactc aatcctttgg atatgtggga ttatacacca    180
```

-continued

```
tataattttg ttatatttaa tattagtata tatggtaggg tgtatgtgag aaaaggtaaa    240
acttaaaaaa gcggtgaatt acaagatcgg taacgaaggt cgaaaagaaa ggaaatagcg    300
ggtgtctggt gatgtcttgg atttgagggt cgggggtttc gaactctttt taaggtccat    360
tatttaggcg cggcggggag agaggtatgt aaaaccgcaa gatggggtcc ttatcaggat    420
aaggaccacg agtgactgtt agcagaaagt aatatcatga ggaaacagta aaaaaaatac    480
ttatgagttg ggttgggagg ggactgagct ctgagaaagg accccagttc actatgtcaa    540
aaacgaaaaa aaggcaaggc gcagtggctc acgcctgtaa tcccggcact ttgggaggcc    600
aaggagggca gatcacctga ggtcaggagt ttgagaccag cctgaccaac atggtgaaat    660
cctgtctcta ctaaaaatgc aaaaaaaatt agacgggcat ggtggctact gttatcccag    720
ctacatggga ggctgaggca ggagaatcgc ttgaacccgg gaggtggaga ttgcagtgag    780
ctgagattgc accactgcac tccagcctga gtgacagagt gagaccccgt cttaaaaaac    840
aaaacaaggc caggcacggt ggctcatgcc tgcaatccca gcactctggg aggctgaggc    900
aggtggatca caaggtcagg agatcgagac catcctggct aacatggtga aaccctgtct    960
ctactaaaaa tacaaagaat tatcccagca tggtggtgga cgcctgtggt cccagctact   1020
ccggaggctg aggtgggaga atggcgtgaa cccaggaggt ggagcttgca gtgagctgag   1080
attgcgccac agcactccag cctgggcgac agagcgagac tccatctcaa aaaaagaaaa   1140
aaaaaaaaaa aaaaaaaaga aaaaaaagaa aaaagaaaaa aagaaaagaa aacgaagaaa   1200
aaccacaaat aaataaaagt tgaggtatga tgtatgcaca gctgcattcg cccctttgag   1260
ggcacagttg tgtgagttta gacaaatgca aatgttcatg gaaccactgc aagtgcgaca   1320
cagcagctct ggtgcccaca aagcttcctc gaggtccctt gcggtcaatc actgcccgca   1380
cctcagccct cagagccact gggaagcccc ctgccctgtg ggctcacctg tcctagaacg   1440
tcgtataaaa ggagtcgcag atcgcagcct tttccacctg gcttctgtcc ctctgcaggc   1500
tgcacctggg attcagccac cttcgttcct tttactgctg agtgtccatc acgtgctgct   1560
catgcagaag tgctcaagtt cgctgtaaac gtagttttca tttctcccgg gtggagacct   1620
ccataagtag gtaggttggt ggaatgtttc actgcatgag agtctgccag gaagttttgc   1680
agtgtggtcc cgtcttgttc ttcgcgcaga gggtgatagc tctgctgact cccagccctc   1740
acaggctcta gggattgagc ctgtttctgt ggaacgcctt ccatggtctg cgaggtgcac   1800
agaggggtct caaaaagctt ccaggttgca tcttcccatg gactgatgct gagcgtgttc   1860
tcatctccca tccggatgtt ttctttggtg gagtatcttt tcagatctct tgccttttta   1920
tttttatttg tttatatata tattttgaga cggaattttg ctctttcact taggttggag   1980
tgcaacggcg cgatcttggc tcactgcaac ctccccccac ccacctcact ttgggttcaa   2040
gcgattctcc tgcctcagcc tcccgagtag ctgggactac aggcgcccgc caccatgccc   2100
ggctaatttt tgtattttga gaagagatag ggtttcacca tgttggccag gctggtctcg   2160
aactcctgac ctcaggtgat ccacccgcct cggcctccca aaatgcgagg atcacaggcg   2220
tgagatgcca cacctggcct ctttttattt ttaatggagt ggcttgtttt cttattactc   2280
agtcttggga gttcctcatg gatgctggat ttcagtctcg tctcaggtgt atgcgttttg   2340
tagatgtttt ctgtagggac cagccccaca gggttggtga gtttctccct gtgtgctgag   2400
atgagagggc atagaaataa ggacacaaga aaaagacata aaagaaaaga cagctgggcc   2460
tggggaccac taccaccaag acgtggagac cggtagtggc cccgaatgtc tggctgtgct   2520
gatatttatt ggatacaaag caaaagggac agggtaaaga gtgtgagtca tctccaatga   2580
```

-continued

```
taggtaaggt gacgtgagtc acgtgtccac cggatggggg gcccttccct gtttggcagc   2640
caaggcggag agagagagag agagacagct tacatcatta tttctgcata tcagagactt   2700
ttagtacttt cactaattga ctactgctat ctagaaggca gagccaggtg tacaggatgg   2760
aacatgaagg cggactacga gcgtgaccac tgaagcacag catcacaggg agacggttag   2820
gcctctggat aactgcgggc aggtctgact gatgtcaggc cctccacagg aggtggagga   2880
gtagagtcct ctctaagctc ccccggggga aagggagact ccctttccct gtctgctaag   2940
tagcaggtgt tttcccttga cactgacgct actgctagat cacggtccgc ttggcaaccg   3000
gtgtcttccc agacgctggc gtcaccacta gaccaaggag ccctctggtg gccctgtccg   3060
gcgtaacaga aggctcgcac tcttgtcttc tggtcacttc tcactatgtc ccctcagctc   3120
ctatctctgt atggcctggt ttttcctagg ttataattgt agagcaagga ttattataat   3180
attggaataa agagtaattg ctacaagcta atgattaata atattcatat ataatcatgt   3240
ctatgatcta gatctagtat aactcttgtt attttatata ttttattaaa ctggaacagc   3300
tcgtgccctc ggtctcttgc ttcggcatct gggtggcttg ctgaccacag ttttcctgct   3360
gtatctaact gctggcttag gtgaacctgt caggggcgtg gctgggaact ggaacctcct   3420
gaagaccagt ggaggccaca agcagaagcc ctcggctcct tcccttcccc gatgctgggg   3480
gccaagggtc tttctctgac cctgtccccc cctcacgtta ccagtggagg gtgtccaggt   3540
tcttggcatt ttgaacaaag aattggacaa aacacacaaa caaagcaagg aaagaatgaa   3600
gcaacaaaag cagaaattta ttgaaaatga aagcactctt tacagggtgg gagcgggctg   3660
agcaagcagc tcaagggccc cggttacaga attttctggt gtttcaatat cctctagcgg   3720
tttaccattg gttacttggt gtatgcccta tgtaaatgaa gaggatgaag tcaaagtcat   3780
tttctcggct gagcatactg tcacgcctgt aatcccagta ctttgggagg ctgaggtggg   3840
tgtatcacct gaggtcggga gttcaagacc agcctgatga acatggagaa accccgtctc   3900
tactaaaaat acaaaattag ctgggtgtgg tggcgggtgc ctgtaatccc agatagtcag   3960
gaggctgagg caggaaaatc gcttaaaccc gggaggcaga ggctgcagag agccaaggag   4020
tgcaccactg cactccagcc tgggcaacaa gagcaaaact ccatctcaaa aaacaaacaa   4080
acaaaacgaa gtcatgtact cggtatgagc cctacgtaaa cggagaggat ggagtgaagg   4140
tacaaagcca ttcacattcc cgtcatcgtt agtgtttcca gttgatttgg ttctaggatg   4200
cccttgggct ccctgcgtcc aggccctctt ctcctgcctc actctcactc cagaggactg   4260
gcagtgctgg cctccctggc aggactcccg cccctgacca gaggggtctg ggcgtgctcc   4320
gaggccacct gctgctcctt gcccagtgtc cctgggtgct ctgtggggac acagagaggt   4380
cacttgggag gttcctgcct ctgccagact gcggcgcctt cctggcgtca ttgccccctg   4440
cacgcttata caaccagtga taaggcggta tccaatgccg taatcctccc cagggccagc   4500
ccagccctgt ccggtcccgt ccggtccctg gcctgcttgc tgggagccca gctgggggct   4560
gcatcggggg tggtgggggt ctggagtgag ggtgcccag gcctctctca cagtgtgggg   4620
gcacaagctc tgccctggac actctgccag tgtgacccta ccccccatgt tgggggtgag   4680
agaagggggc tttctgggtg gccagatccc aggagagggg gcctagccag accaacccca   4740
gcccagctct ctgcagctgt accccaaagg ccctggccca gcccagccag acagagtgtg   4800
gacagagggg cttgggtgcg agtccaggca aggcaggaca agtctctgct gtggcttggc   4860
agtggccccg tgactggtga catagtctgg caggcctagg ggacaaatcc tcagcccggg   4920
tgcatcaggc cagagcctgg ctgtctggag ccctccagga aatgaccccc cgggctgggg   4980
```

-continued

```
gacatccgag tgattgtgcc aaacaatgga caagggggcc ggagtctcag agccgaagtg   5040
ccttccgctt ccatctgctc cgcccaggag caggtgcacc caggtggtgg cctgggctat   5100
aaagctggcc ccctggggct tggggactca gcaccagggg ctggagggca ggggagggga   5160
tgatgtcatt cctgctcggc gcaatcctga ccctgctctg ggcgcccacg gctcaggctg   5220
aggttctgct gcagcctgac ttcaatgctg aaaaggtacc aggggcctct gctgtcctgt   5280
ggtgggtggg agctgggccc ctgccagaga caacgtgata attgtgacaa ctgcctttcc   5340
tggggcgctt gctctgtgcc cggccaggca cgtgctatag acccactctg cgcttaatcc   5400
taaaccaacc tgtgaatgga tcattactgc acccacttca cagctgggaa ctgaggctca   5460
cagttgcact gtgacctacc caagatgagt tcctgtccac ctgggctcag ctcacaccca   5520
agagatggcc actccgagac cccttgctgt gtgacttctg agttgtcccc tgggtccctg   5580
ggcaaggagg gccctgctgc tggctgtcct ggcctgcggg tgactaagcc cccggcagtt   5640
ctcaggcctc tggtacgtgg tctccatggc atctgactgc agggtcttcc tgggcaagaa   5700
ggaccacctg tccatgtcca ccagggccat caggcccaca gaggagggcg gcctccacgt   5760
ccacatggag ttcccggggt gagttacttg ggctgggctg cctgggctgg gctggggagc   5820
tgaggtagct gggtgccatg agtgagccgg ctgtgcaccc ccagggcgga cggctgtaac   5880
caggtggatg ccgagtacct gaaggtgggc tccgagggac acttcagagt cccgggtagg   5940
tcctgcctcc tctgccttca ggggtgctgg atgccgcttc tctgggggtg acgtggggct   6000
gactttccac ccgggcccaa gctgtccatc ccagtctcca gccccctgac cgccctcccc   6060
gcccctcctc tgtcttcggg gaacaggctc acagcccagc agcaggggca ggcatgggtg   6120
gggtcggtgc ccgggcccat ccacttctcc agcctgaaaa ggccgcctgc ctctccgcag   6180
ccttgggcta cctggacgtg cgcatcgtgg acacagacta cagctccttc gccgtccttt   6240
acatctacaa ggagctggag ggggcgctca gcaccatggt gcagctctac agtgagtgcc   6300
tgtcccacct ccccgcactg gcccctcccc aacttcccac aggccccgcc ccccgttctg   6360
cctacccccg ccccgcccgc ctgccgcccc gcgcctcctc acaggccccg ccctcacccc   6420
tccgcccccc gccttttagg ccgagtttag gctccgcctc ctcatccccg ggcccgcccc   6480
ttctggtgct gccccatgcc ctctcctgct gtgacccttc gcacacactc ctggcctggc   6540
caggaccggg tggggtggga gctgggcccg ccgtgctttg gatgtggagg aggttggctt   6600
gggggagggt cccgcggtgc atgctcctct ctggcctcct gagagtggtg ccccgccctt   6660
ccctgcctgg cctcgctgcc tgagttctgg ggctggggct gaggttcttt tttttttttt   6720
ttttttaat atggagtctc actctgtcgc ccaggctgga gtgcagtggc gcgatctcgg   6780
ctcactgcaa cctccgactc cccagttcaa gcaattctcc tgcctcagcc ccccgataag   6840
ctgggactac aggcgcccat caccatgccc gtatttgtat ttgtaaaaat ataaataatt   6900
ttttgtattt ttagtagaga cggggtttca ccgtgttagc caggatggtc tcgatctcct   6960
gacctcgtga tccgtccgcc tcggcctccc caaagtgctg ggattccagg cgtgagccac   7020
cgcgccggct ggggctcagg ttctttaact cctggggact ccccgattgg agccgacaga   7080
gtgaggctgg aggcttccgg gctgcaggga aagaggctca aggggtagtg gggcccagga   7140
ggacagccag accaccccaa cctcccagac atcttggtgt gaattgggga agggggcccc   7200
aagtttcctt cagccaggca ggagctttat gccgcgcaca acctgcccaa cccagggtgg   7260
cggccttgct gtcagccctc aggctggtgg agtgaggcca ggagaccccg tgctgcactc   7320
ctgtgagctg ctgagttcac agtgacctct gctctgccca ggccggaccc aggatgtgag   7380
```

-continued

```
tccccaggct ctgaaggcct tccaggactt ctacccgacc ctggggctcc ccgaggacat   7440
gatggtcatg ctgccccagt caggtaccct ggcaagcccc gcccgcccca tgccccccag   7500
cctctccctc ccttcccatg agcccaccct tccttcccct cacagcacag gcagtgtgcg   7560
ggcagcaggt ggtcttctct tccaggggtg ggctggcagc ccctgcagcc cctaccccac   7620
ctcccccaga acagactacg ggagaggctt tgggcagcgc tgggagggaa gctctgggct   7680
ccactctctg gggatggtgg agctgtccag tggcccttgg cacccagggg ttgggggctg   7740
cgggaagcga gggcggtcct ggccgtcagc atctcacgga tgtcttcctc cccacagatg   7800
catgcaaccc tgagagcaag gaggcgccct gacacctccg gagccccacc cccgcccttc   7860
ccaggtgggt tctccaggcc ctgcagggga tgccctggtt gcctctcccc tccctatcgc   7920
agcttgacat ctggttctgt ctgccccatg cctgccccgc tgttctgcct ggcgacccca   7980
tgcttcaggc ctcagcttag acattacctc ttccaggaag cctcccttga tttcctaagg   8040
tacccatcac agagtaccac aaatggggcg acttaaaaca gcagaagttt ggccgggtgc   8100
agtggctcat gcctatcatc ccagcacttt gggaggccga ggcaggcggg tcacctgagg   8160
ttgggagttc gagaccagcc tgaccaacat ggagaaaccc cgtctctact aaaaatacaa   8220
aacttagctg ggcgtggtgg tgcacacctg taatctcagc tacttgtgag gctgaggcag   8280
gagaatcgcc tgaacccagg aggcggaggt tgcggtgagc cgagattgca ccattacagt   8340
ccagcctggg tgacaagaga gaaactccat ctcaaaacaa acagacaaaa ccagcagacg   8400
tttatctctc ccagttctgg aggccagaag tccaaaatca agacgtccac agggctggtt   8460
cctctggaag ctctgaagga gactccctcc cacaccgccc ccccagctcc cacggctgcc   8520
gcttgtcctg ggcatttctt ggcctgtgga agcatcagcc ctgtctccgc ctccgtcctc   8580
ccacagccac cttccttctg tgcatctgtg tccaaactgc cccctagtgt ctgtgctgcc   8640
gaagcgagtg ccccacggcc ctcttcttag gagcatgcct gtgcttggat tcagggccca   8700
ctgtaaatgc aggatgatct aatctccaga ttctaaacta gtggtatctg caaagaccgt   8760
ttccaaataa ggccacgttc ggaggttcca ggtgggcctg aagttttggg gacacgattc   8820
aatccacagc tctgtgtccc cgctgtatcc acacagcccc tggctccctc cccagggcag   8880
ggtcctgcct tggaattgtg ggagccttgt cttctccccc agggcccagg agggcagacc   8940
acagccttcg cgcgcagtgc ccctcacagg agccacgtgc gggcggggtc ttgcggagat   9000
ccccccctaa accagacgcc gggagaccgc tgggtccctc gccggggctc accgccaaga   9060
atttgggcac agccacacgt cacgtgtctg acgtgacagt caccggcgtc tggagggaca   9120
ctggcccttc ctggcatggc gggaggaggt gggcggctct gaggcggggc tgtttctcct   9180
gcgtttctgc cgtgctgctg ttgcgtttcc tgcatctctg ctcctctcca tgagcttcgc   9240
ctccactccc aggaccctct ccctggagac tcgccgtcct gcctggggac actggggctg   9300
ttcagctttg cacaagtctg caccagcgtc tccctgcaca accccgctgg gttgggaaac   9360
atgggggggca acaccaaatc gcccttgtcc agaaggttct gtgggcagaa catgtagccc   9420
catcccgcca tgatcttgaa gaagcagctt tcggggtaga gtgccccgcc tgggccacca   9480
cgcgtgaccg tggaggctgt gggttctgtg gtggcttcat ggacattccg gggcttttct   9540
tgccatgcag ccccccttcac cgaggaccag gcagaggcca tggctcactg ccactcagcc   9600
agggactggg gcatggcact gggtcctccc gcgccgggga aggtggggaa gtgctggagc   9660
cagggatggc ctctggggca gcctctcgcc tggggcctgt ggggcagcag tggtagctgg   9720
tgtgtgtttc caggtttgca ggagttttgg gagcagaatg agctctccct ggcctgtcag   9780
```

tggtggcttt ggaagagtga tgcccagctt gtggggagca ggaagggcgt ttgtcgcggg 9840
agtgggtgat ggagtaggca tgcgttttct acgcaggtgg agccaaagca gcaggcgcct 9900
ttgcccctgg agtcaagacc cacagccctc ggggaccacc tggagtctct ccatcctcca 9960
ccccccgcct gtgggatgcc ttgtgggacg tctctttcta ttcaataaac agatgctgca 10020
gcctcatggc cctcacctct ttggacatgc cctgggggag ggcaatgcgg gcccctgact 10080
gaccccagca ctgctgggga gactgaggca gggaggcaag tgtgagaagg ccctggccgg 10140
gtgagcaggc cctggggtga gagggcaggg ggcaggggag aggggccctg ggaaggggca 10200
gggggcaggg gtgaagggcc ctgggtgagg gggcagggga caagggtgag gggccctggg 10260
tgaagaggca ggggacaggt gtgaggggcc ctggggaggg gcaggaggca gcagccactc 10320
ttggcctgtg tgggggctgc acccacagga agaatggagc atcctggccc agtccctatg 10380
ggtctgcagt gctgtgggga actgggcacc ctgtgaagac ggcccggcca ctggggctgt 10440
gctgggcaca caggccccgg tgctggggcg gggagctggg ggagctgcag gaggccgggg 10500
agttaggccc acttgggttt tgcccctcac cactgatatg atcgtgggca cctggtttac 10560
acccctggaa atgggtcacc gttgtggcca ggggactgcc agccagcctg agcgctccac 10620
agcagaccca cagacatagg tagctacccc gcgtactcct cgtttcaaag atcaggaaac 10680
tggcctggcg cggtggctca cacctgtaat cccagcactt tgggaggccg aggcgggtgg 10740
atcacttgag gccaggagtt tgagaccagc ctggccaaca tggcaaaacc ccgtctctac 10800
taaaaataca agacttaacc gggcgtggtg gcgcacacct gtagtcccag ctactcagga 10860
ggctgaggca ggagaatcgc ttgaacccag gaggcagagg ctgcagtgag ctgagattgt 10920
gccactgcac tccagcccgg gcgatggagc aagactctgt ctcagaaaaa aaaaaaaaaa 10980
aagaaaaaaa aatcaagaaa ccgaggcaca gaagggttgg gtaacttatc caaggctgca 11040
cagccaggaa gaggccaggc aggctgcaag cctgggtgat caggctccag ggccgggctc 11100
cacactgccc ccgggtggtg atgcctggtg cagcagaggc cctccccact gtcactgtca 11160
ctctggtcgc tggcgctgtg cctccggcct ccggagctct gactgcccac tgcgtctggc 11220
acacatttca aagggccagg cgtggggtgg cacaggaaag tgctggaggc tctggtccgt 11280
tgcccatcag tgcccacagc cctcgcagcg caggccagaa cgagcccaaa aaaacaagtg 11340
tcatgtgggg tgggggtcac cgagccccag gtggtgtggg tggagctcct cttcctctca 11400
ggctccgaga cggccccagc agcgtccacc gctgtccata cgccaggagg gtggctgggc 11460
aggctgctgt ctaggccagg ctaacccctg cggtgggcgt gggtgtcacc agggccgatg 11520
gcgcttgtgc agaaacccac gtctctgagc tgccagcagc caagctgtcc tgatgacatt 11580
cccgggtggg cgcacaagcc tgcactgtcc gtatagaatc ggcccaggct gtgcagcagg 11640
ggaacccgga gcccggaccc cgccacggag gccaggctgc cgtgcaccat cctgggtgtc 11700
ctcgtggtgc tccgggcgca ggtggcagca gccatggagg agctggaccg gcagaaggtg 11760
gcttctcctt cttagttcgt ggggctcctc ctacaccccc aacccctcag gctcagggaa 11820
ggaggcctct cccggtgtgg ggagctcgtg gggacgctgg tgcccggcta gacacttcct 11880
gttagcggca ttttcttctc cgctgagtct gtgccggctg ctgggccaga ggcacattag 11940
caggcccaga gaaggtagat gccggagacg aagattcttt cctcccgaaa atggtagggt 12000
ttttaaaagt ctcagcggaa gtcccggctc tgggccggtt gctgagggca ggaggcccat 12060
cccctggcgt ggttggcagg ctggcgagct gcgctacccg agccacctgt tctctggcgt 12120
ttctcactcc gccgcgccct gcgggctttc ttttccaggc ccctgctcct gggtcctgcc 12180

-continued

```
tccgaggtca ggcagggcct gtggttcctc ccgacatgtc gcagaagccc cagggactgt  12240
tccgcagctc tagatggccc agtggggagg ggctgccctg tgggcattgc tgtctgatgg  12300
cctgaaggca ccgcttggag ggacacatgc ctggggacag tgggctcaca gatgtcttgc  12360
tgctttgcca ccgagcctca cagccatctg ctgacctctc agagcccagc aggcccctgc  12420
ccgggggttc gtggaatgcc cctgggggtc tcagacccac tgctcagctc ttggccaggc  12480
tccgtatctc tctagattgg aggattctgg agggaagtcg gtgtggcctc cgatcaaagc  12540
ctggtgctga cggccccgaa gcgggtggag ggcttgttcc tcaccttgag cgggagtaac  12600
ctgaccgtga aggttgcata taacaggtaa gaggcctggg ggctgctgga gaggaagagg  12660
catgcatggc cggggactgg gcgtgggttg ctgcacccgc tgcagcgtgg ggtctgggct  12720
gagtgccgtc ccgctggtgg gccagcactc ccggtgcccg tctgcctgag ccctcgaccc  12780
ccaggctcct ggatctgcat tttatcccaa atataagcat agtgttttaa tgaagccccg  12840
tgaacttaga aggaaggaaa aggggtgtgg gacaggtgac tggctggagg gaacagaatc  12900
cccaggggaa ggccccacct ggcacattcc ccgcctcatc ctgctccagg ccctgggata  12960
ctccacagtg ctgcctgtgc ccttcctaaa gacacagccc cactccggga aggagcccag  13020
caggcgggac acaggctagc attttaccga tgggcacttt gctgcctttc agctcaggaa  13080
gctgtgagat agagaagatc gtgggctcag aaatagacag tacgggaaaa ttcgcttttc  13140
ctggtaagtg cagttgccct gtgatggcag gtggaacccg gctgtgcaca cagctaggcc  13200
ttattgttcc ccatgctgtt ccctgcactg ttccccatgc tgttccctgc actgttctct  13260
gtgctgttcc ctgcactgtt ccccatgctg ttccctgaac tattccctgt gctgttcccc  13320
atgttgttcc ctgcactgct ccctgcactg ttccacatgc tgtttcctgc actattcccc  13380
atgctgttcc ctgcactttt ctctgcgcca ttccccatgc gttccctgca ctgttccctg  13440
cactgttccc catgctgttc cctgcgctgt tccccatgct gttccctgca ctgttcccca  13500
tgctgttccc tgcgctgttc cccatgctgt tccctgcgct gttccccatg ctgttccctg  13560
cactgttccc catgctgttc cctgcaatgc tccctgcact gttccccgca ctgctccctg  13620
cactgttccc catgctgttt cctgcactat tccccatgct gttccctgca cttttctctg  13680
tgccgttccc catgcattcc ctgcactgtt ccctgcactg ttccccatgc tgttccctgc  13740
aatgctccct gcactgttcc ccgcactgct ccctgcacta ttccccatgc tgttccctgc  13800
acttttctct gtgccgttcc ccatgcattc cctgcactgt tccctgcact gttccccatg  13860
ctgttccctg cactgttccc catgctgttt cctgcaccgt tccccatgct gttccctgca  13920
gggttccctg cactgttccc catgctgttc cctgcacatt tcatgcccca gaccttccca  13980
ttctcccacc aacacactgg atcatccttc aaaagcttct gtagtgtctc caaccactca  14040
agtgctggga ctgggtgggg gcaggatgga gttagaccct gcagaccctg gccttcgagg  14100
tccgtccccc tcagacgtct cccccaacgc catggccggc tcttgaaggc cacagagaga  14160
tccacgtgct ggacaccgac tacgagggct acgccatcct gcgggtgtcc ctgatgtggc  14220
ggggcaggaa ctttcgcgtc ctcaagtact ttagtaagct tggccctggg gggctctgcc  14280
cagctgctgc tctcccaggg actgcccgcc cagccccccct gtgccccaca gctcggagcc  14340
ttgaggacaa ggaccggctg gggttctgga agtttcggga gctgacagca gacactggtc  14400
tctacctggc ggcccggcct ggtgagccca ggggccttgg ggtggaggct gggctgggcc  14460
ctgtgggctg actctgcagc tcctcatgct ggcctatcct gcagggcggt gtgccgagct  14520
cctgaaggag gtgagcttga cccccgaccc tggcctgtgc tgaagttccc gggcccctgg  14580
```

-continued

```
cccagtccct ggccctgtca ggagcccccg tggctccgcc tcccggccct gggctgggcc  14640
ttctcacccc ttcctgtgaa caggacacca aacaccactg gtgggcagct ccagagatga  14700
gtctgtctcc tggtttggaa agagctggaa cctccagggt ggtgacccta ggctgccagg  14760
cagggaccct gggaggctgg ggtcacgggg tgcagagctg ggtggggcag gggagcagaa  14820
atggcgcctt ttcttcggtg ttccgtgcag gactgccggc tgcttctgcc cccgaaggtc  14880
ccgtcggcgg cggggcacag atcctgcggg cgctgcctca gggctcccat gttgggcact  14940
gcgagaaccc agtgtctccc tcacctcgct ttgtcttggc cctagaggct gggcctgtta  15000
ccccatttg cagattgaga aggcgctcag ggagctgggt gctttgcgca aaaccaggca  15060
gcgaggacag aagtcccgcc gtgtggccct catcgaagcc ccgtggggcc tccagagacc  15120
acacgggcct gagcccctgc acttctgtgt cgcaggagct gatttaatgg agttcctgcc  15180
tcagaccaca aggttcggag cgcccgccca cccctgcccc tcctgggcac cctgcccacc  15240
aggtcacctg cacctgctct gaataaactg tgaagtcaag ccactgcctg gtgtgtcctt  15300
ccggagggcc gatgggtgac aggtgtgggg ggactcaccc gccccaggtc tggcaacagg  15360
aggtgtgttt tccgtggtta ctggacaaac agtgcggctc acgtgcaagg cagcaacccc  15420
tgccctcccg ccctgctagg gtcgtggtca ggctgcccca gggtatagac cagagacaga  15480
aacagggctc ctggtggagt ctcagcaggt ctgtcaaacg catggaggcc acacccctcc  15540
tgcctgcatc ctccatggct ccccactgcc cagggctcca ggctcacggc ccgtgctgaa  15600
ggccctaccc gatgggcccc gcttccggcc tccctggacc cccagctgcc cagccctgct  15660
cagtgtccgc ttccacagtg ggctgtcacc ccgtggcctc ggctgccacc agccgactgc  15720
atcactttct cctcccgcct ggcctgggac acgggaaggg caaggaaagt gacagtgtca  15780
gcccagaggt tctgcgccca ggcccctggg gaatcagccg gtccccacat atgcaggtga  15840
gacaacccag gcttatgagg gtggctgcct cgtcggggcg gcggaaaatg atacctgagg  15900
tcgagtggtg ccgggagctc tgggggaaca gcccgagtag ggggacctcg ccagccccca  15960
gcacggccgg gacactggaa aggccctgct aggaacaagg gctgcaccct agatgcgcct  16020
caaatccaga actgtgcccc cgagacccac aggagggaca tgtagaggct gcattctgac  16080
aagttagggg ctcctgggaa acagccgtga ctttgcgcag ctgtgcctgg ccgaagccca  16140
cgggttcaag gagcttcgcc tggacttgga tttcctgctg gaggggctgt cactctcgct  16200
gtcagctcag gctcccgtga caaaataccc cagactgggc accttaaaca acagaactgt  16260
atttcctcac cgttctggag ggtggaagtc caagattaag gtgccggaaa gtgcagtttc  16320
tggtgagggc ttcctgccca ttcgcagaag gcagcccctc gctgtgtcct cacctggcag  16380
ggagcgctct ctgggtgcct ctttttctcc taataaggat atcagcctgt taaattaggg  16440
ccactccctt tgacctcact taatctcgat tgtctcctaa gagtcccatc tcctgaaaca  16500
gtgaccatgg gatctggggc ttcaacgcag gaattttggg agggcagaat tcatcccaga  16560
acaaaagtca gtgctgttta gagggtgaca gtagatgcag ggctgccgtc atcaacaacg  16620
tcctgcccaa aagtcactgg acgtccaaag acacagaaaa gtatgaccta tgttaaaaaa  16680
aaaaagaaaa aaaaagttac taaaaactga caccgagaag acccaaagtt gtattcagaa  16740
gataaaggtc taaaacagcc attataagta gttaaaagaa aagcaagata tactctaagg  16800
aaagaaatag tgacacaata gcattaaagg actaactaat tgataaagaa ttaaggagtg  16860
aacgtaggag atcagatcag gaaatcaaga gagaaatgga aactataaaa aagaaaaaat  16920
tatggaactg aaaagtacaa taaatgaaaa atttactgga aagactaata ggagttggcc  16980
```

-continued

```
atggcaaaaa taatgtccat gaatttgagc acaaatcaat gtaaattatc cagtctgagg  17040
aacagagaag aaaatggttg atagcacctc aaagatatgt ggggcaagat aaagaatgta  17100
aactagcctg agaaagagaa gagagtgaga atacatgaag aaacagtggc caaaataacc  17160
caaacttgat ggaaacatca acttagccca gaggctcaga gaaacccagg caggatgaaa  17220
aagaaagcct cacaaaaatc acacctgggg acattatagt caaagcactg ccaaccaatg  17280
atttggataa aaatttaaag ggatctgtgg attaaagaca gggcacatcc aggtttggtg  17340
gctcacgtct gtaatcccag cactttggga ggctgaggca ggaagatcac ttgaggtcag  17400
aagtttgaga ccagcttagg caacatagtg agactttgtc tctctttaag aacaaacaaa  17460
aaagacaggg catgatatag tttggctctg tgtccccacc caaatctcat gtggcattat  17520
tgcaatgccc aatgttggag gtagggcttg gttggaggtg attggatcat ggaggcagat  17580
ttccccttgc tggtcttgtg acagtgagtg agttctcagg agatctggtt gtttaaaagt  17640
gtgtagcact tgccctttca ttctctctcc tgctggccat gtaaagatgt acctgcttcc  17700
ccttcacctt cagctatgat tgaaagtttc ctgaggcctc cacagctgtg attcctgtaa  17760
agcctgtgga accatgagtc aagtaaactt cttttcttca taaattaccc agtctcaggt  17820
agttcttcat agcaatgtga gaatggacta atacagggca taaacagggg gacacaatgg  17880
ctgtcttctc atgataaatg gaaaccagga gatgacaata ggccatcttt acattgatga  17940
aaaaaaaaat caacgcagag ctctttatct aggacaaata tccttcaaaa ctgagggtca  18000
aataaacata cttttcaaca aatggaagtt gagggaattt atctctagca cagcttcagt  18060
acaataaata aatgccaagg atgttcctta ggcagaagga aatgactctg gatggccact  18120
caggtctgca ggaagaagat ccgtgtgaca agtggggacc aagtgagccc actggaacct  18180
gcattccttg ccctccattt ggttacttaa ttatatcagc atggactcag cagttcctgt  18240
tttcttccat aggttacaat ttatgacaat catttctacc caatgggagt gccttcaaag  18300
tggcttcaga gtgttgttgg tacattccct gattccttga gcacattttt gctttttggc  18360
acaaaaaaca ttccaagttc ctcttgcatt ttctgtacac aggctttgaa taattcacca  18420
gagtcctggt tccttttcat atagaatggt gtgtggagaa accaagctct gagtgttggg  18480
tgtgctttta cttttactgg gtccgattgt atctaaacct tctcaacaca cagagcctgg  18540
actttccttc ctcctcttcc tccctccttc ttcttcccct ctcctgcctc cctctctctc  18600
tctccttctt cccttcccct cccatttctc cctccctctc tccctccttc ctctcctccc  18660
tgccctccct ccctcccttc cctccttcct cccctcctcc ctctctcctt ccctccctgc  18720
ctctccccat gtgtctacca aaattggagt tcacatggat atttccaatt ctaatcagac  18780
gccacagggt tcactttgat ctctcccctt tctatatgtc tatatttata attctctttt  18840
ccaacacaga gaaacccatt atccttgata tatttactca tttggtccct tctagagcac  18900
acggaaagta gtatcagaat tgctcaccca aaccactgtt agtcatgaac ctgcccatga  18960
gagcttagga tgtgtttaca gctctttctg ctgttagctt gagaatacag agaaaaacta  19020
ctgtgttcag aagttaccag gggcagtcct ttccccttca gtgtggctgt catttatcta  19080
taatgcaact atatcccatg tttggaattt gtttatttta cttttgagta taacagtata  19140
acataccaaa ttactttgat tccaaagtca aaactataca aaaacgttta ctcaaaaaag  19200
tctaacttca tccccccacc ctgttccagc tccccacccc agcagggaac tagtctcatt  19260
agactctgag gtttatcctt tgtttttgtt tgtttgtttg tttgtgtgtt tgtttgtttt  19320
tttgagacgg agtcttactc actctgtcac ccaggctgga gtgcagtggc gcaatctcgg  19380
```

-continued ctcactgcaa cctctgcctc ccgggttcaa gcgattctcc tgcctccgcc tcccgagtag 19440
ctgggattac aggcttgcgc caccaccacg cccggctaat tttgtactt ttactagaga 19500
tggggtttca ctaagttggc caggctggtc tcgaactcct gacctcaggt gatctgcccg 19560
cctcggcctc ccaaagtgct gggattatag gcatgagcca ccacacccgg ctgatgtagc 19620
gtgctgtttt gtggctgcct cgagaaccag gctccccgca gcccttaggg acactagtgg 19680
ggctggcagg tgtttccttc tcagaggcct ggcccagctg ctcggcttcc tcctttttgt 19740
atttttattt tattttagag atggggtctt gctccatcac ccaggctgga gaggagtggc 19800
acgatcacag ctcactgcag cctcaacctc ctgggctcaa gcaatcctcc tacctcagct 19860
tcctgagtag ctgggactac aggagcacgc caccatgtcc agctaatttt taaacttgct 19920
tgtagagacg aagtcttgct atgtcgccca ggctggtctc aaactcctgg actcaagtga 19980
tcctcccgcc tcagcctcct gaagtgctgg gattaccgcg agcagccacg gctccctcct 20040
gaaggctcca ggcctaagtg tcccgctccc ttgttctgtg gctcagcccc tgggcaactc 20100
ctgcttgcca tggctgtggc tggcacctcc gtggccccac tgcccggtca gtcttcgcag 20160
gcccagcccc cagtagctgt gtggtttctg ccttcctcct gcactctggt ggtcacaggc 20220
cctgctgcgt gggtacaggg caggtggcca gggctgcagc ataagctctg tgagtgcagg 20280
cggccctagg cactggagcc ttgttgcatg gacgtgctcc ttgcaccctt gttgatgaat 20340
gagcgaaggt gtgtgggagt gaatcccaga gggtgcaggc cacggcactg ggggaggacc 20400
ctcccggctg cctcccagtg ggcttcaggg gctcagatag accctgccga gcacctctgt 20460
cctctgctcc cggactgggg ctgcagagag ctctcaaggg gccttgggag gcacaagcag 20520
gccagggtcc cagggagggg aggcaggagg cagcagggcc ggatggtggg ctgcagaggt 20580
ggaaggaaca ggacagtctg ttctgggggt gctggctgtg ggggacagag gccaggccac 20640
aaagcagaat ggtgggtggg ccaggaggag gtgggagcct ttttcaaaag gctttcaggg 20700
actttttata tttaatgatt gaaacaaaag atatccaaaa ccgcagttcc tgagaaccac 20760
ttgttctcgc cctggttcct ctccttgggc ttgaccttgg cctcctgccg ggcctggcag 20820
cggacagcag tctccctgct tcccaggctg ggcgagggag agcgtgggtc cccaggaacg 20880
ggggaggtgg tgcggctggc tttaggatgc ccattctgga accttctggt ggaagaaagc 20940
aggggatcag tatagtatgg ttgatccaca cactccagac cctctcctgg ctgtgcagct 21000
ggtctgatct gggctcagag gctgccactg ctcagtgctc ccctgggtaa ttttgcagga 21060
ggccaggagg gttcctggca gttagtgcca cccacacgga gaaattcaga gccatataaa 21120
cgggtctcca gggcctggag ggactgcaca tcctgggctt gcggcgcagt gtagacctgg 21180
gaggatgggc ggcctgctgc tggctgcttt tctggctttg gtctcggtgc ccagggccca 21240
ggccgtgtgg ttgggaagac tggaccctga gcaggtacag tcctcctggg ggtggggaga 21300
gctggtcctc gggggccagc ccctccttta aggccacaca gcttctgggc cccccagggc 21360
tagcccagac cagcatgagc agtggggaat tagttgggcc agcccttggg gagtcccaca 21420
ggcaggagcc tcagggcagg aggggtggat gctggagggt tggaggctgg agggctggag 21480
aattggaggc tggagactgg aggttgcagg gctggagggt gtagggttgg agaactggag 21540
gctggagggc tggaggctgt agggctggag aactggaggc tggaggctgc tgggctggag 21600
gctggagggc tgtagaactg gaggctggag ggctggaggc tggagggctg cagaactgga 21660
ggctggaggg ctggagagct ggagactaga ggctgcaggg ctgcaggctg gaggttggaa 21720
ggctggaggg ctggagccta gaggctgtag ggctggaagg ctggaggctg gagggttgga 21780
ggtctggggg gttggaagct ggaggctgga gggctggaga actgaaggct agaggctgca 21840
aggctggaag gttggaggct ggagggcggg agggttggag actggaggct ggagggctgg 21900
atggttggag ggtggaggct ggaggctgca gggctggaag gctggaggct ggagggttgg 21960
aggctggagg ctggagggct ggatggttgg agggtggagg ctgaggctgg aggtttggag 22020
gctggaggct gaggctggag ggttggaggc tggaggctgg aggctggagg gctggcggcc 22080
ctaacgggag ccgcctcaat gcagcttctt gggccctggt acgtgcttgc ggtggcctcc 22140
cgggaaaagg gctttgccat ggagaaggac atgaagaacg tcgtgggggt ggtggtgacc 22200
ctcactccag aaaacaacct gcggacgctg tcctctcagc acgggtgagt gggcgggtcc 22260
tgccaggcct tcccgcaggc aggactgtgg ctcagccaca tcatgtactt tgcacatctg 22320
ctcccgggca ccgcggcctg gggcttccc acggcccctc tgcacccccg tcacttttcc 22380
cactgggctc tgtgcagagc caccagccct ctgcccagct actcacatct gtgtccctgg 22440
ggcctccagg tggcactccc accttcaata ccgcggcggg cactgctctg actatgctcc 22500
ttcatgcatc cctgtcctgg gtcatctggg ctgcaggctg tggtcagagc tggggaagcc 22560
tgtcctctca gcaggccttt ttcgggaatt ctgtttaaag gaggataatg cattcggacc 22620
taagaaccac tggttctttc ataacataaa tccccaaaca atatggtcat ggacgctgtt 22680
ggccagactg gccttgtggc ctcaggcagg cgcacccgac cacatgcatg gctggtggcg 22740
gcgtgcaggg gtcgggtggg ccaggctgtg gggcggccgt gctacacagg ggacacctac 22800
agggcagccg ggctgtgggg gtagccgtgc tggggcagga gtcggtgccc gcctcccttc 22860
acagaagagt ggcctgctgg gtggcgtggt gggtgtctac cccctggcag gctggcgaca 22920
gagcccaggc ctgaaccact gagccaggta cggggcccag agagaagaac ctgccctcct 22980
caccagcgtg ccttcccccct gcacctgcgc ctgcagggta tgggcagggg ccccactgca 23040
ccccccgggc caggcctggc ctcagggcga gctgggacca aggggctcca ggctgaggtg 23100
gcagctccca cgtggctttc ctagttcttc ttgctgttcc tcccgcatgg actcagcctc 23160
agtttccttc cttggcaaac accattgcac ctttgctggg ttttgctcac tctggggact 23220
gaccacttag ggagcgccgg ccccttcccc cgagtcgcag gcaaaccccc accccgcccc 23280
atccttcccc tgagtcgcag gcgaaccccc accccacccc atccttcccc tgagtcacgg 23340
gcgaaccccc accccgcccc atccttcccc tgagttgcgg gcgaaccccc accccgcccc 23400
atccttcccc tgagtcacgg gcgaaccccc accccacccc atctttcccc cgagtcgcgg 23460
gcgaacctcc cgtctgtcga gtctcctgtt gtgtcctcag cagcattcag cgttcctggt 23520
ggagatctgg cactgaggat ctctcaggaa gtgaatggga gtgtccgccc ctctcaggac 23580
tcccacgccg tccactctcc gagaacaggt ttccgggcat cggggcatct ggcagaagat 23640
ggaagctctg gcctcactgc tggctggcct ggcctggact cctgagctcc gtctcctctc 23700
accgggcccc ggggtcttga ccctgagtgg gtgacaggcc ccttcttttc caggctggga 23760
gggtgtgacc agagtgtcat ggacctgata aagcgaaact ccggatgggt gtttgagaat 23820
ccctgtgagt ctgacggcca cggcctcacc caggccgttc ttccctgcag catccccagg 23880
ccccctgcgg gcagggacgg agggctgact ccgctcccga gagccaggag gctacaggtt 23940
ctggtcttgg gattgctgcc catcctgagg gtgaagagaa gcccctggac agaggattgg 24000
aaccttgttc ccagcaggct cagacaccag tgaggtccag ccaaggtccc cataggtgca 24060
gagggcgagg ggcctgttta gtggctgtct acaggtacag ggctgggctg gtgtgaccca 24120
gccgctcctc gttcacacct gggacaggct ggggcagtgc tcgtctgtct gtccgtcagt 24180

-continued

```
gtctgaaagc cccttgatgc tggcaccagg tggggtcggg ggtgggggac aaagcttggg  24240
ggctctgggt gtgcttggag gggtctcctg gggagggggg ctctcacttg aattggcccc  24300
tctgtccctg tggccagcat cagctcagcg gcccctggat ggatacagca gctgccctcc  24360
cctgaggcgg ggggttttgt ttcctagcaa taggcgtgct ggagctctgg gtgctggcca  24420
ccaacttcag agactatgcc atcatcttca ctcagctgga gttcggggac gagcccttca  24480
acaccgtgga gctgtacagt aagtgtgctg tgcggggccc acgtagggag ctgtgtggtg  24540
cgtgggccgc tcggggccca cgttgggagc tgtgtggtgc gtgggccgct tgggggccgc  24600
gtggggagct gtgtggtgag tgggccgctc gggggccatg tggggagctg tgtggtgagt  24660
gggccgcttg gggccacatg gggagctgtg tggtgagtgg gccgctcggg ggccatgtgg  24720
ggagctgtgt ggtgggtggg ccgcacagga ccacatgcag gccaagttcc cccaccttga  24780
ggctcgctgc actggaggtg gctttggaag gaccggggcc agcatcccag ggcaggtggc  24840
ctccttcctg acccttccca gcccctcccc ggcccctccc cagctctcag aggttgcttc  24900
cccctgcact gccctggtgc ccccaggtct gacggagaca gccagccagg aggccatggg  24960
gctcttcacc aagtggagca ggagcctggg cttcctgtca cagtagcagg cccagctgca  25020
gaaggaccgt gagtgtccac cggagcagcc tcgggggagg cttggggcaa gttctggagc  25080
ccacagggcg tgatggggtg acagagaccc tggggttgat tctggcttct gcctgactca  25140
gtcgccctga aggagtcagg caggctgagg gggtcttcac ctgcccctgc ccaaagtcag  25200
gcctgggggt cttgtcccca cggcaggcga gtcttgtggg tggggccctg gggtgctggg  25260
gggctcagtc ctttttcaca gccagtcttg cctccccttc tagtcacctg tgctcacaag  25320
atccttctgg taagccgcca tcctgagcct caccctgggc tctcttgggg gaagggggtt  25380
ggggaggcca ccctacgcac agtgggtggg aggaccctct gcccaagccc acggggttca  25440
tggctccact gtctctaagg cagctgaggg tgtggaggag cctccatggt gggctgggcc  25500
ccctcacact cctcttggtt ttcagtgagt gctgcgtccc cagtagggat ggcgcccaca  25560
gggtcctgtg acctcggcca gtgtccaccc acctcgctca gcggctcccg gggcccagca  25620
ccagctcaga ataaagcgat tccacagcaa accaaggatg cttttgactg ggggccagcc  25680
ggggaattgc ggggaggatg gcgggggtcg tcaccaaggg ccaagccaca gaaccataga  25740
gccagctgca aagaagacgc gtgcccaacc cagtcccttg ccagagcccc tctgggtctt  25800
cagacaccca aactcaggcc cggctcaga ggcgggggct ggtcagagga cacagcctgg  25860
gaggaagcca gcagtgagct ccaccaggac cgcagctggg gtgccagagg ctccaaggac  25920
tgcccaggac aagagagagg tggctggtgg ggctcagagc agcccctgac tccccaggct  25980
caggcttctc tgggctgggg ttgtgtctct tgcctgggca ggggcaggga ccccagacac  26040
ctgagcctgc aggtcctcct gtgttctgat gggtgtgggg ggctgcgctg cctgccgtcc  26100
tgggagaagc acaggccatg gggtctcgg ggctggatgg ggggctgggg actgtgtgag  26160
gctcatgctg gagtgaggcg aggtgcacac agatgccttg acctgcaagg ctgggcatgc  26220
acacgcatgc acatgtgagc acacacccac acatgcacac acacacattc atgggcacgg  26280
gcacacagcc ccggcccgcc cttcggcacc tgctcaggtg cttggtgcca ggccctcaag  26340
aaggtggtgg gggctgtgtg tgtggctgcc gcgcagagct caccatgtcc acatctgccc  26400
cagaagggcc acgaccagcc ctttgcctgt cacctgggag gtctaggatg agggccaggg  26460
cttaatgagt ctcaggggca cacacagtga ccccaggccg ggcactgagg gcaggagggt  26520
cctggggcct cagaggggcc tctgtctgcc agggcagccc aggccagcag tgaccaccag  26580
```

gtggggcagt gccggcttcc ctggagtgtc tgggggtggt ccctgggcgg ggagagggta 26640
gcagagccca aggccacacc tgttgcctcc ctccgctccc tcccctccct cctctcccga 26700
cacaggctgg cggctccaga gaggtttaaa cactggcctt ggcggctgag ggaggagggt 26760
gaagatgagg caggggctgc tggtgctggc gctggtgctg gtgctggtgc tagtgctggc 26820
tgcagggtcc caggtgcagg agtggtaccc cagggagtcc cacgccctca actggaacaa 26880
ggtgagccat gtgccactgg tccctgagcc gggcgccggc tctggagctg gagcaggctc 26940
ctgcacagtc tcccggcagc cgcccaggag cagggctacc agcagttcca ggcacgggcg 27000
ctgcccacct ggcctctccc actgcagcct ccagcacagg ggccccgcaa gttgcagggc 27060
aaaggcaggg agcctcgagg gggttcgggg gcccaggggg gtcagggagg gccagggtgg 27120
aggggcccag agagctgtgg ccgaggaggt cgggagacgc ccagagtgca gagtgggtgt 27180
ggagcaagcg gggcatattc tgtagcggga gggcccgggc acctgctgag tgagccgtgg 27240
gagcagcact cattggcacg gcggtgccca gggcgctagg gttggcagca ggcagagttg 27300
ggggccgggg gccggcagga agggaagtgg ccgagcagta cccagccccc aggaggccat 27360
gtgggaagga gccggggcct ctgaggtagg gggcctccca cctgctggcg cccacagccc 27420
agccctttgc tgcctggggt ccctgaccag ccgggcacct gcttctctgc agccctgctc 27480
cagtggccag ggcttgagtg gccgggaccg aggcggcacc tgggcggagc tgggactccg 27540
gctcacagaa gggtcatttg tctcctgggt tctctagctg ggaacctcgg gggtggggac 27600
agcccccggt ggcagctcct gtccccgccc acacatccgc tgcgcagttt tcagggttct 27660
ggtacattct ggccactgcc actgatgccc agggattctt gccggccagg gacaagagga 27720
agctgggggc gtccgtggta aaggtgaaca aagtgggcca gctccgcgtg ctcctcgcct 27780
tcagacggtg agtgggcagc gccccccagg caagggtctc cccttccagg aggagggagc 27840
tgcctcgggg ctggaaagga gtctgggagg agcctgtctg tctggaagtt ccacaagaac 27900
cgtcccccca cttcctcccc ctaaactcag aggaagccac ctgcagcccc tgggacccca 27960
catgggtggg tgttgggagg aagctgcctg cagaccttgg gaccccacat gggtaggtgt 28020
tgggaggaag ccgcttgcag ctcctgggcc ccacacgggt gggtgttggg agtttctctc 28080
gtgccgtggg acaggcccca gtccgaattg gaaaatcctc aaaccacaga gcctcagatt 28140
gacacgagtt ggatagtgaa gcaaaaaact ggggacctgg ggccccaacc ttcccgggtc 28200
ccacgggagc aggggcggga ccgagacgtg tgggtggggc tcggtggctg gcaggcggga 28260
ggaggggttc cctggtctgc agcctgagcc cccgccttgg ccccaggttg aaggggtgcc 28320
agtcccagga ggtgatcctg aggaaagacg ggaagaagcc ggtgtttggg aacgcctgtg 28380
catacgcggc gggcccgagg gaaggacagg agggaggtgt gcttgggctc tgggccctgg 28440
aggagctgcg tgatatgcct ctgacccccc tgtgccttga gcaggcccct tgtccccgag 28500
agcacgtggc aggcaggcgt caggctggct gtgttcccag agcccacacg tcatgtgctg 28560
ggcggcctgg cccgggaggg gaggccccgg gagggcactc agtccctctg gacacctgca 28620
cctgggtggg ggctctgagg cctcgggcac caggggtcag ggctgtgggc gggcacagcc 28680
acgccatccg ggaaccagcg ggcatctctg ggcatctctt tcagtgaaag gggtgaaggc 28740
cttccacgtg ctgtccactg actacagcta cggcttggtc tacctccgcc tggggcgtgc 28800
aacccaaaac tacaagaacc tgctgctctt ccgtgagcag gcacagcgga tggcagagga 28860
tggtggaggg ggtgcagagg gaggcataga ggggcgctgg gcacaggggg ccgggcagga 28920
ggtgaggcgg gcagggagag tgggggttgg ggcggtggtc agggcagggg caatggaagc 28980

```
cgagaccaca gcagtcaggt cctggaggtc gctgaagcaa ggatagggga cgtcaggaag  29040

aggctgcaga gaaaggtggg ccatccaggg ggagcggagg ccaccaggat ggtggcgggt  29100

gcaggtgcaa cgttctgggt gagggacaca gtggggatga ggaggcgtgg gaggggtccc  29160

aggtaagggt ctgcccggga tggaggggtg tggaagtgac ccagtgtggg ttaagggcca  29220

caaacccaat tctagacacc aaccacttgg ggtacacgga aaggagtggc cctcccggtt  29280

ggaacgggta gaggggaggt ggggtcctgg ggtctcagtc gaggcagggc acgctcaggg  29340

tgcagcaagc tggggcacag ctgaggggct ggctggaggg gactctgcag gcagagaggg  29400

ttccccaggt gacagcgtgg tgaccctggc ttcccgagcc tggctgcctc gtaagtgggg  29460

aggggcccag cggccgctgt cctcccctgg ccaacccctg cttcacgcct aagctctgag  29520

gacatttcag cagctcctgg ggtagggatg ggggtcaggg tgcagaccct aaaatggcca  29580

gagctggagt ctctgatgtg atcctgatct caacctcaga taggcagaat gtttcgagct  29640

tccagagtct gaaggaattc atggacgctt gtgacattct ggggctctcc aaggccgccg  29700

tcatcctccc gaaagacggt aagctgtgcc ctcagccctt tgccctcctg gccctacctg  29760

cccgtcccat tggggagctg attcattggg ggaaggagag atgaaaggat ccatttgaaa  29820

ggtgccattt gaaagatccg cccaaacgtg cctcccacct cctgccgccc ctgagaatcg  29880

gggcttggcc tggcaggcct ggcaccgaca gcgagaggcg tccggagcag atgctgcatc  29940

cgaccaggcg atgccgtggc tgtggctgca ggatcggggg ctgcatggct gtgttctcgt  30000

ggtgcccaag acgagcacgc atggaaccag ggagcggccg ggggagacgt gttcacggct  30060

catgtgtctc ctccaagcag ccagcccaca tgtggctgtt ttcctctccc acagcgtccc  30120

gtacacacac catcctgcca tgagagccag cgtcctctgc tcttcccttt cgacgcgtgg  30180

tcctcccaga cccgaggagc gttgttccag atgtcaagtg gagaccacgg cttgttgaga  30240

ggtgtttggt gactctaggt cattgacagt gtgaaaatca agtggctcaa gggatccttt  30300

atgatcacag aaagatgggg gaaggaggat acaggctgac cgggtggcga gatgtcagcc  30360

aggccccttc cccactgtct tctggagcac actgcaggct gctgctattc cctgtctgct  30420

gtgaaacaga ccacaggccg gcccaacgca gtcctcgccg tgtgccttgc ctctgccctc  30480

cacgccgccg ccaccctccg cgttccttta catcctgcac tttctcagga agccgttcgc  30540

atatccaccc aacatggagg agcccccatg acgtgccagg cagcgtgctg gcccctgcgg  30600

ctgcgttagg gaacagaatc ggcaaacgca gtcccagagt tgatgcctga tcaggagaag  30660

ccaacttcag cagtgtggtc acctggatac tcgagtatag accctagatc acctggatac  30720

tcgagtatag accctagaag tgtatctagg cgcggccagg gccccacaac agcaggtctg  30780

actcattcca tccagggcag catcagggag agcttcctgg gggaagtggc atttgggctg  30840

acctgggaag ggtggtgggt gttaa                                        30865
```

```
<210> SEQ ID NO 3
<211> LENGTH: 531
<212> TYPE: DNA
<213> ORGANISM: Homo sapiens
<220> FEATURE:
<221> NAME/KEY: CDS
<222> LOCATION: (1)..(531)

<400> SEQUENCE: 3

atg atg tca ttc ctg ctc ggc gca atc ctg acc ctg ctc tgg gcg ccc       48
Met Met Ser Phe Leu Leu Gly Ala Ile Leu Thr Leu Leu Trp Ala Pro
1               5                   10                  15

acg gct cag gct gag gtt ctg ctg cag cct gac ttc aat gct gaa aag       96
```

```
Thr Ala Gln Ala Glu Val Leu Leu Gln Pro Asp Phe Asn Ala Glu Lys
            20                  25                  30

att gga gga ttc tgg agg gaa gtc ggt gtg gcc tcc gat caa agc ctg      144
Ile Gly Gly Phe Trp Arg Glu Val Gly Val Ala Ser Asp Gln Ser Leu
        35                  40                  45

gtg ctg acg gcc ccg aag cgg gtg gag ggc ttg ttc ctc acc ttg agc      192
Val Leu Thr Ala Pro Lys Arg Val Glu Gly Leu Phe Leu Thr Leu Ser
    50                  55                  60

ggg agt aac ctg acc gtg aag gtt gca tat aac agc tca gga agc tgt      240
Gly Ser Asn Leu Thr Val Lys Val Ala Tyr Asn Ser Ser Gly Ser Cys
65                  70                  75                  80

gag ata gag aag atc gtg ggc tca gaa ata gac agt acg gga aaa ttc      288
Glu Ile Glu Lys Ile Val Gly Ser Glu Ile Asp Ser Thr Gly Lys Phe
                85                  90                  95

gct ttt cct ggc cac aga gag atc cac gtg ctg gac acc gac tac gag      336
Ala Phe Pro Gly His Arg Glu Ile His Val Leu Asp Thr Asp Tyr Glu
            100                 105                 110

ggc tac gcc atc ctg cgg gtg tcc ctg atg tgg cgg ggc agg aac ttt      384
Gly Tyr Ala Ile Leu Arg Val Ser Leu Met Trp Arg Gly Arg Asn Phe
        115                 120                 125

cgc gtc ctc aag tac ttt act cgg agc ctt gag gac aag gac cgg ctg      432
Arg Val Leu Lys Tyr Phe Thr Arg Ser Leu Glu Asp Lys Asp Arg Leu
    130                 135                 140

ggg ttc tgg aag ttt cgg gag ctg aca gca gac act ggt ctc tac ctg      480
Gly Phe Trp Lys Phe Arg Glu Leu Thr Ala Asp Thr Gly Leu Tyr Leu
145                 150                 155                 160

gcg gcc cgg cct ggg cgg tgt gcc gag ctc ctg aag gag gag ctg att      528
Ala Ala Arg Pro Gly Arg Cys Ala Glu Leu Leu Lys Glu Glu Leu Ile
                165                 170                 175

taa                                                                  531


<210> SEQ ID NO 4
<211> LENGTH: 176
<212> TYPE: PRT
<213> ORGANISM: Homo sapiens

<400> SEQUENCE: 4

Met Met Ser Phe Leu Leu Gly Ala Ile Leu Thr Leu Leu Trp Ala Pro
1               5                   10                  15

Thr Ala Gln Ala Glu Val Leu Leu Gln Pro Asp Phe Asn Ala Glu Lys
            20                  25                  30

Ile Gly Gly Phe Trp Arg Glu Val Gly Val Ala Ser Asp Gln Ser Leu
        35                  40                  45

Val Leu Thr Ala Pro Lys Arg Val Glu Gly Leu Phe Leu Thr Leu Ser
    50                  55                  60

Gly Ser Asn Leu Thr Val Lys Val Ala Tyr Asn Ser Ser Gly Ser Cys
65                  70                  75                  80

Glu Ile Glu Lys Ile Val Gly Ser Glu Ile Asp Ser Thr Gly Lys Phe
                85                  90                  95

Ala Phe Pro Gly His Arg Glu Ile His Val Leu Asp Thr Asp Tyr Glu
            100                 105                 110

Gly Tyr Ala Ile Leu Arg Val Ser Leu Met Trp Arg Gly Arg Asn Phe
        115                 120                 125

Arg Val Leu Lys Tyr Phe Thr Arg Ser Leu Glu Asp Lys Asp Arg Leu
    130                 135                 140

Gly Phe Trp Lys Phe Arg Glu Leu Thr Ala Asp Thr Gly Leu Tyr Leu
145                 150                 155                 160

Ala Ala Arg Pro Gly Arg Cys Ala Glu Leu Leu Lys Glu Glu Leu Ile
```

165 170 175

<210> SEQ ID NO 5
<211> LENGTH: 5159
<212> TYPE: DNA
<213> ORGANISM: Homo sapiens
<220> FEATURE:
<221> NAME/KEY: 5'UTR
<222> LOCATION: (1)..(5159)

<400> SEQUENCE: 5

```
tgtttatttt tattattttt ttttttaaa tttatttaac ataattttta ttaataataa     60

taataaatat agtttgtaaa ttttaaaaat aaaagagaag agataaagaa tagattaaat    120

gaattatata aatgaattaa ggtaatactc aatcctttgg atatgtggga ttatacacca    180

tataattttg ttatatttaa tattagtata tatggtaggg tgtatgtgag aaaaggtaaa    240

acttaaaaaa gcggtgaatt acaagatcgg taacgaaggt cgaaaagaaa ggaaatagcg    300

ggtgtctggt gatgtcttgg atttgagggt cgggggtttc gaactctttt taaggtccat    360

tatttaggcg cggcggggag agaggtatgt aaaaccgcaa gatggggtcc ttatcaggat    420

aaggaccacg agtgactgtt agcagaaagt aatatcatga ggaaacagta aaaaaaatac    480

ttatgagttg ggttgggagg ggactgagct ctgagaaagg accccagttc actatgtcaa    540

aaacgaaaaa aaggcaaggc gcagtggctc acgcctgtaa tcccggcact ttgggaggcc    600

aaggagggca gatcacctga ggtcaggagt ttgagaccag cctgaccaac atggtgaaat    660

cctgtctcta ctaaaaatgc aaaaaaaatt agacgggcat ggtggctact gttatcccag    720

ctacatggga ggctgaggca ggagaatcgc ttgaacccgg gaggtggaga ttgcagtgag    780

ctgagattgc accactgcac tccagcctga gtgacagagt gagaccccgt cttaaaaaac    840

aaaacaaggc caggcacggt ggctcatgcc tgcaatccca gcactctggg aggctgaggc    900

aggtggatca caaggtcagg agatcgagac catcctggct aacatggtga aaccctgtct    960

ctactaaaaa tacaaagaat tatcccagca tggtggtgga cgcctgtggt cccagctact   1020

ccggaggctg aggtgggaga atggcgtgaa cccaggaggt ggagcttgca gtgagctgag   1080

attgcgccac agcactccag cctgggcgac agagcgagac tccatctcaa aaaaagaaaa   1140

aaaaaaaaaa aaaaaaaaga aaaaaaagaa aaaagaaaaa aagaaaagaa aacgaagaaa   1200

aaccacaaat aaataaaagt tgaggtatga tgtatgcaca gctgcattcg ccccctttgag  1260

ggcacagttg tgtgagttta gacaaatgca aatgttcatg gaaccactgc aagtgcgaca   1320

cagcagctct ggtgcccaca aagcttcctc gaggtccctt gcggtcaatc actgcccgca   1380

cctcagccct cagagccact gggaagcccc ctgccctgtg ggctcacctg tcctagaacg   1440

tcgtataaaa ggagtcgcag atcgcagcct tttccacctg gcttctgtcc ctctgcaggc   1500

tgcacctggg attcagccac cttcgttcct tttactgctg agtgtccatc acgtgctgct   1560

catgcagaag tgctcaagtt cgctgtaaac gtagttttca tttctcccgg gtggagacct   1620

ccataagtag gtaggttggt ggaatgtttc actgcatgag agtctgccag gaagttttgc   1680

agtgtggtcc cgtcttgttc ttcgcgcaga gggtgatagc tctgctgact cccagccctc   1740

acaggctcta gggattgagc ctgtttctgt ggaacgcctt ccatggtctg cgaggtgcac   1800

agaggggtct caaaaagctt ccaggttgca tcttcccatg gactgatgct gagcgtgttc   1860

tcatctccca tccggatgtt ttctttggtg gagtatcttt tcagatctct tgccttttta   1920

tttttatttg tttatatata tattttgaga cggaattttg ctctttcact taggttggag   1980

tgcaacggcg cgatcttggc tcactgcaac ctccccccac ccacctcact ttgggttcaa   2040
```

-continued

```
gcgattctcc tgcctcagcc tcccgagtag ctgggactac aggcgcccgc caccatgccc   2100
ggctaatttt tgtattttga gaagagatag ggtttcacca tgttggccag gctggtctcg   2160
aactcctgac ctcaggtgat ccacccgcct cggcctccca aaatgcgagg atcacaggcg   2220
tgagatgcca cacctggcct ctttttattt ttaatggagt ggcttgtttt cttattactc   2280
agtcttggga gttcctcatg gatgctggat ttcagtctcg tctcaggtgt atgcgttttg   2340
tagatgtttt ctgtagggac cagccccaca gggttggtga gtttctccct gtgtgctgag   2400
atgagagggc atagaaataa ggacacaaga aaaagacata aaagaaaaga cagctgggcc   2460
tggggaccac taccaccaag acgtggagac cggtagtggc cccgaatgtc tggctgtgct   2520
gatatttatt ggatacaaag caaaagggac agggtaaaga gtgtgagtca tctccaatga   2580
taggtaaggt gacgtgagtc acgtgtccac cggatggggg gcccttccct gtttggcagc   2640
caaggcggag agagagagag agagacagct tacatcatta tttctgcata tcagagactt   2700
ttagtacttt cactaattga ctactgctat ctagaaggca gagccaggtg tacaggatgg   2760
aacatgaagg cggactacga gcgtgaccac tgaagcacag catcacaggg agacggttag   2820
gcctctggat aactgcgggc aggtctgact gatgtcaggc cctccacagg aggtggagga   2880
gtagagtcct ctctaagctc ccccggggga aagggagact ccctttccct gtctgctaag   2940
tagcaggtgt tttcccttga cactgacgct actgctagat cacggtccgc ttggcaaccg   3000
gtgtcttccc agacgctggc gtcaccacta gaccaaggag ccctctggtg gccctgtccg   3060
gcgtaacaga aggctcgcac tcttgtcttc tggtcacttc tcactatgtc ccctcagctc   3120
ctatctctgt atggcctggt ttttcctagg ttataattgt agagcaagga ttattataat   3180
attggaataa agagtaattg ctacaagcta atgattaata atattcatat ataatcatgt   3240
ctatgatcta gatctagtat aactcttgtt attttatata ttttattaaa ctggaacagc   3300
tcgtgccctc ggtctcttgc ttcggcatct gggtggcttg ctgaccacag ttttcctgct   3360
gtatctaact gctggcttag gtgaacctgt caggggcgtg gctgggaact ggaacctcct   3420
gaagaccagt ggaggccaca agcagaagcc ctcggctcct tcccttcccc gatgctgggg   3480
gccaagggtc tttctctgac cctgtccccc cctcacgtta ccagtggagg gtgtccaggt   3540
tcttggcatt ttgaacaaag aattggacaa aacacacaaa caaagcaagg aaagaatgaa   3600
gcaacaaaag cagaaattta ttgaaaatga aagcactctt tacagggtgg gagcgggctg   3660
agcaagcagc tcaagggccc cggttacaga attttctggt gtttcaatat cctctagcgg   3720
tttaccattg gttacttggt gtatgcccta tgtaaatgaa gaggatgaag tcaaagtcat   3780
tttctcggct gagcatactg tcacgcctgt aatcccagta ctttgggagg ctgaggtggg   3840
tgtatcacct gaggtcggga gttcaagacc agcctgatga acatggagaa accccgtctc   3900
tactaaaaat acaaaattag ctgggtgtgg tggcgggtgc ctgtaatccc agatagtcag   3960
gaggctgagg caggaaaatc gcttaaaccc gggaggcaga ggctgcagag agccaaggag   4020
tgcaccactg cactccagcc tgggcaacaa gagcaaaact ccatctcaaa aaacaaacaa   4080
acaaaacgaa gtcatgtact cggtatgagc cctacgtaaa cggagaggat ggagtgaagg   4140
tacaaagcca ttcacattcc cgtcatcgtt agtgtttcca gttgatttgg ttctaggatg   4200
cccttgggct ccctgcgtcc aggccctctt ctcctgcctc actctcactc cagaggactg   4260
gcagtgctgg cctccctggc aggactcccg cccctgacca gaggggtctg ggcgtgctcc   4320
gaggccacct gctgctcctt gcccagtgtc cctgggtgct ctgtggggac acagagaggt   4380
cacttgggag gttcctgcct ctgccagact gcggcgcctt cctggcgtca ttgccccctg   4440
```

```
cacgcttata caaccagtga taaggcggta tccaatgccg taatcctccc cagggccagc   4500

ccagccctgt ccggtcccgt ccggtccctg gcctgcttgc tgggagccca gctgggggct   4560

gcatcggggg tggtgggggt ctggagtgag gggtgcccag gcctctctca cagtgtgggg   4620

gcacaagctc tgccctggac actctgccag tgtgacccta ccccccatgt tgggggtgag   4680

agaagggggc tttctgggtg gccagatccc aggagagggg gcctagccag accaacccca   4740

gcccagctct ctgcagctgt accccaaagg ccctggccca gcccagccag acagagtgtg   4800

gacagagggg cttgggtgcg agtccaggca aggcaggaca agtctctgct gtggcttggc   4860

agtggccccg tgactggtga catagtctgg caggcctagg ggacaaatcc tcagcccggg   4920

tgcatcaggc cagagcctgg ctgtctggag ccctccagga aatgaccccc cgggctgggg   4980

gacatccgag tgattgtgcc aaacaatgga caagggggcc ggagtctcag agccgaagtg   5040

ccttccgctt ccatctgctc cgcccaggag caggtgcacc caggtggtgg cctgggctat   5100

aaagctggcc ccctggggct tggggactca gcaccagggg ctggagggca ggggagggg    5159
```

<210> SEQ ID NO 6
<211> LENGTH: 175
<212> TYPE: PRT
<213> ORGANISM: Mus musculus
<220> FEATURE:
<221> NAME/KEY: mat_peptide
<222> LOCATION: (1)..()

<400> SEQUENCE: 6

```
Met Glu Ala Arg Leu Leu Ser Asn Val Cys Gly Phe Phe Leu Val Phe
1               5                   10                  15

Leu Leu Gln Ala Glu Ser Thr Arg Val Glu Leu Val Pro Glu Lys Ile
            20                  25                  30

Ala Gly Phe Trp Lys Glu Val Ala Val Ala Ser Asp Gln Lys Leu Val
        35                  40                  45

Leu Lys Ala Gln Arg Arg Val Glu Gly Leu Phe Leu Thr Phe Ser Gly
    50                  55                  60

Gly Asn Val Thr Val Lys Ala Val Tyr Asn Ser Ser Gly Ser Cys Val
65                  70                  75                  80

Thr Glu Ser Ser Leu Gly Ser Glu Arg Asp Thr Val Gly Glu Phe Ala
                85                  90                  95

Phe Pro Gly Asn Arg Glu Ile His Val Leu Asp Thr Asp Tyr Glu Arg
            100                 105                 110

Tyr Thr Ile Leu Lys Leu Thr Leu Leu Trp Gln Gly Arg Asn Phe His
        115                 120                 125

Val Leu Lys Tyr Phe Thr Arg Ser Leu Glu Asn Glu Asp Glu Pro Gly
    130                 135                 140

Phe Trp Leu Phe Arg Glu Met Thr Ala Asp Gln Gly Leu Tyr Met Leu
145                 150                 155                 160

Ala Arg His Gly Arg Cys Ala Glu Leu Leu Lys Glu Gly Leu Val
                165                 170                 175
```

<210> SEQ ID NO 7
<211> LENGTH: 27
<212> TYPE: DNA
<213> ORGANISM: Mus musculus
<220> FEATURE:
<221> NAME/KEY: primer_bind
<222> LOCATION: (1)..(27)

<400> SEQUENCE: 7

-continued

```
cttctctggt acaagctcca ccctggt                                          27


<210> SEQ ID NO 8
<211> LENGTH: 24
<212> TYPE: DNA
<213> ORGANISM: Mus musculus
<220> FEATURE:
<221> NAME/KEY: primer_bind
<222> LOCATION: (1)..(24)

<400> SEQUENCE: 8

tggatggata gatgcataca tgag                                             24


<210> SEQ ID NO 9
<211> LENGTH: 20
<212> TYPE: DNA
<213> ORGANISM: Mus musculus
<220> FEATURE:
<221> NAME/KEY: primer
<222> LOCATION: (1)..(20)

<400> SEQUENCE: 9

caacggtggt atatccagtg                                                  20


<210> SEQ ID NO 10
<211> LENGTH: 21
<212> TYPE: DNA
<213> ORGANISM: Mus musculus
<220> FEATURE:
<221> NAME/KEY: primer
<222> LOCATION: (1)..(21)

<400> SEQUENCE: 10

gatgtgctcc aggctaaagt t                                                21


<210> SEQ ID NO 11
<211> LENGTH: 21
<212> TYPE: DNA
<213> ORGANISM: Mus musculus
<220> FEATURE:
<221> NAME/KEY: primer
<222> LOCATION: (1)..(21)

<400> SEQUENCE: 11

agaaacggaa tgttgtggag t                                                21
```

EPIDIDYMAL LIPOCALIN GENE AND USES THEREOF

CROSS REFERENCE TO RELATED APPLICATIONS

This application is a divisional of U.S. patent application Ser. No. 10/451,867 filed Oct. 28, 2003, which is a national phase application of the PCT International Patent Application PCT/US01/49639, filed Dec. 27, 2001 which is based on and claims priority to U.S. Provisional Patent Application Ser. No. 60/258,655 filed Dec. 29, 2000, the entire contents of each of which are herein incorporated by reference in their entirety.

GRANT STATEMENT

This work was supported by NICHD grant HD36900. Thus, the U.S. Government has rights in the invention.

FIELD OF THE INVENTION

The present invention generally relates to epididymal function and male fertility. More particularly, the present invention provides lipocalin nucleic acid and polypeptide sequences, a lipocalin gene promoter region that directs gene expression in the epididymis, chimeric genes comprising disclosed lipocalin sequences, and uses thereof.

Table of Abbreviations

| | |
|---|---|
| CAT | chloramphenicol acetyl transferase |
| ES | embryonic stem cell |
| FCS | fluorescence correlation spectroscopy |
| hEP17 | human Epididymal Protein 17 |
| mE-RABP | mouse Epididymal Retinoic Acid Binding Protein |
| mEP17 | mouse Epididymal Protein 17 |
| MS | mass spectroscopy |
| PCR | polymerase chain reaction |
| PGK | phosphoglycerate kinase |
| pLN-17 | mEP17 targeting vector for homologous recombination |
| RAR | Retinoic Acid Receptor |
| RT-PCR | reverse transcription polymerase chain reaction |
| SELDI | surface-enhanced laser desorption/ionization |
| SPR | surface plasmon resonance |
| TOF | time of flight mass spectroscopy |

BACKGROUND ART

Recent studies of reproductive frequency in the United States report that 7% of married couples (greater than 2 million couples) describe difficulty in achieving a pregnancy. See Fidler and Bernstein (1999) *Public Health Reports* 114:494-511. Many individuals now seek medical support for conception, including infertility diagnosis and assisted reproductive treatment. The monetary costs for such services are substantial, and financial commitment must increase to include pre- and post-natal care of multiple birth pregnancies often associated with infertility treatment. A tumult of legal and ethical issues have emerged regarding the rights of parents and unborn children that are conceived by an unconventional method. The escalating magnitude of monetary, legal, and ethical concerns when considering pregnancy has established infertility as a significant public health issue.

Rational treatment approaches for many andrological disorders resulting in infertility are still lacking. See Kamischke and Nieschlag (1999) *Human Reproduction* 14(Suppl. 1):1-23. The cause of male infertility is often unidentifiable, referred to generally as "idiopathic infertility", or the presumed pathology is not yet met with an unequivocal therapy. Intracytoplasmic sperm injection has been a successful method for enabling fertilization in many cases, yet a less interventive treatment is still sought. The historical use of approaches now deemed ineffective emphasizes the importance of thorough studies during early stages of therapy development. In particular, there is a need for more sophisticated diagnostic tools that detect molecular bases of male infertility and for non-surgical therapies that are supported by solid physiological data. An initial effort in this regard is the development of animal models of male infertility.

A related medical incentive is the development of new methods for contraception. See Baird and Glasier (1999) *BMJ* 319:969-972. The prevalence of contraceptive use is increasing worldwide, however, existing contraceptive means are limited by adverse side effects, inconvenience, and remaining instances of ineffectiveness. In particular, there are presently no safe and reversible means for male contraception. One strategy that has been explored recently is an immunological approach for disrupting endocrine or physiological events that normally promote pregnancy. Vaccines that comprise antigens of sperm plasma membrane proteins, zona pellucida proteins of the egg, or gonadotropin releasing hormone have shown success in suppressing fertility when administered to several mammalian subjects, including humans. See U.S. Pat. Nos. 6,096,318 and 6,132,270; Barber and Fayrer-Hosken (2000) *J Reprod Immunol* 46:103-124; Paterson et al. (2000) *Cells Tissues Organs* 166:228-232; Srivastav (2000) *J Reprod Fertil* 119:241-252; Feng et al. (1999) *J Reprod Med* 44:759-765; Naz (1999) *Immunol Rev* 171:193-202; Talwar (1999) *Immunol Rev* 171:173-192.

Although animal use and clinical trials of immunocontraceptive vaccines are encouraging, existing vaccines present significant complications, for example, auto-immune reactions. Thus, current research is focused on identifying new antigens that can provide safer vaccines. Animal models with implications for post-testicular human male contraceptives acting at the epididymis offer promising leads. See Nikkanen et al. (2000) *Contraception* 61:401-406; Cooper and Yeung (1999) *Hum Reprod Update* 5:141-152. To establish molecular targets for vaccine and drug development, proteins that are essential for epididymal function have been identified (Srivastav, 2000; Diekman et al. (1999) *Immunol Rev* 171:203-211; Costa et al. (1997) *Biol Reprod* 56:985-990; Sonnenberg-Riethmacher et al. (1996) *Genes Dev* 10:1184-1193).

During their transit through the epididymis, spermatozoa undergo biochemical and morphological changes to acquire motility and the ability to fertilize an oocyte in vivo. The maturation process occurs progressively along the epididymal duct and is believed to depend on epididymal secretory proteins. The epididymal epithelial cells secrete proteins in a highly regulated and regionalized manner such that spermatozoa encounter luminal fluid protein in a specific sequence. Indeed, each region within the epididymis is a unique microenvironment adapted with a characteristic milieu of ions, organic solutes, proteins, and steroids. See Cornwall et al. (2001) in "*The Epididymis*", Plenum Press. Spatially-restricted gene expression as well as regional differences in cellular morphology define three distinctive regions of the epididymis known as the caput, corpus, and cauda. These structural subdivisions and highly regionalized gene expression therein are observed in the epididymis of several organisms, including humans (Krull et al. (1993) *Mol Reprod Dev* 34:16-34).

Regionalization of the epididymis likely fulfills an essential and cumulative role in the maturation and survival of spermatozoa. In support thereof, targeted mutation of the mouse c-ros tyrosine kinase receptor confers male sterility, although sperm production is not affected. c-ros is normally expressed in the initial segment of the epididymis, and animals lacking c-ros function show specific underdevelopment and lack of cellular differentiation within the initial segment (Sonnenberg-Riethmacher et al., 1996). Sperm taken from a c-ros mutant mouse are less motile due to flagellar angulation, suggesting that failure of differentiation of epithelial cells in one segment of the epididymis can affect sperm maturation and survival (Yeung et al. (1999) *Biol Reprod* 61:1062-1069).

To generate regionalization within the epididymal epithelium, gene expression is precisely controlled, in part through transcriptional regulation. Transcription factors modulate transcription by binding DNA cis-regulatory sequences, most often located upstream of the gene promoter and transcription start site, and by concomitantly affecting assembly of cellular transcriptional machinery at the relevant promoter. Therefore, cis-regulatory sequences of epididymal-specific genes and the transcription factors that are operative through these sites are important elements in understanding epididymal function as it contributes to sperm maturation. Current approaches to identify mechanisms involved in region-specific gene expression in the epididymis have been limited by a lack of identified transcriptional regulatory proteins which are key to this process. See Cornwall et al. (2001).

Candidate regulators include components of retinoid signaling pathways. Most elements known to be involved in retinoid signaling are present in the epididymis, including epididymal retinoic acid binding protein (mE-RABP), cellular retinol-binding protein type I (CRBP I), cellular retinoic acid binding protein type I (CRABP I), retinoic acid receptor alpha (RARα), retinoic acid, and retinyl esters. Moreover, studies addressing the function of such elements emphasize the important role of retinoid signaling pathways in epididymal integrity. In retinoid deficient animals, there is widespread squamous metaplasia and keratinization of the epididymal epithelium (Wolbach (1925) *J Exp Med* 42:753-777), and abnormal synthesis and secretion of several epididymal proteins (Astraudo et al. (1995) *Arch Androl* 35:247-259). Similarly, overexpression of a dominant negative form of RARα leads to disorganization of the epididymal epithelium and concomitant infertility (Costa et al., 1997). In a related study, RARα knockout mice display aspermatogenesis and vacuolization of the epididymal epithelium (Lufkin et al. (1993) *Proc Natl Acad Sci USA* 90:7225-7229), and animals lacking both RARα and RARγ function show epididymal dysplasia (Mendelsohn et al. (1994) *Development* 120:2749-2771).

The mE-RABP protein is of particular interest among regulators of retinoid signaling, as it appears to be expressed selectively in the mid and distal caput of the epididymis. mE-RABP is a member of a family of secreted lipocalin proteins. Structural analyses reveal that lipocalins comprise an eight-stranded β barrel that is closed at one end by an α-helical turn, thereby forming a hydrophobic binding cavity. This hydrophobic pocket is well-adapted for noncovalent binding and transport of small lipophilic ligands. mE-RABP binds active retinoids (9-cis and all-trans retinoic acid), and functions as a retinoid carrier protein in the epididymis. See Ong et al. (2000) *Biochim Biophys Acta* 1482(1-2):209-17.

Recent studies by the co-inventors of the present application have identified a similar gene encoding a 17 kDa lipocalin, Mouse Epididymal Protein of 17 kDa (mEP17) (Lareyre et al. (2001) *Endocrinology* 142:1296-1306). mEP17 and mE-RABP are significantly related by several measures that collectively suggest mEP17 also functions as a regulator of retinoid signaling in the epididymis. First, mE-RABP and mEP17 are positioned adjacent to each other on mouse chromosome 2. Exon/intron boundaries are strictly conserved between mE-RABP and mEP17, supporting that these genes arose by gene duplication. Second, mEP17 shows regionalized expression in the epididymis. mEP17 expression is limited to the initial segment of the caput epididymis, while mE-RABP is expressed in the adjacent mid and distal caput epididymis. Third, the mEP17 protein contains two motifs (G-X-W and T-D-Y) and two cysteine residues that are characteristic features shared by members of the lipocalin protein family. With the exception of these motifs, mEP17 shows low sequence similarity with other known lipocalins. However, it is well established that lipocalin family members do not show significant sequence homology (average 25% identity and 50% homology between representative members). Rather, lipocalins are more clearly related by assessing homology of secondary and tertiary structure. The tryptophan residue of the G-X-W motif is required for binding of lipophilic ligands, and the two cysteine residues form a intramolecular disulfide bond that influences ligand affinity. In addition, a putative signal sequence at the amino-terminal of the mEP17 precursor suggests that it is cleaved to generate a mature secreted protein, consistent with its identification as a lipocalin. These structural similarities between mEP17 and other lipocalins, most significantly mE-RABP, suggest that mEP17 is also a carrier for retinoid ligands.

The present invention relates to a current challenge in developing animal models of infertility, male fertility treatments, and male contraceptives. To this end, the present invention provides an isolated promoter region of the mEP17 gene, an isolated nucleic acid molecule encoding a human mEP17 gene (hEP17), an isolated promoter region of hEP17, and chimeric genes comprising the disclosed sequences. Host cells expressing a recombinant EP17 gene or an mEP17 promoter region operably linked to a reporter gene sequence are useful in screening assays for discovery of substances that modulate EP17. A chimeric gene comprising an mEP17 promoter region can also be used to direct transcription of a heterologous nucleotide sequence in the epididymis of a host organism. The present invention further provides an EP17 polypeptide that can be used for vaccine or drug development. By provision of epididymal lipocalin nucleotide and polypeptide sequences, and methods for using the same, the present invention meets a long-felt need for advancement in fertility research.

SUMMARY OF THE INVENTION

The present invention provides an isolated promoter region of an EP17 gene that reconstitutes endogenous expression in epididymis. In one preferred embodiment, a promoter region of the invention comprises a 5.3 kb fragment (GenBank Accession No. AF08222) of mouse genomic clone 10983 (Genome Systems, Inc.) between the EcoRV and SalI restriction sites, or functional portion thereof. More preferably, the functional portion of the promoter region comprises a TATA box and at least one cis-acting regulatory sequence selected from the group including but not limited to a Sp-1 binding site, an AP-1 binding site, a retinoic acid receptor binding site, an androgen receptor binding site, a C-Ets binding site, a SRY binding site, an AP-4 binding site, a C/EBP binding site, and combinations thereof. Most preferably, an isolated promoter region of the present invention comprises the nucleotide sequence of SEQ ID NO:1, a nucleic acid molecule substantially identical to SEQ ID NO:1, or a 20 base pair nucleotide sequence identical to a contiguous 20 base pair nucleotide portion of SEQ ID NO:1.

The present invention also provides a human EP17 gene. Preferably, the human EP17 gene comprises the sequence set forth as SEQ ID:2, a nucleic acid molecule that is substantially similar to SEQ ID NO:2; or a nucleic acid molecule comprising a 20 base pair nucleotide sequence that is identical to a contiguous 20 base pair sequence of SEQ ID NOs:2. The present invention further provides an isolated promoter region derived from a human EP17 gene. In this case, a hEP17 promoter region is preferably an about 5160 base pair region immediately upstream of the human EP17 transcription start site. More preferably, an isolated promoter region of the present invention comprises a TATA box and at least one cis-acting regulatory sequence selected from the group including but not limited to Sp-1 binding site, an AP-1 binding site, a cAMP response element binding protein (CREB) binding site, a SRY-related HMG-box gene 5 (Sox5) binding site, a Sex-determining region Y gene product (SRY) binding site, a c-Ets binding site, a GATA binding site, an Octamer transcription factor 1 (Oct-1) binding site, and combinations thereof. Most preferably, an isolated promoter of the present invention comprises the nucleotide sequence of SEQ ID NO:5, a nucleic acid molecule substantially identical to SEQ ID NO:5, or a 20 base pair nucleotide sequence identical to a contiguous 20 base pair nucleotide portion of SEQ ID NO:5.

The present invention further provides a chimeric gene comprising an EP17 promoter region operably linked to a heterologous nucleotide sequence. Preferably, the EP17 promoter region comprises the nucleic acid molecule of SEQ ID NOs:1 or 5, or functional portion thereof. In a preferred embodiment, a chimeric gene of the invention is carried in a vector and expressed in a host cell including but not limited to a bacterial cell, a hamster cell, a mouse cell, or a human cell.

The present invention also provides a transgenic animal having a transgene that comprises a chimeric gene of the present invention. In a preferred embodiment, expression of the chimeric gene alters fertility of the host animal.

The present invention also provides a method for identifying a substance that regulates EP17 expression using a chimeric gene that includes an isolated EP17 promoter region operably linked to a reporter gene. According to this method, a gene expression system is established that includes the chimeric gene and components required for gene transcription and translation so that reporter gene expression is assayable. To select a substance that regulates EP17 expression, the method further provides the steps of using the gene expression system to determine a baseline level of reporter gene expression in the absence of a candidate regulator, providing a plurality of candidate regulators to the gene expression system, and assaying a level of reporter gene expression in the presence of a candidate regulator. A candidate regulator is selected whose presence results in an altered level of reporter gene expression when compared to the baseline level. Preferably, the isolated EP17 promoter region used in this method comprises the sequence of SEQ ID NOs:1 or 5, or functional portion thereof.

In another aspect of the invention, a method is provided for producing an epididymal cell line using a chimeric gene comprising an EP17 promoter operably linked to a gene encoding a selectable marker. According to the method, a transgenic animal is generated that expresses a selectable marker gene. Preferably, the selectable marker gene is an antibiotic resistance gene. More preferably, the antibiotic resistance gene is a neomycin resistance gene. Epididymal cells are procured from the transgenic animal and stably reproduced in cell culture using selection of the marker gene. Preferably, the EP17 promoter region used to perform this method is the nucleic acid molecule of SEQ ID NO:1, or functional portion thereof.

Another aspect of the present invention pertains to a method for mutagenizing an EP17 locus by homologous recombination. The method uses a targeting vector having an isolated EP17 promoter region, a marker gene, and an isolated EP17 3' flanking region. In a vector so constructed, the marker gene is positioned between the promoter region and the 3' flanking region. In one embodiment, the targeting vector further comprises a mutant EP17 coding sequence, also positioned between the promoter region and the 3' flanking region. The targeting vector is linearized by digestion with a restriction endonuclease at a site other than within the promoter region, marker gene, 3' flanking region, and optional mutant EP17 coding sequence. The linearized vector is introduced into embryonic stem cells and is assayed by detecting the marker gene in the stem cells. Stem cells bearing the vector are used to create a transgenic vertebrate animal. According to the method, a homologous recombination event is mediated at the EP17 locus, thereby exchanging native mEP17 gene sequences positioned between the promoter region and the 3' flanking region with vector nucleotide sequences positioned the same. In a more preferred embodiment, male EP17 mutant animals produced by the disclosed method are sterile.

The present invention also discloses a human EP17 polypeptide and an isolated nucleic acid sequence encoding the same. Preferably, an isolated EP17 polypeptide, or functional portion thereof, comprises a polypeptide encoded by the nucleic acid molecule of SEQ ID NO:3, a polypeptide encoded by a nucleic acid molecule that is substantially identical to SEQ ID NO:3, a polypeptide fragment encoded by a 20 nucleotide sequence that is identical to a contiguous 20 nucleotide sequence of SEQ ID NO:3; a polypeptide having an amino acid sequence of SEQ ID NO:4, a polypeptide that is a biological equivalent of the polypeptide of SEQ ID NO:4, or a polypeptide that is immunologically cross-reactive with an antibody that shows specific binding with a polypeptide comprising some or all amino acids of SEQ ID NO:4. Preferably, the polypeptide of the present invention comprises a human EP17 polypeptide.

The present invention further teaches chimeric genes having a heterologous promoter that drives expression of a nucleic acid sequence encoding an EP17 polypeptide. Preferably, the chimeric gene is carried in a vector and introduced into a host cell so that an EP17 polypeptide of the present invention is produced. Preferred host cells include but are not limited to a bacterial cell, a hamster cell, a mouse cell, or a human cell.

In another aspect of the invention, a method is provided for detecting a nucleic acid molecule that encodes an EP17 polypeptide. According to the method, a biological sample having nucleic acid material is hybridized under stringent hybridization conditions to an EP17 nucleic acid molecule of the present invention. Such hybridization enables a nucleic acid molecule of the biological sample and the EP17 nucleic acid molecule to form a detectable duplex structure. Preferably, the EP17 nucleic acid molecule includes some or all nucleotides of SEQ ID NOs:1, 2, 3, or 5. Also preferably, the biological sample comprises human nucleic acid material.

The present invention further teaches an antibody that specifically recognizes an EP17 polypeptide. Preferably, the antibody recognizes some or all amino acids of SEQ ID NO:4. A method for producing an EP17 antibody is also disclosed, and the method comprises recombinantly or synthetically producing an EP17 polypeptide, or portion thereof; formulating the EP17 polypeptide so that it is an effective immunogen; immunizing an animal with the formulated polypeptide to generate an immune response that includes production of EP17 antibodies; and collecting blood serum from the immunized animal containing antibodies that specifically recognize an EP17 polypeptide. Preferably, the EP17 polypeptide used as an immunogen includes some or all amino acid sequences of SEQ ID NO:4.

A method is also provided for detecting a level of EP17 polypeptide using an antibody that specifically recognizes an EP17 polypeptide. According to the method, a biological sample is obtained from an experimental subject and a control subject, and EP17 polypeptide is detected in the sample by immunochemical reaction with the EP17 antibody. Preferably, the antibody recognizes amino acids of SEQ ID NO:4 and is prepared according to a method of the present invention for producing such an antibody.

The present invention further discloses a method for identifying a compound that modulates EP17 function. The method comprises: exposing an isolated EP17 polypeptide to a plurality of compounds; and assaying binding of a compound to the isolated EP17 polypeptide. A compound is selected that demonstrates specific binding to the isolated EP17 polypeptide. Preferably, the EP17 polypeptide used in the binding assay of the method includes some or all amino acids of SEQ ID NO:4.

The present invention further provides a method for modulating EP17 function in a subject. According to the method, a pharmaceutical composition is prepared that includes a substance capable of modulating EP17 expression or function, and a carrier. An effective dose of the pharmaceutical composition is administered to a subject, whereby EP17 activity is altered in the subject. In a preferred embodiment, the substance used to perform this method shows specific binding to some or all amino acids of SEQ ID NO:4 and was discovered by a screening assay method of the present invention. In another embodiment, EP17 function is disrupted by immunizing a subject with an effective dose of the disclosed EP17 polypeptide. The immune system of the subject produces an antibody that specifically recognizes the EP17 polypeptide, and preferably recognizes some or all of amino acids of SEQ ID NO:4. In a further embodiment, a gene therapy vector is used, the vector comprising a nucleotide sequence encoding an EP17 polypeptide. Alternatively, the gene therapy vector comprises a nucleotide sequence encoding a nucleic acid molecule, a peptide, or a protein that interacts with an EP17 nucleic acid or polypeptide. Preferably, the subject is a human subject.

A method is also provided for expressing a nucleotide sequence of interest in epididymis using an EP17 promoter region. According to the method, a gene therapy vector is prepared comprising an EP17 promoter region operably linked to a nucleotide sequence of interest. A gene therapy vector so-constructed is administered to a subject, whereby the nucleotide sequence of interest is expressed in epididymis. Preferably, the EP17 promoter comprises SE ID NO:5, or functional portion thereof. Also preferably, the subject is a human subject.

The invention further provides a method for diminishing the fertile capacity of a subject. According to the method, a chemical compound, peptide, or antibody that interacts with an EP17 polypeptide is identified. Preferably, the polypeptide is the sequence of SEQ ID NO:4 or 6. A pharmaceutical preparation is prepared comprising such a chemical compound, peptide, or antibody, and a carrier. An effective dose of the pharmaceutical composition is administered to a subject, whereby the fertile capacity of the subject is diminished.

The invention further provides a method for promoting the fertile capacity of a subject. In this case, a chemical compound or peptide that interacts with an EP17 polypeptide is identified. Preferably, the polypeptide is the sequence of SEQ ID NO:4 or 6. A pharmaceutical composition comprising the chemical compound or peptide and a carrier is prepared. An effective dose of the pharmaceutical composition is administered to a subject, whereby the fertile capacity of the subject is improved.

Accordingly, it is an object of the present invention to provide novel EP17 nucleic acid and polypeptide sequences, and novel methods relating thereto. This object is achieved in whole or in part by the present invention.

An object of the invention having been stated above, other objects and advantages of the present invention will become apparent to those skilled in the art after a study of the following description of the invention, Figures and non-limiting Examples.

BRIEF DESCRIPTION OF THE DRAWINGS

FIG. 4A shows a high magnification view of the boxed region of FIG. 3 at the boundary between the initial (IS) and proximal caput epididymis (Cp). mEP17 mRNA is highly expressed only in the principal cells of the initial segment (IS). No staining is observed in the conjunctive tissue (CT) and in the epithelial cells of the proximal caput epididymis (Cp).

FIG. 4B shows hybridization of a section of the initial segment with a sense strand digoxygenin-labeled mEP17 RNA. No signal is detected.

FIG. 6 presents BLAST results using human EP17 cDNA sequence of SEQ ID NO:3 as the query sequence. The highest homologies were observed with other epididymal lipocalins (E-RABP and prostaglandin $H_2$-D isomerases).

FIG. 11 shows the nucleotide sequence of the mEP17 5.3 kb promoter region. Putative cis-DNA regulatory elements within the 5' flanking region are underlined, including binding sites for androgen receptor (ARSB), retinoic acid receptor (RARE), Stimulating Protein 1 (SP-1), Activator Protein 1 (AP-1), Octamer transcription factor I (Oct-1), and Sox-5 (SRY-related Sequence #5 Protein). A consensus TATA box is indicated.

FIG. 13 shows the nucleotide sequence of the human EP17 promoter region. Putative cis-DNA regulatory elements are underlined, including a Stimulatory Protein 1 (Sp-1) binding site, an Activator Protein 1 (AP-1) binding site, a cAMP response element binding protein (CREB) site, a SRY-related HMG-box gene (Sox5) binding site, a Sex-determining region Y gene product (SRY) binding site, a c-Ets binding site, a GATA binding site, and an Octamer transcription factor 1 (Oct-1) binding site.

FIG. 15A shows Northern blot analysis of epididymal total RNA (10 µg/lane) extracted from intact (I) and castrated animals at 5, 10, 20, and 30 days following castration (C5, C10, C20 and C30 respectively), hybridized with [$^{32}$P]-labeled mEP17 cDNA.

FIG. 15B shows Northern blot analysis to detect mEP17 RNA four days following hemicastration. Levels of mEP17 RNA in the epididymis of the castrated side (HI) are reduced to 0.7% of RNA levels in the epididymis of the non-castrated side (HC).

FIG. 15C shows Northern blot analysis to detect mEP17 cDNA 5 days after castration (C5) and 5 days after castration and androgen replacement (TP).

FIG. 17A shows Coomassie blue staining that identifies two enriched protein species (boxed).

FIG. 17B shows Western blot analysis using an anti-his tag antibody to detect two recombinant proteins of approximately 21 and 23 kDa, corresponding to the processed and non-processed mEP17 isoforms.

DETAILED DESCRIPTION OF THE INVENTION

Figure 1:
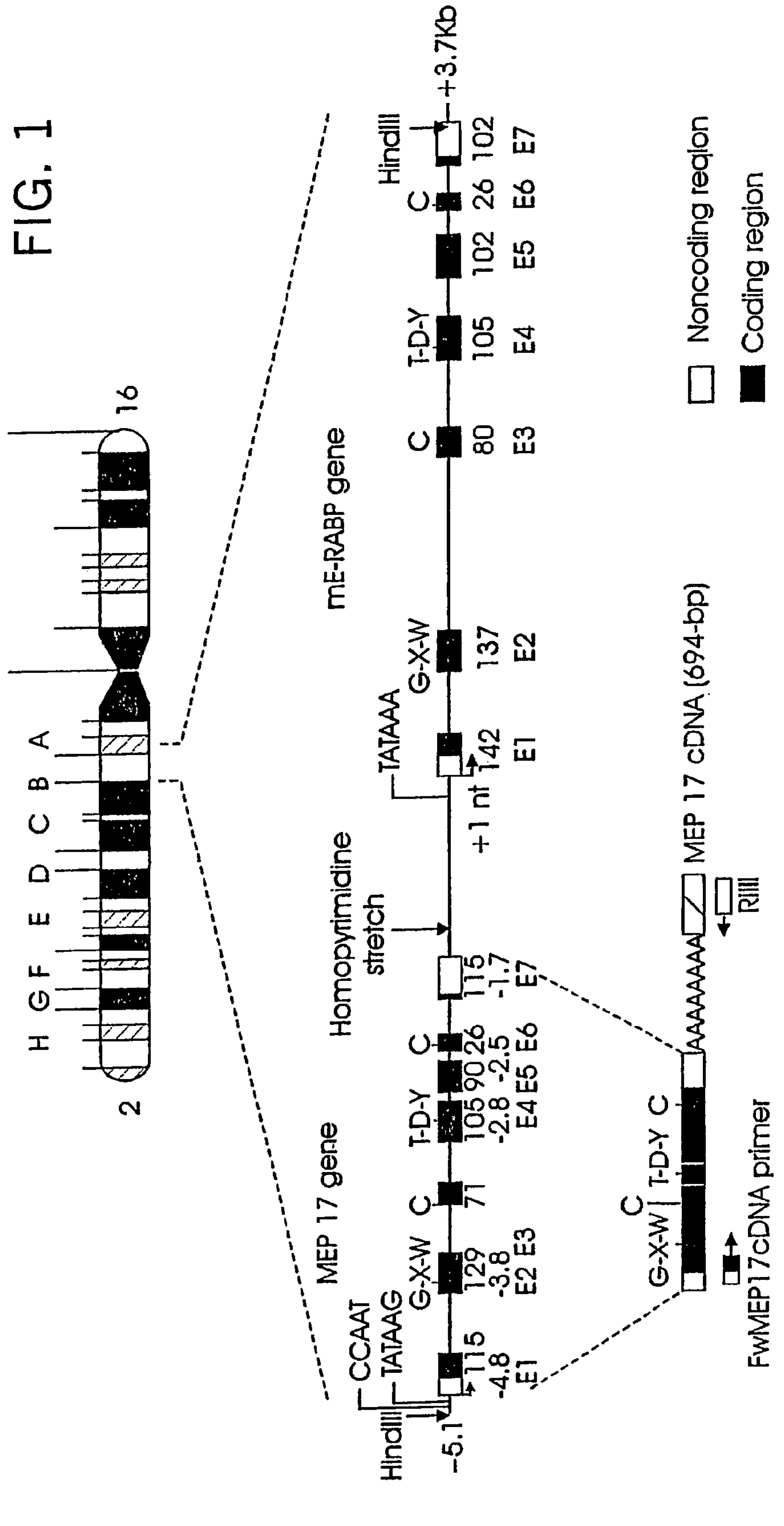
FIG. 1 depicts genomic organization of the mEP17 gene. mEP17 is located upstream from mE-RABP within the locus [A3,B] of the mouse chromosome 2. Exon sizes are indicated in nucleotides. The major transcription initiation sites of both genes are represented with broken arrows. Primer "FwmEP17cDNA" (SEQ ID NO:7) was used for primer extension analysis. Two motifs G-X-W and T-D-Y and two cysteine residues (C) that contribute to the three dimensional structure of lipocalin proteins are also indicated.

The present invention provides isolated nucleic acids comprising a lipocalin gene promoter region (representative embodiments set forth as SEQ ID NOs:1 and 5), isolated nucleic acids comprising a human lipocalin gene (a representative embodiment set forth as SEQ ID NO:2), isolated nucleic acids encoding a lipocalin polypeptide (a representative embodiment set forth as SEQ ID NO:3), isolated lipocalin polypeptides (a representative embodiment set forth as SEQ ID NO:4), and uses thereof. The disclosed lipocalin nucleic acids and polypeptides can be used according to methods of the present invention to generate a mouse model of male infertility, for drug discovery screens, and for therapeutic treatment of fertility-related conditions, among other uses.

1. DEFINITIONS

While the following terms are believed to be well understood by one of ordinary skill in the art, the following definitions are set forth to facilitate explanation of the invention. The entire contents of all publications mentioned herein, including the discussion of the background art presented above, are hereby fully incorporated by reference.

I. A. EP17 Nucleic Acids

The nucleic acid molecules provided by the present invention include the isolated nucleic acid molecules of SEQ ID NOs:1, 2, 3, and 5, sequences substantially similar to sequences of SEQ ID NOs:1, 2, 3, and 5, conservative variants thereof, subsequences and elongated sequences thereof, complementary DNA molecules, and corresponding RNA molecules. The present invention also encompasses genes, cDNAs, chimeric genes, and vectors comprising disclosed EP17 nucleic acid sequences.

The term "nucleic acid molecule" refers to deoxyribonucleotides or ribonucleotides and polymers thereof in either single- or double-stranded form. Unless specifically limited, the term encompasses nucleic acids containing known analogues of natural nucleotides which have similar properties as the reference natural nucleic acid. Unless otherwise indicated, a particular nucleotide sequence also implicitly encompasses conservatively modified variants thereof (e.g. degenerate codon substitutions), complementary sequences, subsequences, elongated sequences, as well as the sequence explicitly indicated. The terms "nucleic acid molecule" or "nucleotide sequence" can also be used in place of "gene", "cDNA", or "mRNA". Nucleic acids can be derived from any source, including any organism.

The term "isolated", as used in the context of a nucleic acid molecule, indicates that the nucleic acid molecule exists apart from its native environment and is not a product of nature. An isolated DNA molecule can exist in a purified form or can exist in a non-native environment such as a transgenic host cell.

The term "purified", when applied to a nucleic acid, denotes that the nucleic acid is essentially free of other cellular components with which it is associated in the natural state. Preferably, a purified nucleic acid molecule is a homogeneous dry or aqueous solution. The term "purified" denotes that a nucleic acid or protein gives rise to essentially one band in an electrophoretic gel. Particularly, it means that the nucleic acid is at least about 50% pure, more preferably at least about 85% pure, and most preferably at least about 99% pure.

The term "substantially identical", the context of two nucleotide or amino acid sequences, can also be defined as two or more sequences or subsequences that have at least 60%, preferably 80%, more preferably 90-95%, and most preferably at least 99% nucleotide or amino acid sequence identity, when compared and aligned for maximum correspondence, as measured using one of the following sequence comparison algorithms (described herein below under the heading Nucleotide and Amino Acid Sequence Comparisons) or by visual inspection. Preferably, the substantial identity exists in nucleotide sequences of at least 50 residues, more preferably in nucleotide sequence of at least about 100 residues, more preferably in nucleotide sequences of at least about 150 residues, and most preferably in nucleotide sequences comprising complete coding sequences. In one aspect, polymorphic sequences can be substantially identical sequences. The term "polymorphic" refers to the occurrence of two or more genetically determined alternative sequences or alleles in a population. An allelic difference can be as small as one base pair.

Another indication that two nucleotide sequences are substantially identical is that the two molecules specifically or substantially hybridize to each other under stringent conditions. In the context of nucleic acid hybridization, two nucleic acid sequences being compared can be designated a "probe" and a "target". A "probe" is a reference nucleic acid molecule, and a "target" is a test nucleic acid molecule, often found within a heterogenous population of nucleic acid molecules. A "target sequence" is synonymous with a "test sequence".

A preferred nucleotide sequence employed for hybridization studies or assays includes probe sequences that are complementary to or mimic at least an about 14 to 40 nucleotide sequence of a nucleic acid molecule of the present invention. Preferably, probes comprise 14 to 20 nucleotides, or even longer where desired, such as 30, 40, 50, 60, 100, 200, 300, or 500 nucleotides or up to the full length of any of SEQ ID NOs:1, 2, 3, and 5. Such fragments can be readily prepared by, for example, directly synthesizing the fragment by chemical synthesis, by application of nucleic acid amplification technology, or by introducing selected sequences into recombinant vectors for recombinant production. The phrase "hybridizing specifically to" refers to the binding, duplexing, or hybridizing of a molecule only to a particular nucleotide sequence under stringent conditions when that sequence is present in a complex nucleic acid mixture (e.g., total cellular DNA or RNA). The phrase "binds substantially to" refers to complementary hybridization between a probe nucleic acid molecule and a target nucleic acid molecule and embraces minor mismatches that can be accommodated by reducing the stringency of the hybridization media to achieve the desired hybridization.

"Stringent hybridization conditions" and "stringent hybridization wash conditions" in the context of nucleic acid hybridization experiments such as Southern and Northern blot analysis are both sequence- and environment-dependent. Longer sequences hybridize specifically at higher temperatures. An extensive guide to the hybridization of nucleic acids is found in Tijssen (1993) "*Laboratory Techniques in Biochemistry and Molecular Biology-Hybridization with Nucleic Acid Probes*" part I chapter 2, Elsevier, N.Y. Generally, highly stringent hybridization and wash conditions are selected to be about 5° C. lower than the thermal melting point ($T_m$) for the specific sequence at a defined ionic strength and pH. Typically, under "stringent conditions" a probe will hybridize specifically to its target subsequence, but to no other sequences.

The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for Southern or Northern Blot analysis of complementary nucleic acids having more than about 100 complementary residues is overnight hybridization in 50% formamide with 1 mg of heparin at 42° C. An example of highly stringent wash conditions is 15 minutes in 0.15 M NaCl at 65° C. An example of stringent wash conditions is 15 minutes in 0.2×SSC buffer at 65° C. (See Sambrook (1989) for a description of SSC buffer). Often, a high stringency wash is preceded by a low stringency wash to remove background probe signal. An example of medium stringency wash conditions for a duplex of more than about 100 nucleotides, is 15 minutes in 1×SSC at 45° C. An example of low stringency wash for a duplex of more than about 100 nucleotides, is 15 minutes in 4-6×SSC at 40° C. For short probes (e.g., about 10 to 50 nucleotides), stringent conditions typically involve salt concentrations of less than about 1.0 M Na ion, typically about 0.01 to 1.0 M Na ion concentration (or other salts) at pH 7.0-8.3, and the temperature is typically at least about 30° C. Stringent conditions can also be achieved with the addition of destabilizing agents such as formamide. In general, a signal to noise ratio of 2-fold (or higher) than that observed for an unrelated probe in the particular hybridization assay indicates detection of a specific hybridization.

The following are examples of hybridization and wash conditions that can be used to clone homologous nucleotide sequences that are substantially identical to reference nucleotide sequences of the present invention: a probe nucleotide sequence preferably hybridizes to a target nucleotide sequence in 7% sodium dodecyl sulfate (SDS), 0.5 M $NaPO_4$, 1 mM EDTA at 50° C. followed by washing in 2×SSC, 0.1%

SDS at 50° C.; more preferably, a probe and target sequence hybridize in 7% sodium dodecyl sulfate (SDS), 0.5 M $NaPO_4$, 1 mM EDTA at 50° C. followed by washing in 1×SSC, 0.1% SDS at 50° C.; more preferably, a probe and target sequence hybridize in 7% sodium dodecyl sulfate (SDS), 0.5 M $NaPO_4$, 1 mM EDTA at 50° C. followed by washing in 0.5×SSC, 0.1% SDS at 50° C.; more preferably, a probe and target sequence hybridize in 7% sodium dodecyl sulfate (SDS), 0.5 M $NaPO_4$, 1 mM EDTA at 50° C. followed by washing in 0.1×SSC, 0.1% SDS at 50° C.; more preferably, a probe and target sequence hybridize in 7% sodium dodecyl sulfate (SDS), 0.5 M $NaPO_4$, 1 mM EDTA at 50° C. followed by washing in 0.1×SSC, 0.1% SDS at 65° C.

A further indication that two nucleic acid sequences are substantially identical is that proteins encoded by the nucleic acids are substantially identical, share an overall three-dimensional structure, are biologically functional equivalents; or are immunologically cross-reactive. These terms are defined further under the heading EP17 Polypeptides herein below. Nucleic acid molecules that do not hybridize to each other under stringent conditions are still substantially identical if the corresponding proteins are substantially identical. This can occur, for example, when two nucleotide sequences are significantly degenerate as permitted by the genetic code.

The term "conservatively substituted variants" refers to nucleic acid sequences having degenerate codon substitutions wherein the third position of one or more selected (or all) codons is substituted with mixed-base and/or deoxyinosine residues (Batzer et al. (1991) *Nucleic Acid Res.* 19:5081; Ohtsuka et al. (1985) *J Biol Chem* 260:2605-2608; Rossolini et al. (1994) *Mol Cell Probes* 8:91-98).

The term "subsequence" refers to a sequence of nucleic acids that comprises a part of a longer nucleic acid sequence. An exemplary subsequence is a probe, described herein above, or a primer. The term "primer" as used herein refers to a contiguous sequence comprising about 8 or more deoxyribonucleotides or ribonucleotides, preferably 10-20 nucleotides, and more preferably 20-30 nucleotides of a selected nucleic acid molecule. The primers of the invention encompass oligonucleotides of sufficient length and appropriate sequence so as to provide initiation of polymerization on a nucleic acid molecule of the present invention.

The term "elongated sequence" refers to an addition of nucleotides (or other analogous molecules) incorporated into the nucleic acid. For example, a polymerase (e.g., a DNA polymerase), e.g., a polymerase which adds sequences at the 3' terminus of the nucleic acid molecule. In addition, the nucleotide sequence can be combined with other DNA sequences, such as promoters, promoter regions, enhancers, polyadenylation signals, intronic sequences, additional restriction enzyme sites, multiple cloning sites, and other coding segments.

The term "complementary sequence", as used herein, indicates two nucleotide sequences that comprise antiparallel nucleotide sequences capable of pairing with one another upon formation of hydrogen bonds between base pairs. As used herein, the term "complementary sequences" means nucleotide sequences which are substantially complementary, as can be assessed by the same nucleotide comparison set forth above, or is defined as being capable of hybridizing to the nucleic acid segment in question under relatively stringent conditions such as those described herein. A particular example of a complementary nucleic acid segment is an antisense oligonucleotide.

The term "gene" refers broadly to any segment of DNA associated with a biological function. A gene encompasses sequences including but not limited to a coding sequence, a promoter region, a cis-regulatory sequence, a non-expressed DNA segment is a specific recognition sequence for regulatory proteins, a non-expressed DNA segment that contributes to gene expression, a DNA segment designed to have desired parameters, or combinations thereof. A gene can be obtained by a variety of methods, including cloning from a biological sample, synthesis based on known or predicted sequence information, and recombinant derivation of an existing sequence.

The term "promoter region" defines a nucleotide sequence within a gene that is positioned 5' to a coding sequence of a same gene and functions to direct transcription of the coding sequence. The promoter region includes a transcriptional start site and at least one cis-regulatory element. The present invention encompasses nucleic acid sequences that comprise a promoter region of an EP17 gene, or functional portion thereof.

The term "cis-acting regulatory sequence" or "cis-regulatory motif" or "response element", as used herein, each refer to a nucleotide sequence that enables responsiveness to a regulatory transcription factor. Responsiveness can encompass a decrease or an increase in transcriptional output and is mediated by binding of the transcription factor to the DNA molecule comprising the response element.

The term "transcription factor" generally refers to a protein that modulates gene expression by interaction with the cis-regulatory element and cellular components for transcription, including RNA Polymerase, Transcription Associated Factors (TAFs), chromatin-remodeling proteins, and any other relevant protein that impacts gene transcription.

The term "gene expression" generally refers to the cellular processes by which a biologically active polypeptide is produced from a DNA sequence.

A "functional portion" of a promoter gene fragment is a nucleotide sequence within a promoter region that is required for normal gene transcription. To determine nucleotide sequences that are functional, the expression of a reporter gene is assayed when variably placed under the direction of a promoter region fragment.

Promoter region fragments can be conveniently made by enzymatic digestion of a larger fragment using restriction endonucleases or DNAse I. Preferably, a functional promoter region fragment comprises about 5000 nucleotides, more preferably 2000 nucleotides, more preferably about 1000 nucleotides, more preferably a functional promoter region fragment comprises about 500 nucleotides, even more preferably a functional promoter region fragment comprises about 100 nucleotides, and even more preferably a functional promoter region fragment comprises about 20 nucleotides.

The terms "reporter gene" or "marker gene" or "selectable marker" each refer to a heterologous gene encoding a product that is readily observed and/or quantitated. A reporter gene is heterologous in that it originates from a source foreign to an intended host cell or, if from the same source, is modified from its original form. Non-limiting examples of detectable reporter genes that can be operably linked to a transcriptional regulatory region can be found in Alam and Cook (1990) *Anal Biochem* 188:245-254 and PCT International Publication No. WO 97/47763. Preferred reporter genes for transcriptional analyses include the lacZ gene (See, e.g., Rose and Botstein (1983) *Meth Enzymol* 101:167-180), Green Fluorescent Protein (GFP) (Cubitt et al. (1995) *Trends Biochem Sci* 20:448-455), luciferase, or chloramphenicol acetyl transferase (CAT). Preferred reporter genes for methods to produce transgenic animals include but are not limited to antibiotic resistance genes, and more preferably the antibiotic resistance gene confers neomycin resistance. Any suitable reporter and detection method can be used, and it will be appreciated by one of skill in the art that no particular choice is essential to or a limitation of the present invention.

An amount of reporter gene can be assayed by any method for qualitatively or preferably, quantitatively determining presence or activity of the reporter gene product. The amount of reporter gene expression directed by each test promoter region fragment is compared to an amount of reporter gene expression to a control construct comprising the reporter gene in the absence of a promoter region fragment. A promoter region fragment is identified as having promoter activity when there is significant increase in an amount of reporter gene expression in a test construct as compared to a control construct. The term “significant increase”, as used herein, refers to an quantified change in a measurable quality that is larger than the margin of error inherent in the measurement technique, preferably an increase by about 2-fold or greater relative to a control measurement, more preferably an increase by about 5-fold or greater, and most preferably an increase by about 10-fold or greater.

The present invention also encompasses chimeric genes comprising the disclosed EP17 sequences. The term “chimeric gene”, as used herein, refers to an EP17 promoter region operably linked to an open reading frame, wherein the nucleotide sequence created is not naturally occurring. In this regard, the open reading frame is also described as a “heterologous sequence”. The term “chimeric gene” also encompasses a promoter region operably linked to an EP17 coding sequence, a nucleotide sequence producing an antisense RNA molecule, a RNA molecule having tertiary structure, such as a hairpin structure, or a double-stranded RNA molecule.

The term “operably linked”, as used herein, refers to a promoter region that is connected to a nucleotide sequence in such a way that the transcription of that nucleotide sequence is controlled and regulated by that promoter region. Techniques for operatively linking a promoter region to a nucleotide sequence are well known in the art.

The terms “heterologous gene”, “heterologous DNA sequence”, “heterologous nucleotide sequence”, “exogenous nucleic acid molecule”, or “exogenous DNA segment”, as used herein, each refer to a sequence that originates from a source foreign to an intended host cell or, if from the same source, is modified from its original form. Thus, a heterologous gene in a host cell includes a gene that is endogenous to the particular host cell but has been modified, for example by mutagenesis or by isolation from native cis-regulatory sequences. The terms also includes non-naturally occurring multiple copies of a naturally occurring nucleotide sequence. Thus, the terms refer to a DNA segment that is foreign or heterologous to the cell, or homologous to the cell but in a position within the host cell nucleic acid wherein the element is not ordinarily found.

The present invention further includes vectors comprising the disclosed EP17 sequences, including plasmids, cosmids, and viral vectors. The term “vector”, as used herein refers to a DNA molecule having sequences that enable its replication in a compatible host cell. A vector also includes nucleotide sequences to permit ligation of nucleotide sequences within the vector, wherein such nucleotide sequences are also replicated in a compatible host cell. A vector can also mediate recombinant production of an EP17 polypeptide, as described further herein below. Preferred vectors include but are not limited to pBluescript (Stratagene), pUC18, pBLCAT3 (Luckow and Schutz (1987) *Nucleic Acids Res* 15:5490), pLNTK (Gorman et al. (1996) *Immunity* 5:241-252), and pBAD/gIII (Stratagene). A preferred host cell is a mammalian cell; more preferably the cell is a Chinese hamster ovary cell, a HeLa cell, a baby hamster kidney cell, or a mouse cell; more preferably the cell is a mouse epididymal cell; even more preferably the cell is a human cell.

Nucleic acids of the present invention can be cloned, synthesized, recombinantly altered, mutagenized, or combinations thereof. Standard recombinant DNA and molecular cloning techniques used to isolate nucleic acids are well known in the art. Exemplary, non-limiting methods are described by Sambrook et al., eds. (1989) “*Molecular Cloning*”, Cold Spring Harbor Laboratory Press, Cold Spring Harbor, N.Y.; by Silhavy et al. (1984) “*Experiments with Gene Fusions*”, Cold Spring Harbor Laboratory Press, Cold Spring Harbor, N.Y.; by. Ausubel et al. (1992) *Current Protocols in Molecular Biology* John Wylie and Sons, Inc. New York; and by Glover, ed. (1985) “*DNA Cloning: A Practical Approach*”, MRL Press, Ltd., Oxford, U.K. Site-specific mutagenesis to create base pair changes, deletions, or small insertions are also well known in the art as exemplified by publications, see, e.g., Adelman et al., (1983) DNA 2:183; Sambrook et al. (1989).

Sequences detected by methods of the invention can be detected, subcloned, sequenced, and further evaluated by any measure well known in the art using any method usually applied to the detection of a specific DNA sequence including but not limited to dideoxy sequencing, PCR, oligomer restriction (Saiki et al., *Bio/Technology* 3:1008-1012 (1985), allele-specific oligonucleotide (ASO) probe analysis (Conner et al. (1983) *Proc. Natl. Acad. Sci. U.S.A.* 80:278), and oligonucleotide ligation assays (OLAs) (Landgren et. al. (1988) *Science* 241:1007). Molecular techniques for DNA analysis have been reviewed (Landgren et. al. (1988) *Science* 242:229-237).

I. B. EP17 Polypeptides

The polypeptides provided by the present invention include the isolated polypeptide of SEQ ID NO:4, polypeptides substantially similar to sequences of SEQ ID NO:4, EP17 polypeptide fragments, fusion proteins comprising EP17 amino acid sequences, biologically functional analogs, and polypeptides that cross-react with an antibody that specifically recognizes an EP17 polypeptide.

The term “isolated”, as used in the context of a polypeptide, indicates that the polypeptide exists apart from its native environment and is not a product of nature. An isolated polypeptide can exist in a purified form or can exist in a non-native environment such as, for example, in a transgenic host cell.

The term “purified”, when applied to a polypeptide, denotes that the polypeptide is essentially free of other cellular components with which it is associated in the natural state. Preferably, a polypeptide is a homogeneous solid or aqueous solution. Purity and homogeneity are typically determined using analytical chemistry techniques such as polyacrylamide gel electrophoresis or high performance liquid chromatography. A polypeptide which is the predominant species present in a preparation is substantially purified. The term “purified” denotes that a polypeptide gives rise to essentially one band in an electrophoretic gel. Particularly, it means that the polypeptide is at least about 50% pure, more preferably at least about 85% pure, and most preferably at least about 99% pure.

The term “substantially identical” in the context of two or more polypeptides sequences is measured by (a) polypeptide sequences having about 35%, or 45%, or preferably from 45-55%, or more preferably 55-65%, or most preferably 65% or greater amino acids which are identical or functionally equivalent. Percent “identity” and methods for determining identity are defined herein below under the heading Nucleotide and Amino Acid Sequence Comparisons.

Substantially identical polypeptides also encompass two or more polypeptides sharing a conserved three-dimensional structure. Computational methods can be used to compare structural representations, and structural superpositions can be generated and easily tuned to identify similarities around important active sites or ligand binding sites. See Henikoff et al. (2000) *Electrophoresis* 21(9):1700-1706; Huang et al. (2000) *Pac Symp Biocomput* 230-241; Saqi et al. (1999) *Bioinformatics* 15(6):521-522; and Barton (1998) *Acta Crystallogr D Biol Crystallogr* 54:1139-1146.

The term "functionally equivalent" in the context of amino acid sequences is well known in the art and is based on the relative similarity of the amino acid side-chain substituents. See Henikoff and Henikoff (2000) *Adv Protein Chem* 54:73-97. Relevant factors for consideration include side-chain hydrophobicity, hydrophilicity, charge, and size. For example, arginine, lysine, and histidine are all positively charged residues; that alanine, glycine, and serine are all of similar size; and that phenylalanine, tryptophan, and tyrosine all have a generally similar shape. By this analysis, described further herein below, arginine, lysine, and histidine; alanine, glycine, and serine; and phenylalanine, tryptophan, and tyrosine; are defined herein as biologically functional equivalents.

In making biologically functional equivalent amino acid substitutions, the hydropathic index of amino acids can be considered. Each amino acid has been assigned a hydropathic index on the basis of their hydrophobicity and charge characteristics, these are: isoleucine (+4.5); valine (+4.2); leucine (+3.8); phenylalanine (+2.8); cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is generally understood in the art (Kyte et al. (1982) *J Mol Biol* 157:105.). It is known that certain amino acids can be substituted for other amino acids having a similar hydropathic index or score and still retain a similar biological activity. In making changes based upon the hydropathic index, the substitution of amino acids whose hydropathic indices are within ±2 of the original value is preferred, those which are within ±1 of the original value are particularly preferred, and those within ±0.5 of the original value are even more particularly preferred.

It is also understood in the art that the substitution of like amino acids can be made effectively on the basis of hydrophilicity. U.S. Pat. No. 4,554,101 states that the greatest local average hydrophilicity of a protein, as governed by the hydrophilicity of its adjacent amino acids, correlates with its immunogenicity and antigenicity, i.e. with a biological property of the protein. It is understood that an amino acid can be substituted for another having a similar hydrophilicity value and still obtain a biologically equivalent protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

In making changes based upon similar hydrophilicity values, the substitution of amino acids whose hydrophilicity values are within ±2 of the original value is preferred, those which are within ±1 of the original value are particularly preferred, and those within ±0.5 of the original value are even more particularly preferred.

The present invention also encompasses EP17 polypeptide fragments or functional portions of an EP17 polypeptide. Such functional portion need not comprise all or substantially all of the amino acid sequence of a native lipocalin gene product. The term "functional" includes any biological activity or feature of EP17, including immunogenicity.

The present invention also includes longer sequences an EP17 polypeptide, or portion thereof. For example, one or more amino acids can be added to the N-terminal or C-terminal of an EP17 polypeptide. Fusion proteins comprising EP17 polypeptide sequences are also provided within the scope of the present invention. Methods of preparing such proteins are known in the art.

The present invention also encompasses functional analogs of an EP17 polypeptide. Functional analogs share at least one biological function with an EP17 polypeptide. An exemplary function is immunogenicity. In the context of amino acid sequence, biologically functional analogs, as used herein, are peptides in which certain, but not most or all, of the amino acids can be substituted. Functional analogs can be created at the level of the corresponding nucleic acid molecule, altering such sequence to encode desired amino acid changes. In one embodiment, changes can be introduced to improve the antigenicity of the protein. In another embodiment, an EP17 polypeptide sequence is varied so as to assess the activity of a mutant EP17 polypeptide.

The present invention also encompasses recombinant production of the disclosed EP17 polypeptides. Briefly, a nucleic acid sequence encoding an EP17 polypeptide, or portion thereof, is cloned into a expression cassette, the cassette is introduced into a host organism, where it is recombinantly produced.

The term "expression cassette" as used herein means a DNA sequence capable of directing expression of a particular nucleotide sequence in an appropriate host cell, comprising a promoter operably linked to the nucleotide sequence of interest which is operably linked to termination signals. It also typically comprises sequences required for proper translation of the nucleotide sequence. The expression cassette comprising the nucleotide sequence of interest can be chimeric. The expression cassette can also be one which is naturally occurring but has been obtained in a recombinant form useful for heterologous expression.

The expression of the nucleotide sequence in the expression cassette can be under the control of a constitutive promoter or an inducible promoter which initiates transcription only when the host cell is exposed to some particular external stimulus. Exemplary promoters include Simian virus 40 early promoter, a long terminal repeat promoter from retrovirus, an action promoter, a heat shock promoter, and a metallothionein protein. In the case of a multicellular organism, the promoter and promoter region can direct expression to a particular tissue or organ or stage of development. Exemplary tissue-specific promoter regions include a mE-RABP promoter and an EP17 promoter, described herein above. Suitable expression vectors which can be used include, but are not limited to, the following vectors or their derivatives: human or animal viruses such as vaccinia virus or adenovirus, yeast vectors, bacteriophage vectors (e.g., lambda phage), and plasmid and cosmid DNA vectors.

The term "host cell", as used herein, refers to a cell into which a heterologous nucleic acid molecule has been introduced. Transformed cells, tissues, or organisms are understood to encompass not only the end product of a transformation process, but also transgenic progeny thereof.

A host cell strain can be chosen which modulates the expression of the inserted sequences, or modifies and processes the gene product in the specific fashion desired. For example, different host cells have characteristic and specific mechanisms for the translational and post-translational processing and modification (e.g., glycosylation, phosphorylation of proteins). Appropriate cell lines or host systems can be chosen to ensure the desired modification and processing of the foreign protein expressed. Expression in a bacterial system can be used to produce a non-glycosylated core protein product. Expression in yeast will produce a glycosylated product. Expression in animal cells can be used to ensure "native" glycosylation of a heterologous protein.

Expression constructs are transfected into a host cell by any standard method, including electroporation, calcium phosphate precipitation, DEAE-Dextran transfection, liposome-mediated transfection, and infection using a retrovirus. The EP17-encoding nucleotide sequence carried in the expression construct can be stably integrated into the genome of the host or it can be present as an extrachromosomal molecule.

Isolated polypeptides and recombinantly produced polypeptides can be purified and characterized using a variety of standard techniques that are well known to the skilled artisan. See, e.g. chapter 16 of Ausubel et al. (1992), Bodanszky, et al. (1976) "*Peptide Synthesis*", John Wiley and Sons, Second Edition, New York., and Zimmer et al. (1993) "*Peptides*" pp. 393-394, ESCOM Science Publishers, B. V.

I. C. Nucleotide and Amino Acid Sequence Comparisons

The terms "identical" or percent "identity" in the context of two or more nucleotide or polypeptide sequences, refer to two or more sequences or subsequences that are the same or have a specified percentage of amino acid residues or nucleotides that are the same, when compared and aligned for maximum correspondence, as measured using one of the sequence comparison algorithms disclosed herein or by visual inspection.

The term "substantially identical" in regards to a nucleotide or polypeptide sequence means that a particular sequence varies from the sequence of a naturally occurring sequence by one or more deletions, substitutions, or additions, the net effect of which is to retain at least some of biological activity of the natural gene, gene product, or sequence. Such sequences include "mutant" sequences, or sequences wherein the biological activity is altered to some degree but retains at least some of the original biological activity. The term "naturally occurring", as used herein, is used to describe a composition that can be found in nature as distinct from being artificially produced by man. For example, a protein or nucleotide sequence present in an organism, which can be isolated from a source in nature and which has not been intentionally modified by man in the laboratory, is naturally occurring.

For sequence comparison, typically one sequence acts as a reference sequence to which test sequences are compared. When using a sequence comparison algorithm, test and reference sequences are entered into a computer program, subsequence coordinates are designated if necessary, and sequence algorithm program parameters are selected. The sequence comparison algorithm then calculates the percent sequence identity for the designated test sequence(s) relative to the reference sequence, based on the selected program parameters.

Optimal alignment of sequences for comparison can be conducted, e.g., by the local homology algorithm of Smith and Waterman (1981) *Adv Appl Math* 2:482, by the homology alignment algorithm of Needleman and Wunsch (1970) *J Mol Biol* 48:443, by the search for similarity method of Pearson and Lipman (1988) *Proc Natl Acad Sci USA* 85:2444, by computerized implementations of these algorithms (GAP, BESTFIT, FASTA, and TFASTA in the Wisconsin Genetics Software Package, Genetics Computer Group, Madison, Wis.), or by visual inspection (See generally, Ausubel et al. (1992)).

A preferred algorithm for determining percent sequence identity and sequence similarity is the BLAST algorithm, which is described in Altschul et al. (1990) *J Mol Biol* 215: 403-410. Software for performing BLAST analyses is publicly available through the National Center for Biotechnology Information (http://wvw.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached. The BLAST algorithm parameters W, T, and X determine the sensitivity and speed of the alignment. The BLASTN program (for nucleotide sequences) uses as defaults a wordlength W=11, an expectation E=10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix. See Henikoff and Henikoff (1989) *Proc Natl Acad Sci USA* 89:10915.

In addition to calculating percent sequence identity, the BLAST algorithm also performs a statistical analysis of the similarity between two sequences. See, e.g., Karlin and Altschul (1993) *Proc Natl Acad Sci USA* 90:5873-5887. One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, more preferably less than about 0.01, and most preferably less than about 0.001.

I. D. Antibodies

The present invention also provides an antibody immunoreactive with an EP17 polypeptide. The term "antibody" indicates an immunoglobulin protein, or functional portion thereof, including a polyclonal antibody, a monoclonal antibody, a chimeric antibody, a single chain antibody, Fab fragments, and an Fab expression library. "Functional portion"

refers to the part of the protein that binds a molecule of interest. In a preferred embodiment, an antibody of the invention is a monoclonal antibody. Techniques for preparing and characterizing antibodies are well known in the art (See, e.g., Harlow and Lane (1988) "*Antibodies: A Laboratory Manual*" Cold Spring Harbor Laboratory Press, Cold Spring Harbor, N.Y.). A monoclonal antibody of the present invention can be readily prepared through use of well-known techniques such as the hybridoma techniques exemplified in U.S. Pat. No. 4,196,265 and the phage-displayed techniques disclosed in U.S. Pat. No. 5,260,203.

The phrase "specifically (or selectively) binds to an antibody", or "specifically (or selectively) immunoreactive with", when referring to a protein or peptide, refers to a binding reaction which is determinative of the presence of the protein in a heterogeneous population of proteins and other biological materials. Thus, under designated immunoassay conditions, the specified antibodies bind to a particular protein and do not show significant binding to other proteins present in the sample. Specific binding to an antibody under such conditions can require an antibody that is selected for its specificity for a particular protein. For example, antibodies raised to a protein with an amino acid sequence encoded by any of the nucleic acid sequences of the invention can be selected to obtain antibodies specifically immunoreactive with that protein and not with unrelated proteins.

The use of a molecular cloning approach to generate antibodies, particularly monoclonal antibodies, and more particularly single chain monoclonal antibodies, are also provided. The production of single chain antibodies has been described in the art. See, e.g., U.S. Pat. No. 5,260,203. For this approach, combinatorial immunoglobulin phagemid libraries are prepared from RNA isolated from the spleen of the immunized animal, and phagemids expressing appropriate antibodies are selected by panning on endothelial tissue. The advantages of this approach over conventional hybridoma techniques are that approximately $10^4$ times as many antibodies can be produced and screened in a single round, and that new specificities are generated by heavy (H) and light (L) chain combinations in a single chain, which further increases the chance of finding appropriate antibodies. Thus, an antibody of the present invention, or a "derivative" of an antibody of the present invention, pertains to a single polypeptide chain binding molecule which has binding specificity and affinity substantially similar to the binding specificity and affinity of the light and heavy chain aggregate variable region of an antibody described herein.

The term "immunochemical reaction", as used herein, refers to any of a variety of immunoassay formats used to detect antibodies specifically bound to a particular protein, including but not limited to, competitive and non-competitive assay systems using techniques such as radioimmunoassays, ELISA (enzyme linked immunosorbent assay), "sandwich" immunoassays, immunoradiometric assays, gel diffusion precipitin reactions, immunodiffusion assays, in situ immunoassays (e.g., using colloidal gold, enzyme or radioisotope labels), western blots, precipitation reactions, agglutination assays (e.g., gel agglutination assays, hemagglutination assays), complement fixation assays, immunofluorescence assays, protein A assays, and immunoelectrophoresis assays, etc. See Harlow and Lane (1988) for a description of immunoassay formats and conditions.

I. E. Protein Binding Assays

The term "binding" refers to an affinity between two molecules, for example, a ligand and a receptor, means a preferential binding of one molecule for another in a mixture of molecules. The binding of the molecules can be considered specific if the binding affinity is about $1\times10^4$ $M^{-1}$ to about $1\times10^6$ $M^{-1}$ or greater. Binding of two molecules also encompasses a quality or state of mutual action such that an activity of one protein or compound on another protein is inhibitory (in the case of an antagonist) or enhancing (in the case of an agonist).

Fluorescence Correlation Spectroscopy (FCS) theory was developed in 1972 but it is only in recent years that the technology to perform FCS became available (Madge et al. (1972) *Phys Re. Lett* 29:705-708; Maiti et al. (1997) *Proc Natl Acad Sci USA,* 94: 11753-11757). FCS measures the average diffusion rate of a fluorescent molecule within a small sample volume. The sample size can be as low as $10^3$ fluorescent molecules and the sample volume as low as the cytoplasm of a single bacterium. The diffusion rate is a function of the mass of the molecule and decreases as the mass increases. FCS can therefore be applied to protein-ligand interaction analysis by measuring the change in mass and therefore in diffusion rate of a molecule upon binding. In a typical experiment, the target to be analyzed is expressed as a recombinant protein with a sequence tag, such as a poly-histidine sequence, inserted at the N-terminus or C-terminus. The expression takes place in *E. coli*, yeast or mammalian cells. The protein is purified by chromatography. For example, the poly-histidine tag can be used to bind the expressed protein to a metal chelate column such as Ni2+ chelated on iminodiacetic acid agarose. The protein is then labeled with a fluorescent tag such as carboxytetramethylrhodamine or BODIPY™ (Molecular Probes, Eugene, Oreg.). The protein is then exposed in solution to the potential ligand, and its diffusion rate is determined by FCS using instrumentation available from Carl Zeiss, Inc. (Thornwood, N.Y.). Ligand binding is determined by changes in the diffusion rate of the protein.

Surface-Enhanced Laser Desorption/Ionization (SELDI) was invented by Hutchens and Yip (1993) *Rapid Commun Mass Spectrom* 7:576-580). When coupled to a time-of-flight mass spectrometer (TOF), SELDI provides means to rapidly analyze molecules retained on a chip. It can be applied to ligand-protein interaction analysis by covalently binding the target protein on the chip and analyze by MS the small molecules that bind to this protein (Worrall et al. (1998) *Anal. Biochem.* 70: 750-756). In a typical experiment, the target to be analyzed is expressed as described for FCS. The purified protein is then used in the assay without further preparation. It is bound to the SELDI chip either by utilizing the poly-histidine tag or by other interaction such as ion exchange or hydrophobic interaction. The chip thus prepared is then exposed to the potential ligand via, for example, a delivery system able to pipet the ligands in a sequential manner (autosampler). The chip is then submitted to washes of increasing stringency, for example a series of washes with buffer solutions containing an increasing ionic strength. After each wash, the bound material is analyzed by submitting the chip to SELDI-TOF. Ligands that specifically bind the target are identified by the stringency of the wash needed to elute them.

Biacore relies on changes in the refractive index at the surface layer upon binding of a ligand to a protein immobilized on the layer. In this system, a collection of small ligands is injected sequentially in a 2-5 microliter cell, wherein the protein is immobilized within the cell. Binding is detected by surface plasmon resonance (SPR) by recording laser light refracting from the surface. In general, the refractive index change for a given change of mass concentration at the surface layer is practically the same for all proteins and peptides, allowing a single method to be applicable for any protein (Liedberg et al. (1983) *Sensors Actuators* 4:299-304; Malmquist (1993) *Nature* 361:186-187). In a typical experiment, the target to be analyzed is expressed as described for FCS. The purified protein is then used in the assay without further preparation. It is bound to the Biacore chip either by utilizing the poly-histidine tag or by other interaction such as ion exchange or hydrophobic interaction. The chip thus prepared is then exposed to the potential ligand via the delivery system incorporated in the instruments sold by Biacore (Uppsala, Sweden) to pipet the ligands in a sequential manner (autosampler). The SPR signal on the chip is recorded and changes in the refractive index indicate an interaction between the immobilized target and the ligand. Analysis of the signal kinetics on rate and off rate allows the discrimination between non-specific and specific interaction.

I. F. Transgenic animals

It is also within the scope of the present invention to prepare a transgenic animal to mutagenize the EP17 locus or to express a transgene comprising nucleic acid sequences of the present invention. The term "transgenic animal", indicates an animal comprising a germline insertion of a heterologous nucleic acid. Transgenic animals of the present invention are understood to encompass not only the end product of a transformation method, but also transgenic progeny thereof.

The term "transgene", as used herein indicates a heterologous nucleic acid molecule that has been transformed into a host cell. For intended use in the creation of a transgenic animal, the transgene includes genomic sequences of the host organism at a selected locus or site of transgene integration to mediate a homologous recombination event. A transgene further comprises nucleic acid sequences of interest, for example a targeted modification of the gene residing within the locus, a reporter gene, or a expression cassette, each defined herein above.

Transgene integration can be used to create gene mutations, including "knock-out", "knock-in", or a "knock-down" mutations. The term "knock-out" refers to a homologous recombination event that renders a gene inactive. Gene knock-out is generally accomplished by integration of the transgene at a chromosomal loci, thereby interrupting a gene residing at that loci. The term "knock-in" refers to in vivo replacement at a targeted locus. Knock-in mutations can modify a gene sequence to create a loss-of-function or gain-of-function mutation. The term "gene knock-down" refers to a homologous recombination event wherein the transgene partially eliminates gene function. A knock-down animal can be created by transgenic expression of an antisense molecule, wherein a transgene comprising the antisense sequence and a relevant promoter are integrated into the genome at a nonessential loci. Expression of the antisense or ribozyme molecule disrupts the corresponding gene function, although this disruption is generally incomplete (Luyckx et al. (1999) *Proc Natl Acad Sci USA* 96(21):12174-12179).

Conditional mutation can be accomplished using transgenic methods in combination with the Cre-recombinase system in mice. Briefly, in one instance, a transgenic mouse is derived that expresses Cre-recombinase under the direction of an inducible promoter. A second transgenic mouse bears a mutation of a gene of interest as well as a lox-P-flanked endogenous gene sequence. Such transgenic mice are mated, the resulting progeny having both the Cre-recombinase and lox-P-flanked transgenes. Induction of Cre recombinase catalyzes excision of the lox-P-flanked transgene, thereby excising a portion of the endogenous gene sequence and revealing the mutated sequence. Conditional knockout can be varied according to the temporal and spatial features of Cre recombinase expression, inherent in the selection of a promoter to drive Cre recombinase. See Postic et al. (1999) *J Biol Chem* 275(1):305-315; and Sauer (1998) *Methods* 14(4):381-392.

Transgenes can also be used for heterologous expression in a host organism without generating phenotypically apparent mutations. By this method, nucleotide sequences of interest are introduced into the genome at a nonessential loci, whereby insertion alone does not disrupt an essential gene function.

Techniques for the preparation of transgenic animals are known in the art. Exemplary techniques are described in U.S. Pat. No. 5,489,742 (transgenic rats); U.S. Pat. Nos. 4,736,866, 5,550,316, 5,614,396, 5,625,125 and 5,648,061 (transgenic mice); U.S. Pat. No. 5,573,933 (transgenic pigs); U.S. Pat. No. 5,162,215 (transgenic avian species) and U.S. Pat. No. 5,741,957 (transgenic bovine species). Briefly, nucleotide sequences of interest are cloned into a vector (e.g., pLNK—Gorman et al. 1996), and the construct is transformed into a germ cell. In the germ cell, a chromosomal rearrangement event takes place wherein the nucleic acid sequences of interest are integrated into the genome of the germ cell by homologous recombination. Fertilization and propagation of the transformed germ cell results in a transgenic animal. Homozygosity of the mutation is accomplished by intercrossing.

I. G. Therapeutic Methods

The present invention further provides methods for discovering substances that can be used as pharmaceutical compositions. The term "pharmaceutical composition" or "drug" as used herein, each refer to any substance having a biological activity. Substances discovered by methods of the present invention include but are not limited to polypeptide, proteins, peptides, chemical compounds, and antibodies.

A composition of the present invention is typically formulated using acceptable vehicles, adjuvants, and carriers as desired.

Among the acceptable vehicles and solvents that can be employed are water, Ringer's solution, and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid find use in the preparation of injectable compositions.

Injectable preparations, for example sterile injectable aqueous or oleaginous suspensions, are formulated according to the known art using suitable dispersing or wetting agents and suspending agents. The sterile injectable preparation can also be a sterile injectable solution or suspension in a nontoxic diluent or solvent, for example, as a solution in 1,3-butanediol.

A vector can be used as a carrier, for example an adenovirus vector, can be used for gene therapy methods. The vector is purified to sufficiently render it essentially free of undesirable contaminants, such as defective interfering adenovirus particles or endotoxins and other pyrogens such that it does not cause any untoward reactions in the individual receiving the vector construct. A preferred means of purifying the vector involves the use of buoyant density gradients, such as cesium chloride gradient centrifugation.

A transfected cell can also serve as a carrier. By way of example, a liver cell can be removed from an organism, transfected with a nucleic acid sequence of the present invention using methods set forth above and then the transfected cell returned to the organism (e.g. injected intra-vascularly).

Monoclonal antibodies or polypeptides of the invention can be administered parenterally by injection or by gradual infusion over time. Although the tissue to be treated can typically be accessed in the body by systemic administration and therefore most often treated by intravenous administration of therapeutic compositions, other tissues and delivery means are provided where there is a likelihood that the tissue targeted contains the target molecule and are known to those of skill in the art.

Representative antibodies for use in the present invention are intact immunoglobulin molecules, substantially intact immunoglobulin molecules, single chain immunoglobulins or antibodies, those portions of an immunoglobulin molecule that contain the paratope, including antibody fragments. It is contemplated to be within the scope of the present invention that a monovalent modulator can optionally be used.

Methods of preparing "humanized" antibodies are generally well known in the art, and can readily be applied to the antibodies of the present invention. Humanized monoclonal antibodies offer particular advantages over monoclonal antibodies derived from other mammals, particularly insofar as they can be used therapeutically in humans. Specifically, humanized antibodies are not cleared from the circulation as rapidly as "foreign" antigens, and do not activate the immune system in the same manner as foreign antigens and foreign antibodies.

With respect to the therapeutic methods of the present invention, a preferred subject is a vertebrate subject. A preferred vertebrate is warm-blooded; a preferred warm-blooded vertebrate is a mammal. A preferred mammal is a mouse or, most preferably, a human. As used herein and in the claims, the term "patient" includes both human and animal patients. Thus, veterinary therapeutic uses are provided in accordance with the present invention.

Also provided is the treatment of mammals such as humans, as well as those mammals of importance due to being endangered, such as Siberian tigers; of economical importance, such as animals raised on farms for consumption by humans; and/or animals of social importance to humans, such as animals kept as pets or in zoos. Examples of such animals include but are not limited to: carnivores such as cats and dogs; swine, including pigs, hogs, and wild boars; ruminants and/or ungulates such as cattle, oxen, sheep, giraffes, deer, goats, bison, and camels; and horses. Also provided is the treatment of birds, including the treatment of those kinds of birds that are endangered and/or kept in zoos, as well as fowl, and more particularly domesticated fowl, i.e., poultry, such as turkeys, chickens, ducks, geese, guinea fowl, and the like, as they are also of economical importance to humans. Thus, provided is the treatment of livestock, including, but not limited to, domesticated swine, ruminants, ungulates, horses, poultry, and the like.

As used herein, the term "experimental subject" refers to any subject or sample in which the desired measurement is unknown. The term "control subject" refers to any subject or sample in which a desired measure is unknown.

As used herein, an "effective" dose refers to one a dose(s) administered to an individual patient sufficient to cause a change in EP17 activity. After review of the disclosure herein of the present invention, one of ordinary skill in the art can tailor the dosages to an individual patient, taking into account the particular formulation and method of administration to be used with the composition as well as patient height, weight, severity of symptoms, and stage of the biological condition to be treated. Such adjustments or variations, as well as evaluation of when and how to make such adjustments or variations, are well known to those of ordinary skill in the art of medicine.

A therapeutically effective amount can comprise a range of amounts. One skilled in the art can readily assess the potency and efficacy of an EP17 modulator of this invention and adjust the therapeutic regimen accordingly. A modulator of EP17 biological activity can be evaluated by a variety of means including the use of a responsive reporter gene, interaction of lipocalin polypeptides with a monoclonal antibody, and fertility assays, each technique described herein.

Additional formulation and dose techniques have been described in the art, see for example, those described in U.S. Pat. Nos. 5,326,902 and 5,234,933, and PCT Publication WO 93/25521.

For the purposes described above, the identified substances can normally be administered systemically, parenterally, or orally. The term "parenteral" as used herein includes intravenous, intra-muscular, intra-arterial injection, or infusion techniques. Other compositions for administration include liquids for external use, and endermic liniments (ointment, etc.), suppositories, and pessaries which comprise one or more of the active substance(s) and can be prepared by known methods.

II. CLONING AND EXPRESSION OF THE MOUSE EP17 GENE

The present co-inventors have identified a new lipocalin, mEP17, that is adjacent to a related lipocalin-encoding gene, mE-RABP, on mouse chromosome 2 (FIG. 1). The genomic organization of the mEP17 gene was determined by prediction of exons within a BAC genomic clone and further supported by cloning of the mEP17 cDNA (Lareyre et al., 2001). FIG. 1 depicts the genomic organization of the mEP17 locus. Exon sizes are indicated in nucleotides. The major transcription initiation sites of both genes are represented with broken arrows. Primer FwMEP17cDNA (SEQ ID NO:7) was used for primer extension analysis, as described herein below. The G-X-W and T-D-Y and motifs and two cysteine residues (C) are also indicated.

Figure 9:
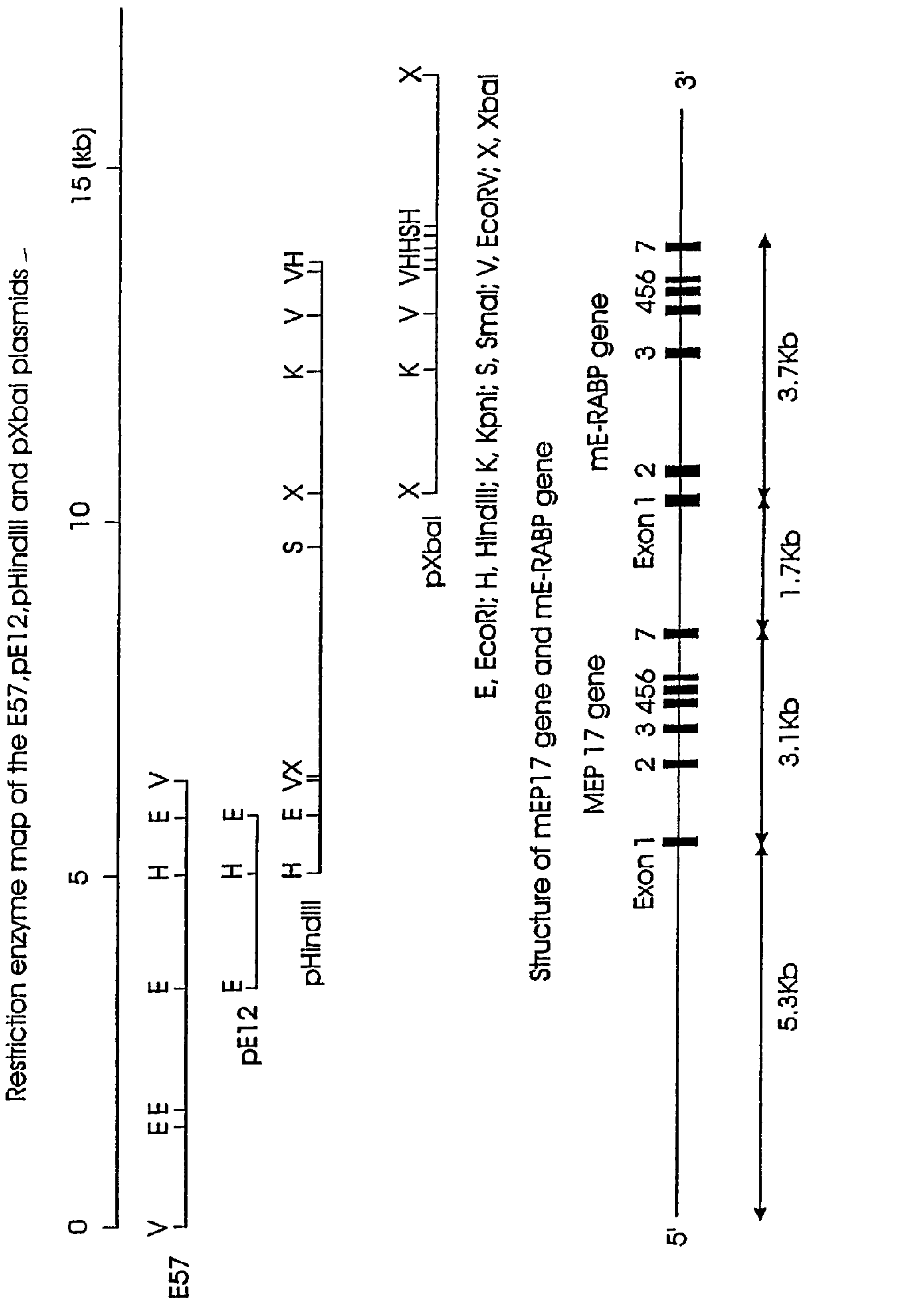
FIG. 9 depicts a restriction enzyme map of plasmids derived from BAC clone 10983 aligned with the mEP17/mE-RABP genomic region. The promoter region of mEP17, mEP17 exons, the intergenic region, and mE-RABP exons are indicated.

To isolate the mEP17 promoter region, two clones containing 6.3 kb EcoRV restriction fragments within the 5' flanking region were isolated from the genomic BAC clone 10983 (FIG. 9). DNA sequencing analysis of both clones revealed that the 6.3 kb fragment contains 5.4 kb of the 5' flanking region of the mEP17 gene. Cloning methods are provided in Example 1.

Figures 2A, 2B:
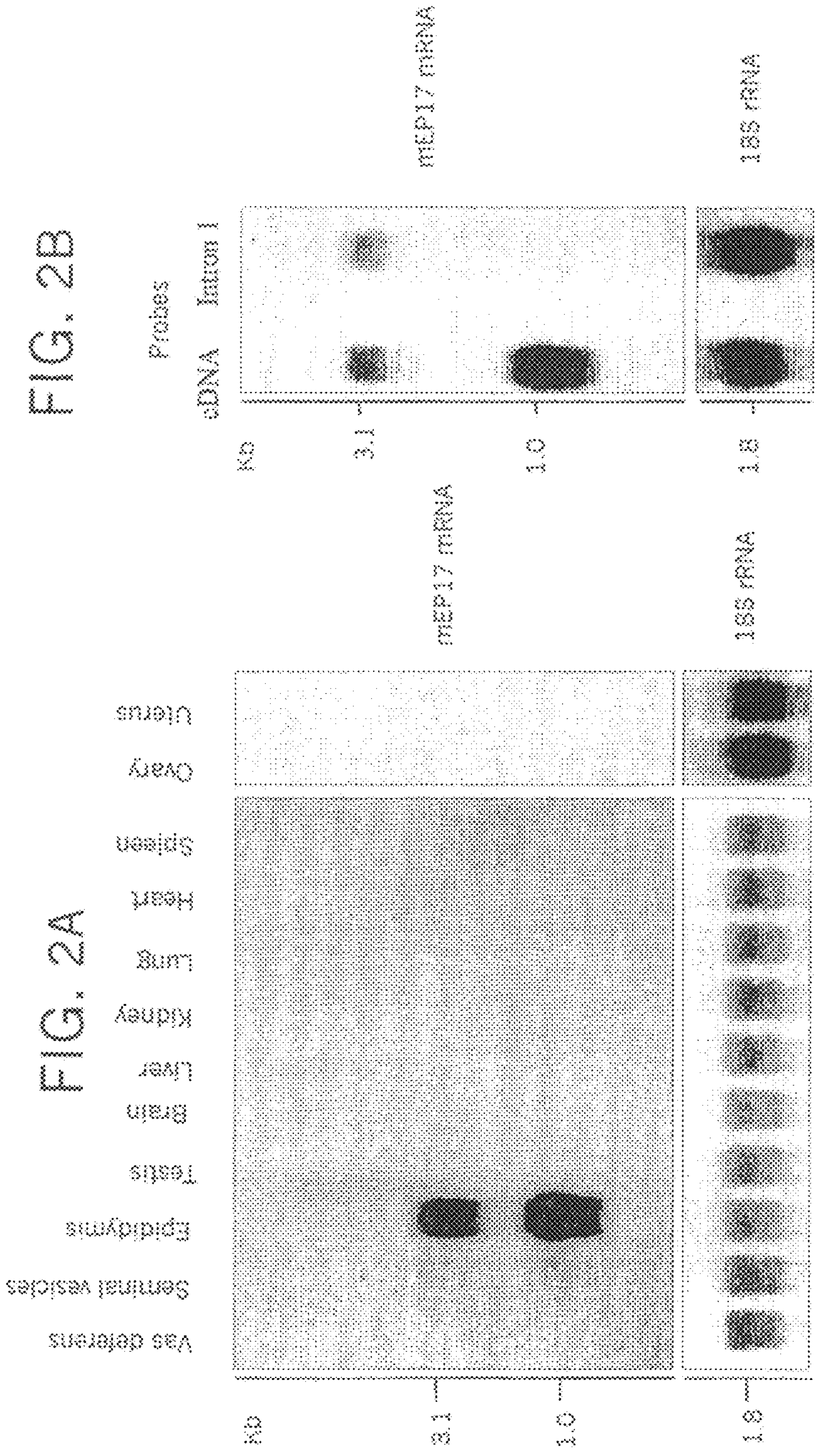
FIG. 2A presents a Northern blot showing epididymis-specific expression of the mEP17 gene. Total RNA was extracted from individual tissues and hybridized with [$^{32}$P]-labeled mEP17 cDNA. Two major transcripts of 1 kb and 3.1 kb in size were detected only in the epididymis.
FIG. 2B shows Northern blot analysis of total RNA extracted from the epididymis, hybridized with [$^{32}$P]-labeled intron 1 of the mEP17 gene or with [$^{32}$P]-labeled mEP17 cDNA used as probes. The intron 1 probe only detected the 3.1 kb transcripts, suggesting that these transcripts are likely unspliced mEP17 precursor RNA.

The tissue distribution of mRNA encoding the mEP17 protein was examined by Northern blot analysis of total RNA from twelve different tissues, including spleen, liver, heart, lung, brain, kidney, testis, epididymis, vas deferens, seminal vesicles, uterus, and ovary (FIG. 2A). Hybridization of Northern blots with a [$^{32}$P]-radiolabeled mEP17 cDNA probe revealed two RNA species of about 3.1 kb and 1 kb only in the epididymis. The total length of the mEP17 gene, including exons and intron, is 3.1 kb. To determine whether the 3.1 kb RNA could be the precursor RNA, two epididymal RNA samples were run side by side and hybridized individually with the cDNA probe or with a probe encompassing intron I of the mEP17 gene (FIG. 2B). The first intron 1 probe hybridized with the 3.1 kb RNA but not the 1 kb RNA, indicating that the 3.1 kb RNA is an unspliced precursor RNA.

Figure 3:
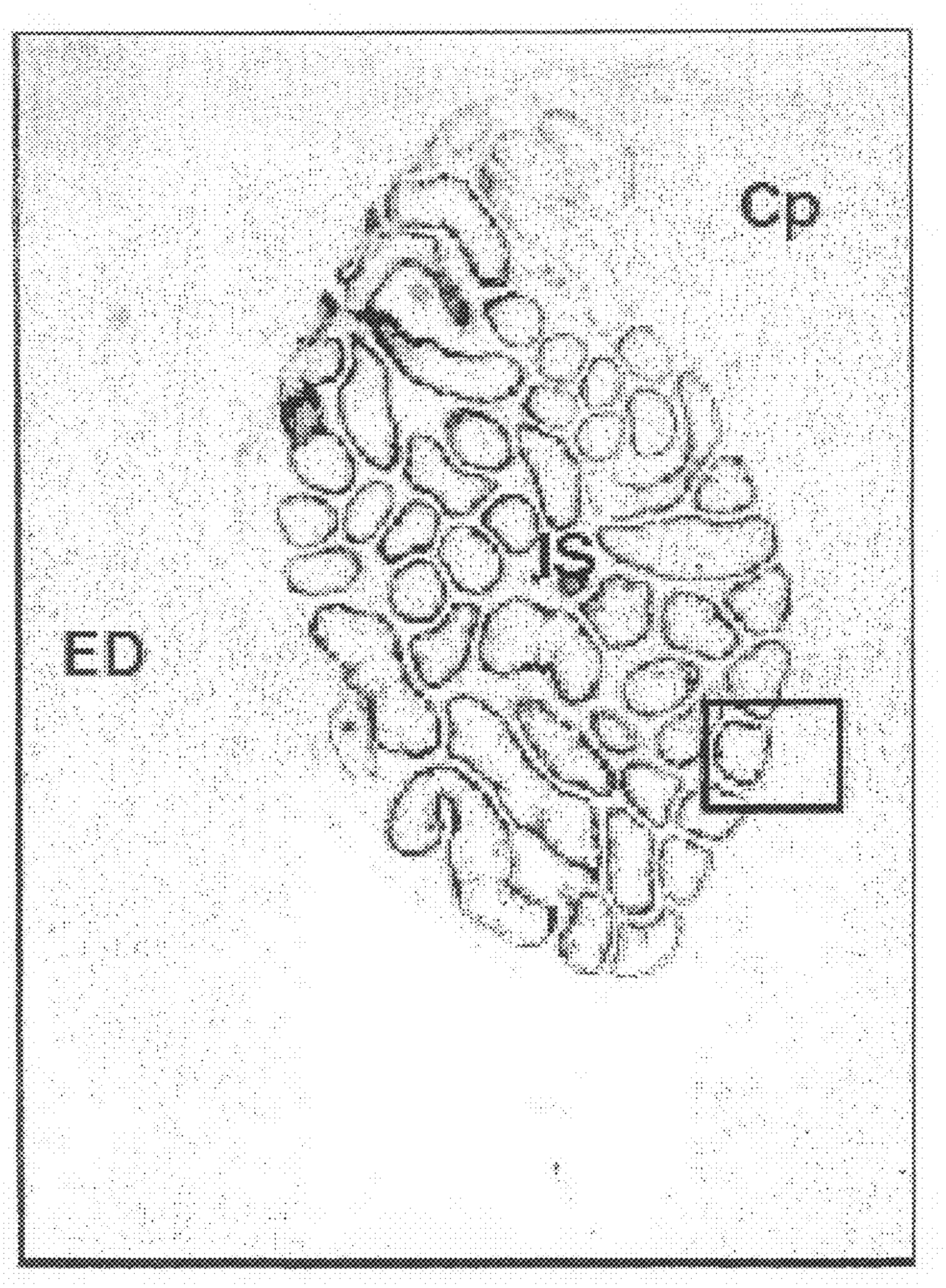
FIG. 3 shows region-specific expression of the mEP17 gene in the initial segment of the epididymis. In situ hybridization of mEP17 transcripts is detected in the initial segment (IS) but not in the efferent duct (ED) and mid/distal caput epididymis (Cp).
Figure 4:
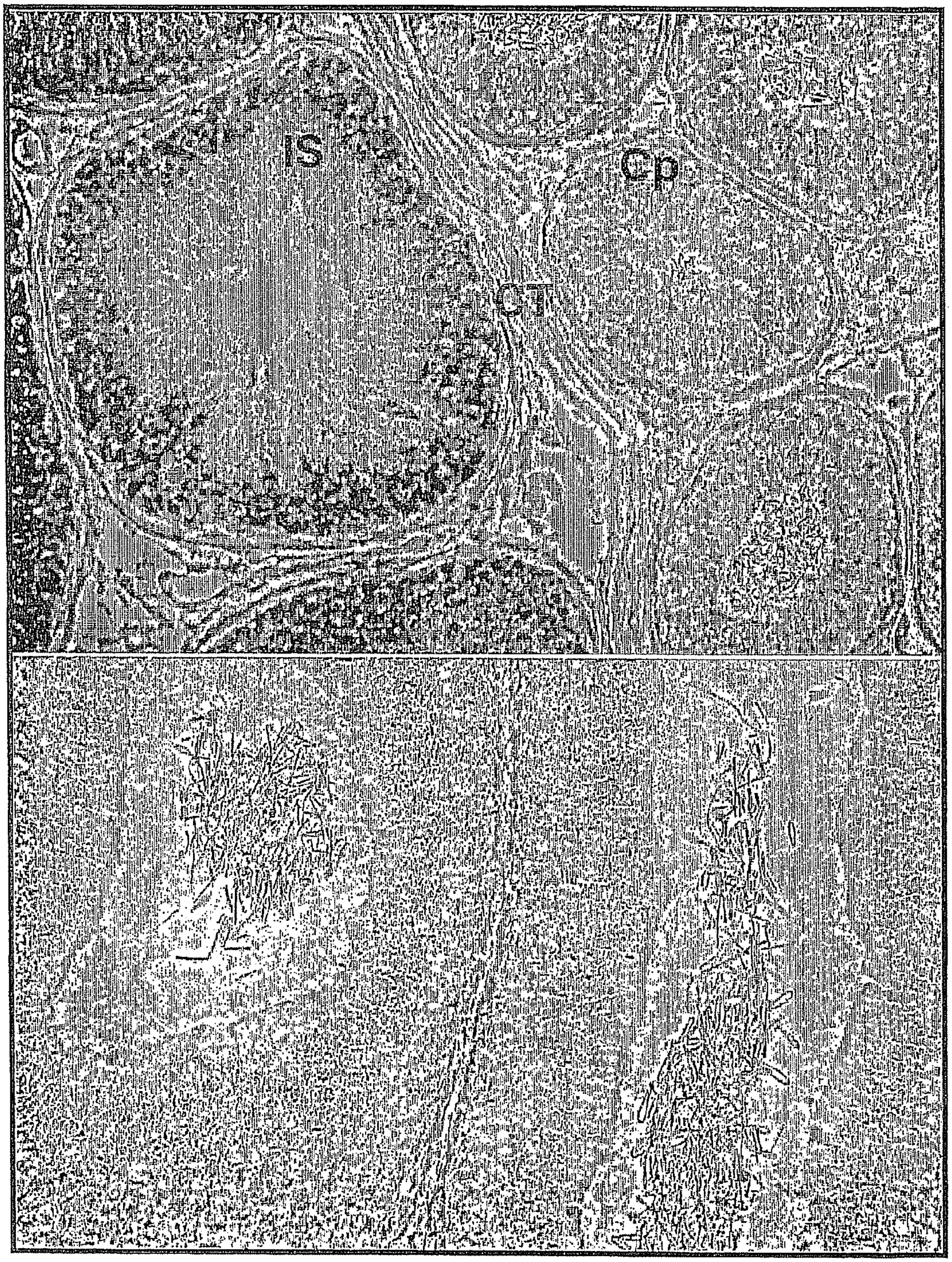
FIGS. 4A and 4B show in situ hybridization of mEP17 in epididymal tissue, and also show cell-specific expression of the mEP17 gene.

To investigate the tissue-, region-, and cell-specific profile of gene expression, in situ hybridization of mEP17 transcripts was carried out using sense and antisense digoxygenin-labeled riboprobes generated from mEP17 cDNA (FIGS. 3 and 4*a*), as described in Example 2 below. mEP17 mRNA was detected only in the principal cells of the initial segment of the epididymis and is localized basally. Hybridization was not detected when the sense riboprobe was used (FIG. 4B). mEP17 gene expression was high throughout the initial segment (IS). A checkerboard pattern was observed at the boundary between the initial segment and the proximal caput epididymis, wherein some cells expressed mEP17 and some cells did not. mEP17 mRNA was not detected in the efferent ducts (ED), mid and distal caput (Cp), corpus and cauda epididymis using sense or antisense probes.

III. ISOLATION OF HUMAN EP17

The present invention also provides a human EP17 gene. Preferably, the human EP17 gene comprises the sequence set forth as SEQ ID:2, a nucleic acid molecule that is substantially similar to SEQ ID NO:2, or a nucleic acid molecule comprising a 20 base pair nucleotide sequence that is identical to a contiguous 20 base pair sequence of SEQ ID NO:2.

The mouse EP17 sequence was used to query databases of human genomic sequence, including GenBank and proprietary databases of Celera Genomics Corp. (Rockville, Md.). Two DNA fragments derived from human chromosome 9 were identified (Accession numbers AL35598.7 and 449-425.3) in GenBank, although neither sequence or the combination of the sequences predicts the hEP17 gene. A genomic region having sequences corresponding to the hEP17 gene was also identified in Celera's database (Accession number GA 65 373998). The genomic sequence derived from Celera's database was unannotated and did not predict the hEP17 gene.

Figure 5:
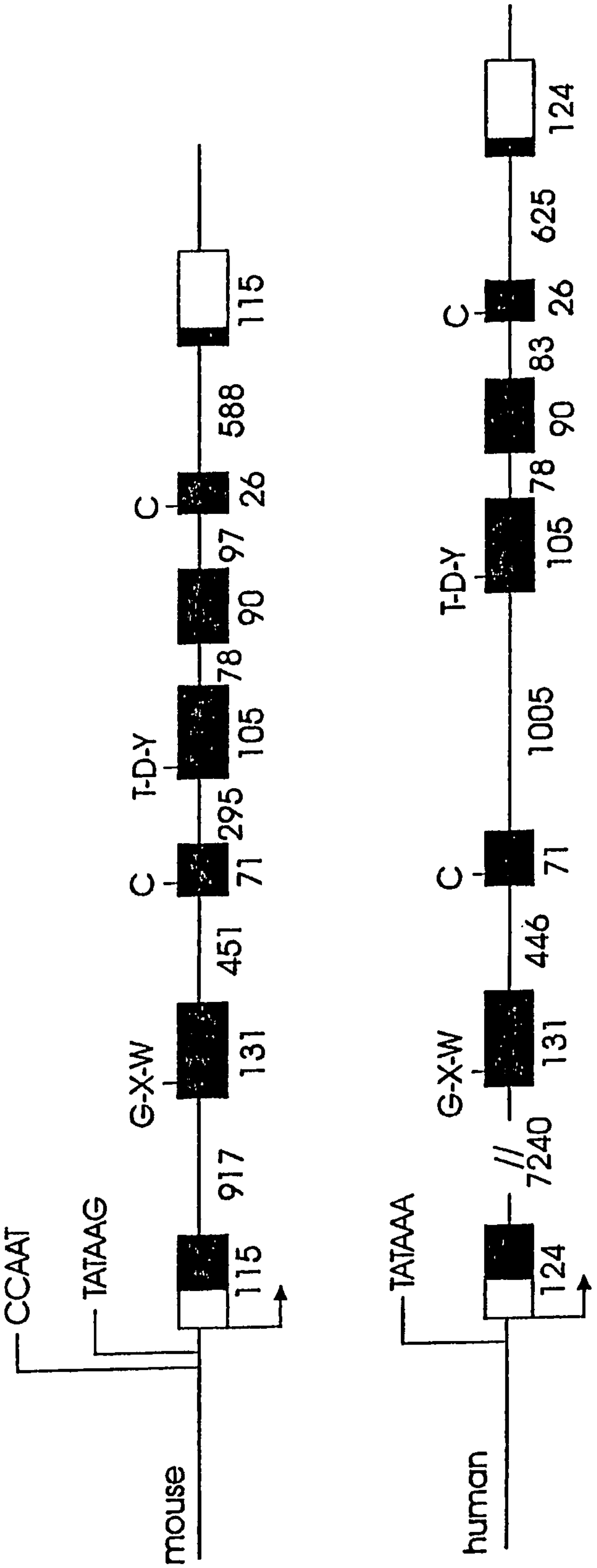
FIG. 5 presents a comparison of the genomic structure of the mouse and human EP17 genes. The major transcription initiation sites (TIS) of both genes are indicated by broken arrows. The lipocalin-specific motifs (G-X-W, T-D-Y, and 2 cysteine residues) are also indicated. Black boxes indicate exons, and the line region between the boxes indicate introns. Numbers below the boxes and line regions indicate exon and intron sizes in base pairs.

The hEP17 gene disclosed herein (SEQ ID NO:2) was predicted by comparing unannotated genomic sequence and the gene structure of mouse EP17. Conserved intron/exon boundaries and conserved nucleotide sequence were recognized and used to construct the gene map depicted in FIG. 5 and Table 1. Preferably, the human EP17 gene comprises a coding region and a promoter region set forth as SEQ ID NOs:3 and 5, respectively.

TABLE 1

| Feature | base pairs from | to |
|---|---|---|
| Exon 1 | 5160 | 5255 |
| Intron 1 | 5256 | 12495 |
| Exon 2 | 12496 | 12626 |
| Intron 2 | 12627 | 13072 |
| Exon 3 | 13073 | 13143 |
| Intron 3 | 13144 | 14148 |
| Exon 4 | 14149 | 14253 |
| Intron 4 | 14254 | 14331 |
| Exon 5 | 14332 | 14421 |
| Intron 5 | 14422 | 14504 |
| Exon 6 | 14505 | 14530 |
| Intron 6 | 14531 | 15155 |
| Exon 7 | 15156 | 15279 |

Figure 7:
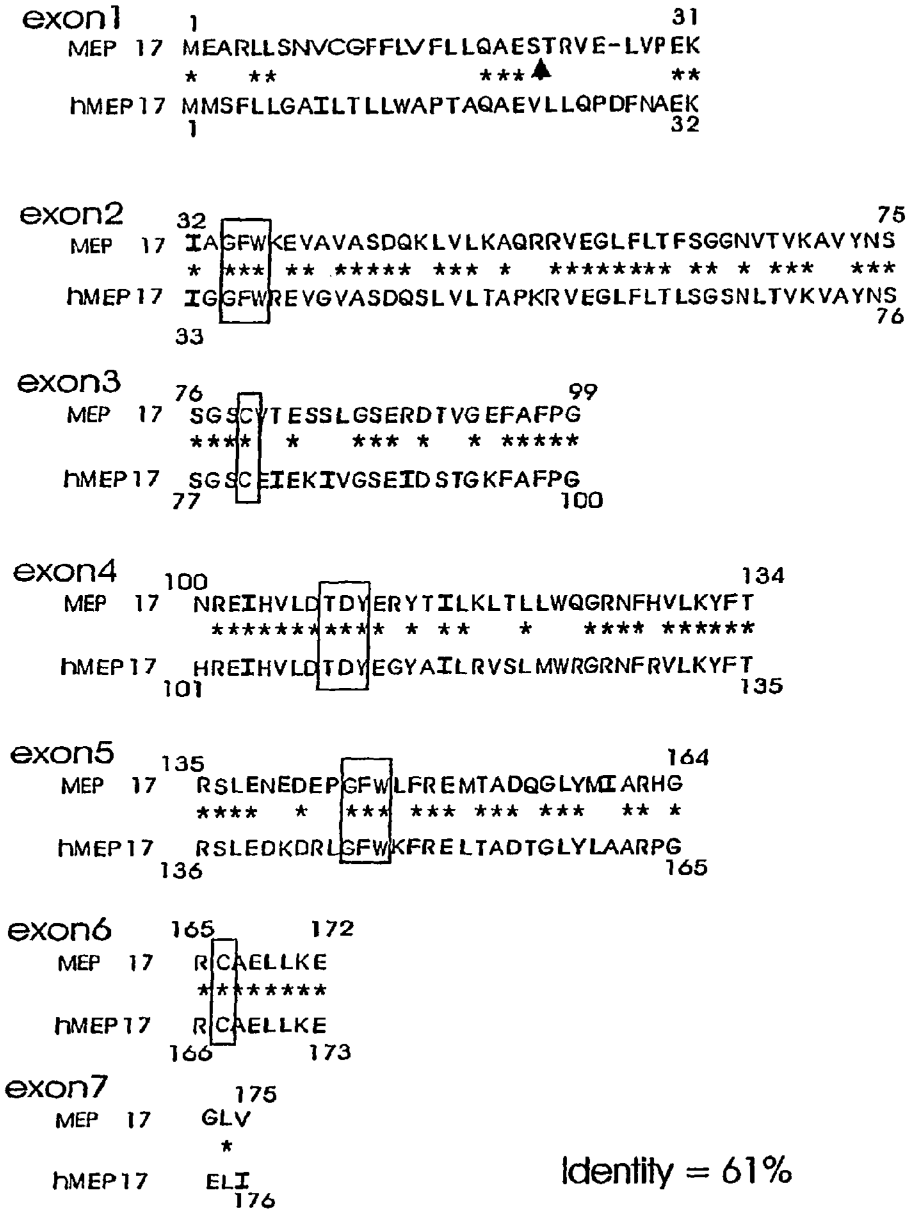
FIG. 7 presents a comparison of the amino acid sequences of mouse EP17 and human EP17 proteins. Conserved lipocalin motifs are indicated. The mouse and human EP17 proteins share 61% overall identity.

The predicted hEP17 gene displays sequence homology with other lipocalins, most notably with m-ERABP and prostaglandin $H_2$-D isomerases s (FIG. 6). The mouse and human EP17 proteins share 61% overall identity and have conserved lipocalin motifs (G-X-W, T-D-Y, and two cysteine residues) at similar positions (FIG. 7).

Figure 8A:
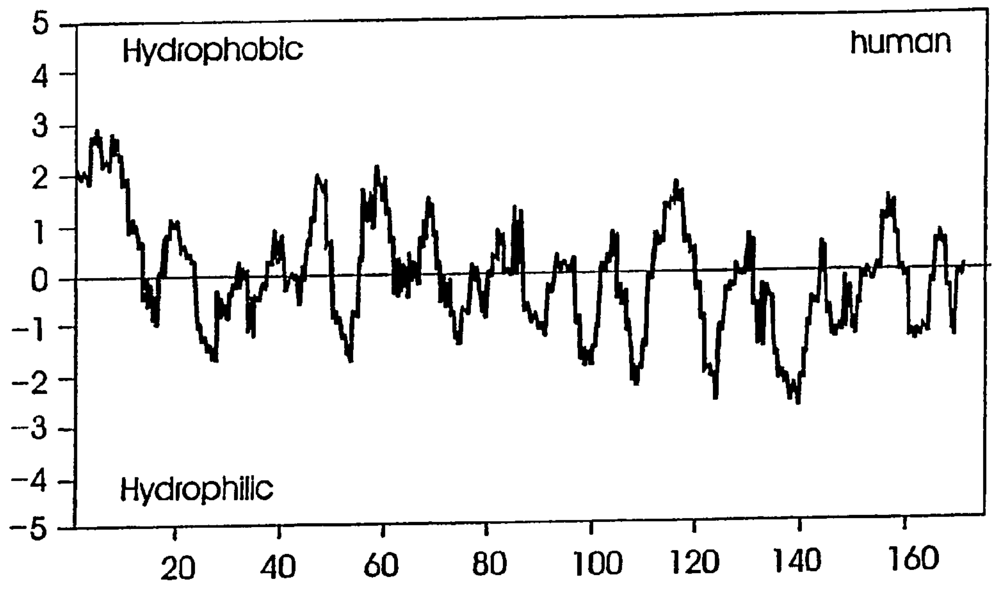
FIG. 8 shows hydropathic analysis of the murine and human EP17 proteins.
Figure 8B:
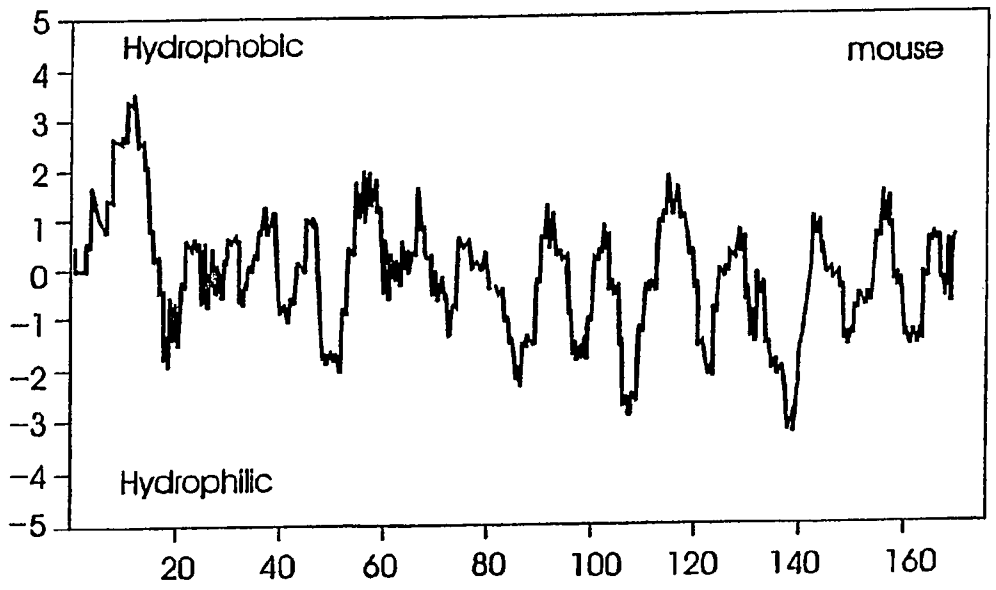

The amino terminal regions of both mouse and human EP17 proteins are predicted to be a signal peptide since in each case the region is highly hydrophobic, similar to the signal peptide of the mE-RABP protein, and in agreement with the sliding window/matrix scoring method and −1, −3 rule for predicting a peptide cleavage (von Heiji (1986) *Nucleic Acid Res* 14:4683-4690) (FIG. 8). This observation implies that the human and mouse EP17 genes encode secreted proteins.

IV. CHARACTERIZATION OF AN EP17 PROMOTER REGION

Figure 10:
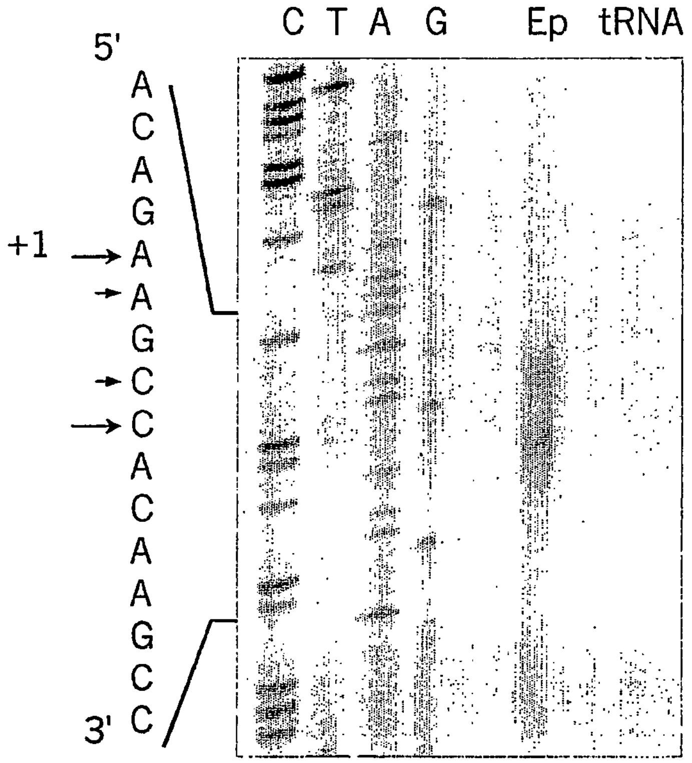
FIG. 10 shows primer extension analysis of the 5' end of mEP17 mRNA. Total RNA extracted from the epididymis (Ep) or transfer (t) RNA was reverse transcribed with [$^{32}$P]-radiolabeled mEP17PE2 primer (SEQ ID NO:7) and extended using Avian Myeloblastosis virus (AMV) reverse transcriptase. Lanes labeled "C", "T", "A" and "G" are [$^{35}$S]-radiolabeled DNA sequencing reactions carried out using the mEP17PE2 primer (SEQ ID NO:7) and the pHindIII clone (indicated in FIG. 9) as template. The localization of two major (arrows) and two minor (arrowheads) transcription initiation sites are indicated.

The transcription initiation sites of the mEP17 gene were determined by primer extension using epididymal total RNA as a template and the EP17PE2 primer (SEQ ID NO:7) designed according to sequence in the first exon (FIG. 10). Primer extension methods are described in Example 4 below. Two major transcription initiation sites were localized 22 and 18 nucleotides from the putative translation initiation site, and were numbered +1 and +5, respectively. Two minor transcription initiation sites were also detected at position +2 and +4. As shown in FIG. 10, total RNA extracted from the epididymis (Ep) or transfer (t) RNA was reverse transcribed with [$^{32}$P]-radiolabeled EP17PE2 primer (SEQ ID NO:7) and extended using Avian Myeloblastosis Virus (AMV) reverse transcriptase. Lanes labeled "C", "T", "A" and "G" are [$^{35}$S]-radiolabeled DNA sequencing reactions carried out using the EP17PE2 primer (SEQ ID NO:7) and the pHindIII clone (shown in FIG. 9) as template. The localization of two major (arrows) and two minor (arrowheads) transcription initiation sites are indicated.

The 5' flanking sequence closest to the transcription start site was analyzed further. A 2.5-kb EcoRI restriction fragment comprising this sequence was isolated from the genomic BAC clone 10983 (shown in FIG. 9). A computer analysis to identify putative cis-regulatory sites was carried out using TFSEARCH version 1.3 (Yutaka Akiyama: "TFSEARCH: Searching Transcription Factor Binding Sites", http://www.rwcp.or.jp/papia/). This analysis revealed the presence of several binding sites for known transcription factors, including binding sites for androgen receptor (ARSB), retinoic acid receptor (RARE), Stimulating Protein 1 (SP-1), Activator Protein 1 (AP-1), Activator Protein 4 (AP-4), SRY (Sex-determining Region Y protein), C-Ets (cellular ets oncogene), C/EBP (CCAAT/enhancer binding protein), and Sox-5 (SRY-related sequence #5 protein). Putative cis-regulatory sites are underlined in FIG. 11. A consensus TATA box and CAAT-box are indicated. Major transcription initiation sites are marked by long arrows, and minor transcription initiation sites are marked by arrowheads. The computer analysis was carried out using TFSEARCH version 1.3 [Yukata Akiyama: "TFSEARCH: Searching Transcription Factor Binding Sites", http://www.rwcp.or.jp/papia/].

Figure 12:
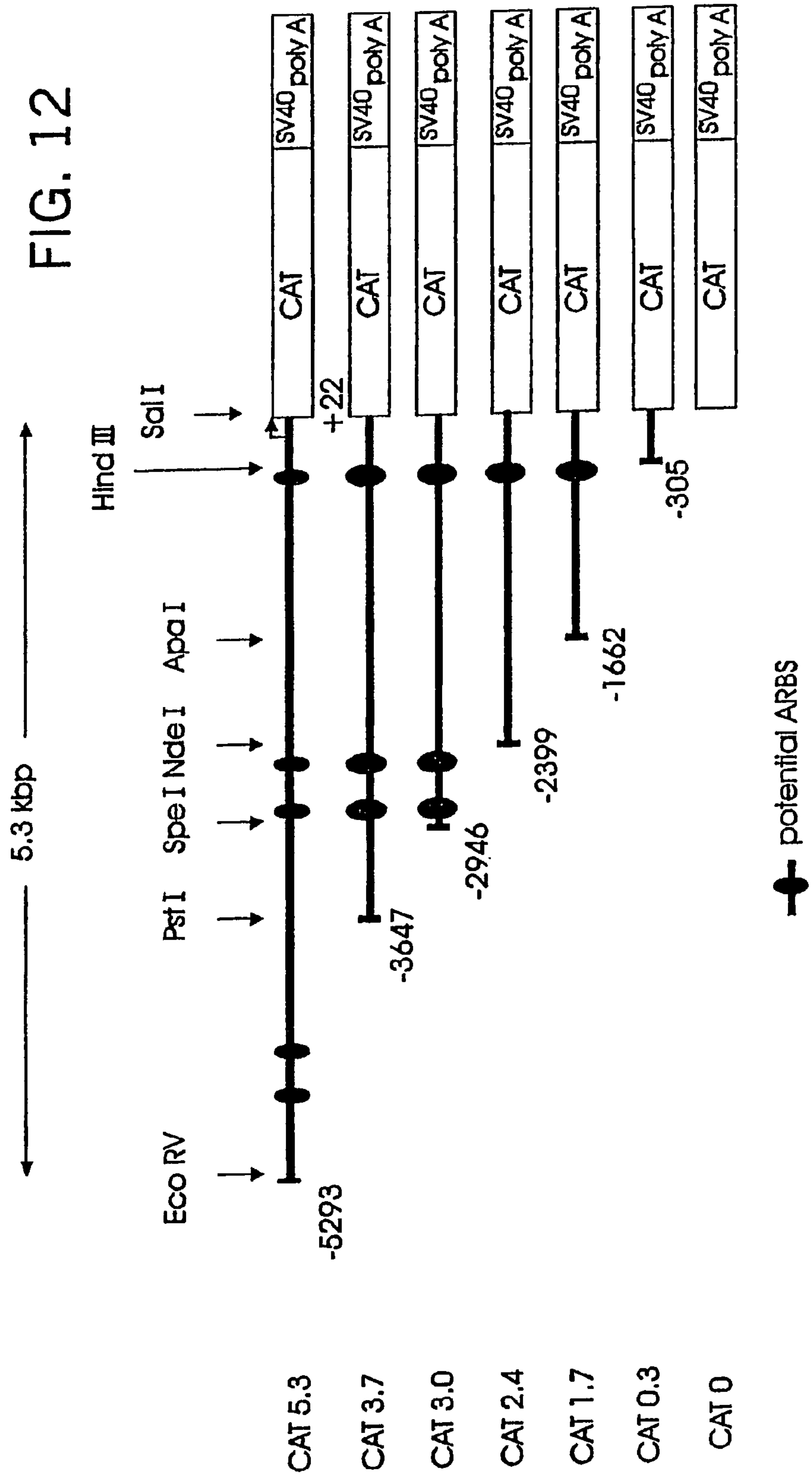
FIG. 12 depicts constructs used in functional assays of the mEP17 promoter, each construct comprising a different fragment of the 5.3 kb mEP17 promoter region (solid lines), an open reading frame encoding an exemplary reporter gene (chloramphenicol acetyltransferase, solid bar labeled "CAT") operably linked to a promoter fragment, and the polyA tail region of Simian virus 40 large T antigen.

To define functional sequences within the promoter region, several chimeric reporter genes were constructed by ligation of various portions of the 5' flanking region of the EP17 gene and a reporter gene (FIG. 12), as described in Example 5 below. Each chimeric gene comprises a different fragment of the 5.3 kb EP17 promoter region, an open reading frame encoding a reporter gene operably linked to a promoter fragment, and the polyA tail region of Simian Virus 40 large T antigen. FIG. 12 indicates one preferred reporter, chloramphenicol acetyltransferase (CAT). These constructs are alternatively used for in vitro and in vivo assays of EP17 promoter region function.

A preferable in vitro technique for evaluating EP17 promoter function is a transient transfection assay. According to this method, each chimeric reporter gene is introduced into a relevant host cell, and the resulting level of reporter gene expression is quantitated. Preferred host cells include HeLa and PC-3 cells, or normal or immortalized epididymal cells, described herein below. In these experiments, luciferase is a preferable reporter gene in that it demonstrates increased sensitivity of detection. Transient transfection assays are performed as described in Example 6. Additional methods for making an expression system comprising a promoter region operably linked to a heterologous reporter sequence are disclosed in U.S. Pat. No. 6,087,111.

To analyze the function of an EP17 promoter region in vivo, transgenic mice bearing each chimeric gene are generated as described in Example 7 below, and a level of reporter gene expression in each mouse is determined. For these experiments, CAT is a preferred reporter gene as it displays low endogenous activity in the epididymis. Several assays are performed to characterize CAT expression in transgenic animals, including PCR using CAT-specific primers, CAT enzymatic assays, immunohistochemistry using an anti-CAT antibody, and in situ hybridization using a CAT-specific probe. Methods for performing these assays can be found in Lareyre, J. J., et al. (1999) *J. Biol. Chem.* 274:8282-8290, in Lareyre et al. (2001) and Examples 2, 8, and 9.

A transgenic mouse bearing the entire 5.3 kb 5' flanking region of the EP17 gene operably linked to the CAT gene shows CAT expression in the caput epididymis, demonstrating that the 5.3 kb promoter region of the EP17 gene contains sequences required for the region-specific expression of the EP17 gene. Shorter sequences of the EP17 promoter region can be used to define a minimal sequence requisite for EP17 gene expression. In determining a promoter region that reproduces endogenous EP17 expression, the expression profile of each chimeric gene can be carefully compared to the profile of EP17 gene expression as determined by in situ hybridization.

Within a candidate promoter region or response element, the presence of regulatory proteins bound to a nucleic acid sequence can be detected using a variety of methods well known to those skilled in the art (Ausubel et al., 1992). Briefly, in vivo footprinting assays demonstrate protection of DNA sequences from chemical and enzymatic modification within living or permeabilized cells. Similarly, in vitro footprinting assays show protection of DNA sequences from chemical or enzymatic modification using protein extracts. Nitrocellulose filter-binding assays and gel electrophoresis mobility shift assays (EMSAs) track the presence of radiolabeled regulatory DNA elements based on provision of candidate transcription factors.

Figure 14:
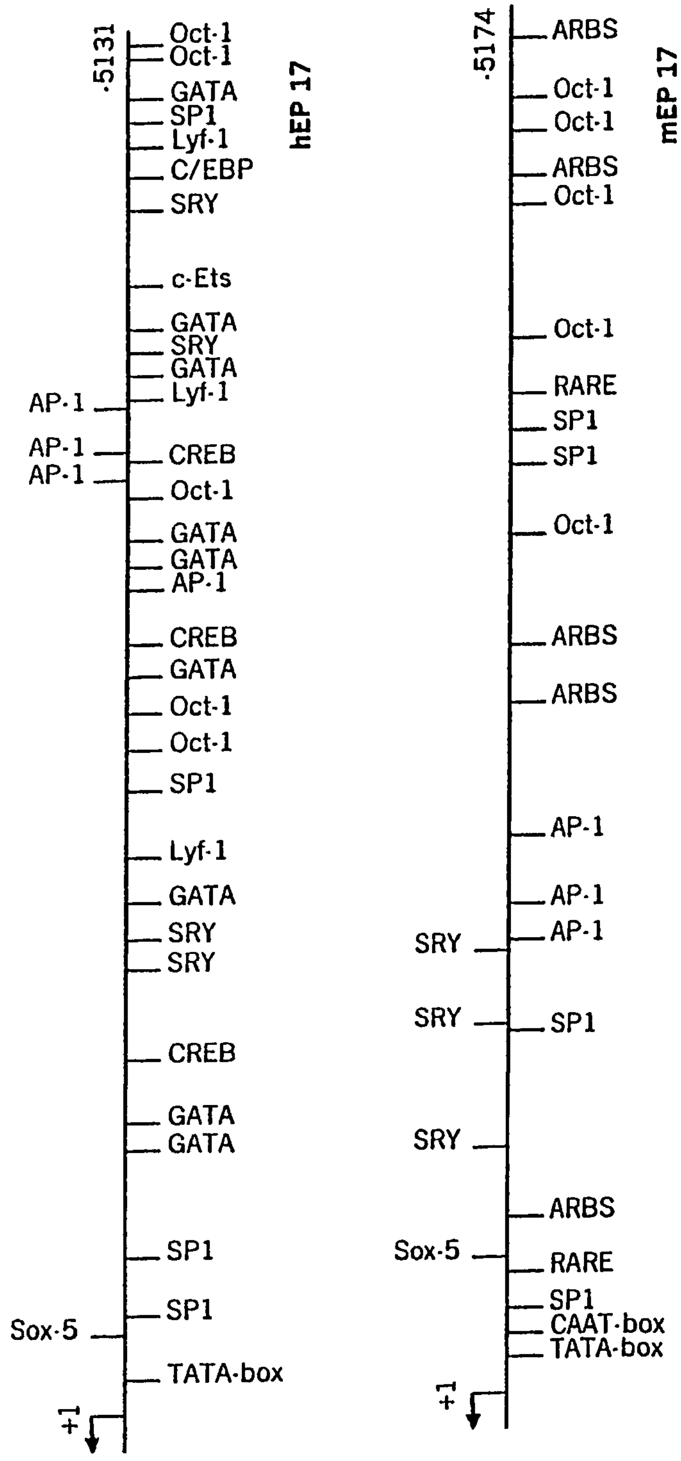
FIG. 14 presents a comparison of the putative cis-DNA regulatory elements in the mouse and human EP17 promoter regions.

Genomic clones derived from GenBank and proprietary databases (Celera Genomics Corp., Rockville, Md.) were used to predict an hEP17 promoter region comprising an about 5150 base pair region immediately upstream of the hEP17 transcription start site (FIG. 13). This region is similar to the promoter region of mEP17, having putative cis-DNA regulatory elements included but not limited to a Sp-1 binding site, an AP-1 binding site, a cAMP response element binding protein (CREB) binding site, a SRY-related HMG-box gene 5 (Sox 5) binding site, a Sex-determining region Y gene product (SRY) binding site, a c-Ets binding site, a GATA binding site, and an Octamer transcription factor 1 (Oct-1) binding site (FIG. 14). The hEP17 promoter is further characterized in a manner as described herein above regarding the mouse EP17 promoter region.

V. METHODS FOR IDENTIFYING REGULATORS OF GENE EXPRESSION

Figure 15C:
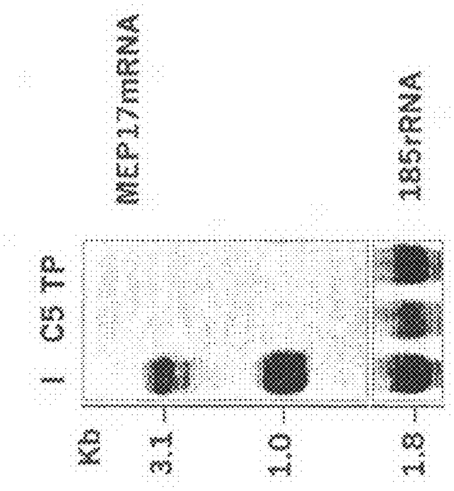
FIGS. 15A, 15B, and 15C present experiments demonstrating hormonal regulation of mEP17 transcription.
Figure 15B:
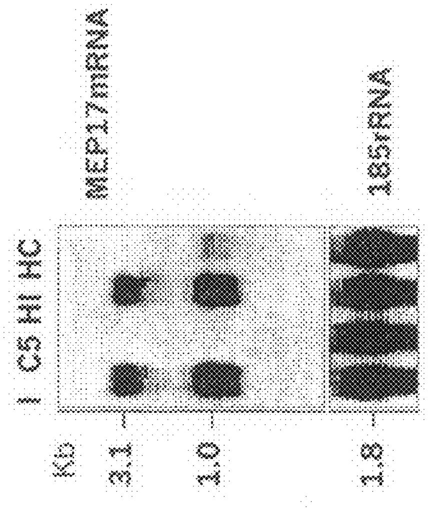
Figure 15A:
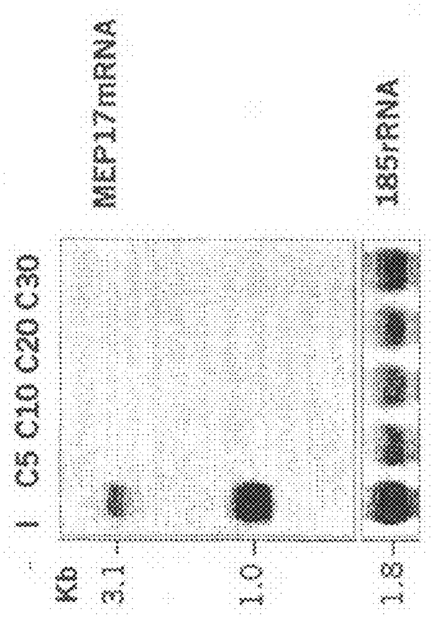

The nucleic acid sequences of the present invention can be used to identify regulators of EP17 gene expression. Several molecular cloning strategies can be used to identify substances that specifically bind EP17 cis-regulatory elements. A preferred promoter region to be used in such assays is an EP17 promoter region from mouse or human, more preferably the promoter region includes some or all amino acids of SEQ ID NOs:1 or 5. FIGS. 15A-15C presents data mEP17 expression is not regulated by hormones. However, studies in which spermatogenesis was disrupted suggest that an EP17 lipocalin can be regulated by germ cell-associated factors.

In one embodiment, a cDNA library in an expression vector, such as the lambda-gt11 vector, can be screened for cDNA clones that encode an EP17 regulatory element DNA-binding activity by probing the library with a labeled EP17 DNA fragment, or synthetic oligonucleotide (Singh et al. (1989) *Biotechniques* 7:252-261). Preferably the nucleotide sequence selected as a probe has already been demonstrated as a protein binding site using a protein-DNA binding assay described above.

In another embodiment, transcriptional regulatory proteins are identified using the yeast one-hybrid system (Luo et al. (1996) *Biotechniques* 20(4):564-568; Vidal et al. (1996) *Proc Natl Acad Sci USA* 93(19):10315-10320; Li and Herskowitz (1993) *Science* 262:1870-1874). In this case, a cis-regulatory element of an EP17 gene is operably fused as an upstream activating sequence (UAS) to one, or typically more, yeast reporter genes such as the lacZ gene, the URA3 gene, the LEU2 gene, the HIS3 gene, or the LYS2 gene, and the reporter gene fusion construct(s) is inserted into an appropriate yeast host strain. It is expected that the reporter genes are not transcriptionally active in the engineered yeast host strain, for lack of a transcriptional activator protein to bind the UAS derived from the EP17 promoter region. The engineered yeast host strain is transformed with a library of cDNAs inserted in a yeast activation domain fusion protein expression vector, e.g. pGAD, where the coding regions of the cDNA inserts are fused to a functional yeast activation domain coding segment, such as those derived from the GAL4 or VP16 activators. Transformed yeast cells that acquire a cDNA encoding a protein that binds a cis-regulatory element of an EP17 gene can be identified based on the concerted activation of the reporter genes, either by genetic selection for prototrophy (e.g. LEU2, HIS3, or LYS2 reporters) or by screening with chromogenic substrates (lacZ reporter) by methods known in the art.

In another embodiment, an in situ filter detection method is used to clone a cDNA encoding the sequence-specific DNA-binding protein as described in Example 10.

In a more preferred embodiment, one-hybrid analysis and in situ filter detection methods are used sequentially. For example, an initial collection of candidate transcription factors is identified by one-hybrid analysis, and this initial collection is secondarily screened using in situ filter detection. This combination of techniques provides a smaller but more confident pool of candidate regulators than selected by either technique alone.

A candidate regulator to be tested by these methods can be a purified molecule, a homogenous sample, or a mixture of molecules or compounds. More than one modulatable transcriptional regulatory sequence can be screened simultaneously.

In accordance with the present invention there is also provided a rapid and high throughput screening method that relies on the methods described above. This screening method comprises separately contacting each compound with a plurality of substantially identical samples. In such a screening method the plurality of samples preferably comprises more than about $10^4$ samples, or more preferably comprises more than about $5\times10^4$ samples. In an alternative high-throughput strategy, each sample can be contacted with a plurality of candidate compounds.

The present invention also provides an in vivo assay for discovery of modulators of EP17 expression. In this case, a transgenic mouse is made such that a transgene comprising an EP17 promoter and a reporter gene is expressed and a level of reporter gene expression is assayable. Such transgenic animals can be used for the identification of drugs, pharmaceuticals, therapies, and interventions that are effective in modulating EP17 expression.

VI. METHOD FOR HETEROLOGOUS GENE EXPRESSION IN EPIDIDYMIS

The present invention enables epididymal expression of a heterologous nucleic acid sequence. In this case, a transgenic animal is generated which bears a transgene that includes an EP17 promoter region and a nucleotide sequence of interest. A preferred EP17 promoter is the nucleotide sequence of SEQ ID NO:1 or 5, more preferably a minimal functional portion of SEQ ID NO:1 or 5 that drives appropriate epididymal expression, as determined by methods described herein above.

In one embodiment, this method enables assay of the function of a gene of interest in epididymis to the exclusion of other sites of gene function. For example, the heterologous sequence can encode an antisense or ribozyme nucleic acid molecule. When expressed in epididymis under the direction of an EP17 promoter region, the function of a gene corresponding to the antisense or ribozyme nucleic acid molecule is disrupted in epididymis but not other tissues.

In another embodiment, an EP17 promoter drives expression of a toxin, for example, thymidine kinase plus ganciclovir. Expression of the chimeric gene targets degeneration of the initial segment of the epididymis. In this case, the transgenic animal can be used as animal model of infertility, described further herein below.

In another embodiment, an EP17 promoter region drives expression of a therapeutic gene or nucleotide sequence, as described herein below.

VII. METHOD FOR PRODUCING AN EPIDIDYMAL CELL LINE

Another aspect of the invention is a method for producing an epididymal cell line. According to this method, a chimeric gene is constructed to express a gene encoding a selectable marker under the control of an EP17 promoter region, and the chimeric gene is used to create a transgenic animal expressing the selectable marker in epithelial cells of the initial segment of the epididymis. Preferably, the selectable marker confers antibiotic resistance, and more preferably, the selectable marker confers neomycin resistance, which can be used even in selection of epididymal cells from non-epididymal cells in culture. Also preferably, the EP17 promoter region used to perform this method is the sequence of SEQ ID NO:1, or functional portion thereof. Similarly, using the mE-RABP promoter, a neomycin-resistant immortalized cell line from the distal caput can be generated by this method.

Also provided is a method for generating an immortalized epididymal cell line. In this case, a transgenic animal is obtained, having a transgene that encodes an oncogenic virus directed by a constitutive promoter. A preferred oncogenic virus comprises a temperature-sensitive (ts) Simian virus 40 large T antigen (Tegtmeyer (1975) *J Virol* 15(3):613-618). The ts-Simian virus 40 large T-antigen is completely inactive at non-permissive temperature (39° C.), partially inactive at body temperature, and substantially active at a permissive temperature (33° C.). Immortalized epithelial cells are procured from ts-Simian virus 40 large T-antigen mouse are reproduced in culture. In one embodiment, epididymal cells may be selected using the EP17 promoter operably linked to the neomycin resistant gene. Since the EP17 promoter is expressed in the initial segment, neo-selection will provide a pure population of epithelial cells from that segment. A neomycin-resistant immortalized cell line from the distal caput has been generated by this method using the E-RABP promoter and maintained in culture for 12 months.

VIII. METHOD FOR HOMOLOGOUS RECOMBINATION AT THE EP17 LOCUS

Another aspect of the invention is a method for mutagenizing the EP17 locus by homologous recombination. The method uses a targeting vector having an isolated EP17 promoter region, a marker gene, and an isolated EP17 3' flanking region. In a vector so constructed, the marker gene is positioned between the promoter region and the 3' flanking region. In another embodiment, the targeting vector further comprises a mutant EP17 coding sequence, also positioned between the promoter region and the 3' flanking region. The targeting vector is linearized by digestion with a restriction endonuclease at a site other than within the promoter region, marker gene, 3' flanking region, and optional mutant EP17 coding sequence.

In a preferred embodiment, the linearized vector is electroporated into embryonic stem cells, and successful electroporation is assayed by detecting the marker gene in the stem cells. Stem cells bearing the vector are used to create a transgenic animal. According to the method, a homologous recombination event is mediated at the EP17 locus, thereby exchanging native EP17 gene sequences positioned between the promoter region and the 3' flanking region with vector nucleotide sequences positioned the same.

The nucleic acids and methods of the present invention enable knock-out, knock-in, and knock-down mutations of the EP17 gene. The phenotype of EP17 mutant animals can be characterized to reveal EP17 function. The expression of EP17 in epididymis, and the known functional importance of regulated epididymal gene expression for male fertility, suggest that EP17 will have a determinative role in sperm maturation. Methods for generating MEP17 mutant mice are provided in Example 11.

Figures 16, 16A:
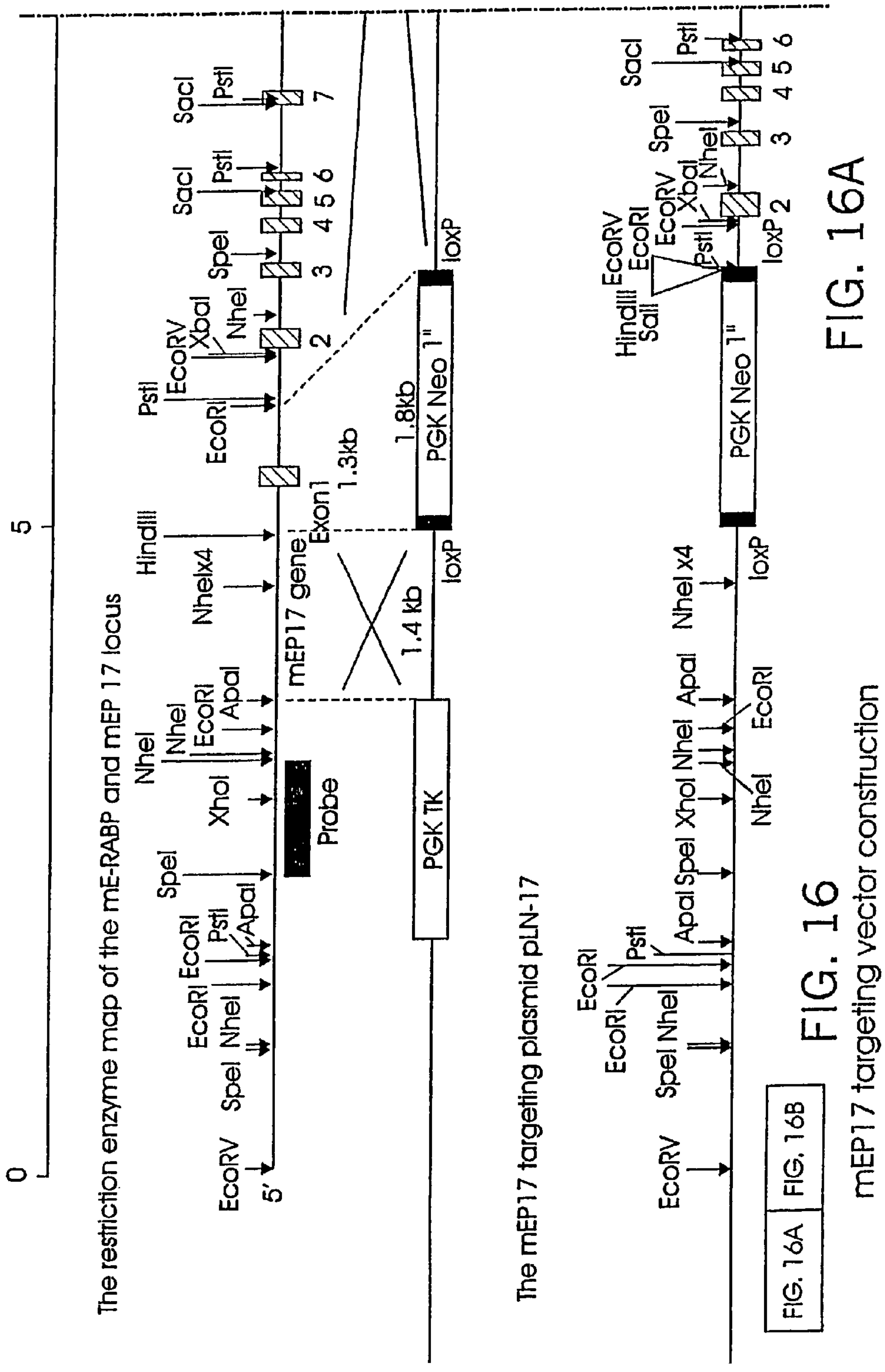
FIG. 16 depicts homologous recombination at the mEP17 locus using the pLN-17 vector. The mEP17/mE-RABP genomic region is presented at the top. mEP17 exons are indicated by hatched rectangles. mE-RABP exons are indicated by open rectangles. The mEP17 targeting plasmid pLN-17 is designed so that 1.4 kb of mEP17 5' flanking region is positioned immediately upstream of the vector PGK neomycin sequence, and 10.9 kb of mEP17 3' flanking region and mE-RABP gene is positioned immediately downstream of the vector PGK neomycin sequence. mEP17 sequences carried in the pLN-17 targeting vector mediate homologous recombination, depicted as an "X" between the genomic region and the targeting plasmid. The recombination event creates a genomic reorganization wherein the entire mEP17 coding sequence is replaced by the PGK neomycin sequence.
Figure 16B:
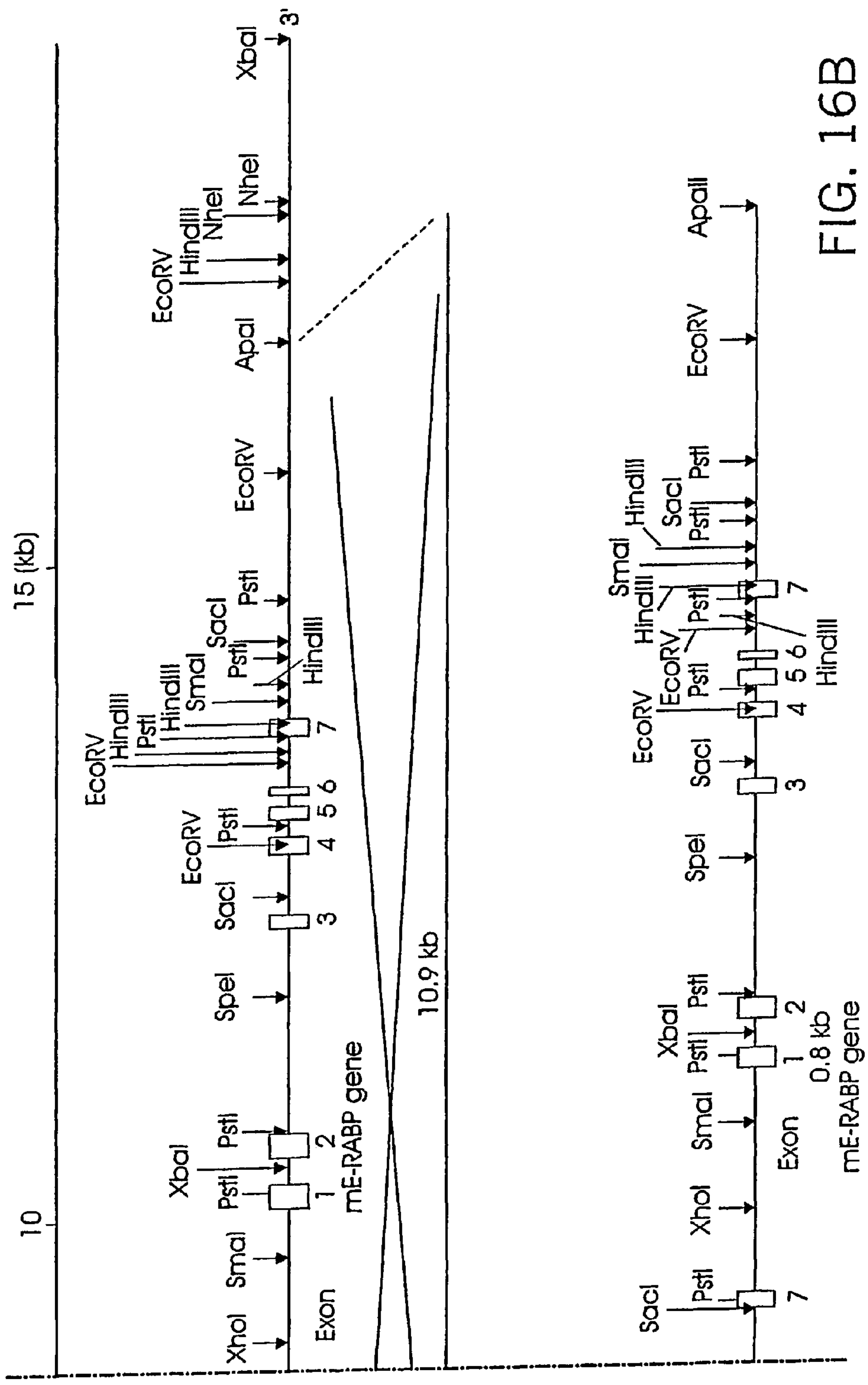

A preferred knock-out mutation removes part of the EP17 coding region (exon1) and can be generated using a targeting vector as depicted in FIG. 16. Preferred knock-in mutations include mutation of any one of amino acids within the conserved lipocalin motifs to any amino acid that is non-conservative substitution. Other preferred knock-in mutations are targeted replacement of one or both of the conserved cysteine residues with an amino acid(s) that is a non-conservative substitution.

IX. METHOD FOR DETECTING A EP17 NUCLEIC ACID MOLECULE

In another aspect of the invention, a method is provided for detecting a nucleic acid molecule that encodes an EP17 polypeptide. According to the method, a biological sample having nucleic acid material is procured and hybridized under stringent hybridization conditions to an EP17 nucleic acid molecule of the present invention. Such hybridization enables a nucleic acid molecule of the biological sample and the EP17 nucleic acid molecule to form a detectable duplex structure. Preferably, the EP17 nucleic acid molecule includes some or all nucleotides of SEQ ID NO:1, 2, 3, or 5. also preferably, the biological sample comprises human nucleic acid material.

In another embodiment, genetic assays based on nucleic acid molecules of the present invention can be used to screen for genetic variants by a number of PCR-based techniques, including single-strand conformation polymorphism (SSCP) analysis (Orita, M., et al. (1989) *Proc Natl Acad Sci USA* 86(8):2766-2770), SSCP/heteroduplex analysis, enzyme mismatch cleavage, and direct sequence analysis of amplified exons (Kestila et al. (1998) *Mol Cell* 1 (4):575-582; Yuan et al. (1999) *Hum Mutat* 14(5):440-446). Automated methods can also be applied to large-scale characterization of single nucleotide polymorphisms (Brookes (1999) *Gene* 234(2):177-186; Wang et al. (1998) *Science* 280(5366):1077-82). The present invention further provides assays to detect a mutation of a variant EP17 locus by methods such as allele-specific hybridization (Stoneking et al. (1991) *Am J Hum Genet.* 48(2):370-82), or restriction analysis of amplified genomic DNA containing the specific mutation.

X. RECOMBINANT PRODUCTION OF AN EP17 POLYPEPTIDE

The present invention also provides a method for recombinant production of a EP17 polypeptide, as described in Example 12. Preferably, the recombinant polypeptide comprises some or all of the amino acid sequences of SEQ ID NO:4 or 6.

Figure 17:
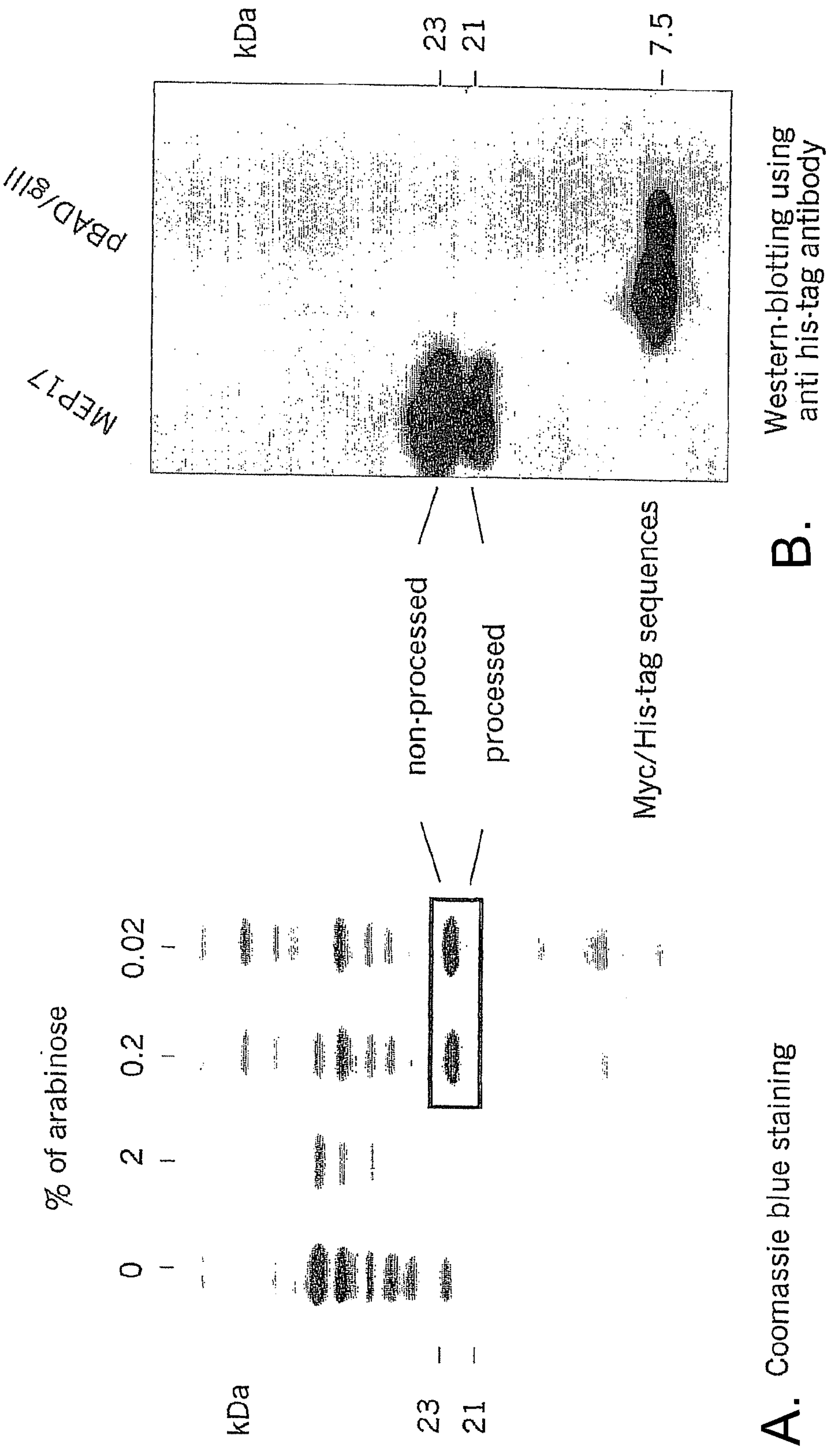
FIG. 17 shows recombinant production of mEP17 protein using the pBAD/gIII vector (Invitrogen). Protein extracted from *E. coli* transformed with pBAD/gIII-mEP17 is resolved by polyacrylamide gel electrophoresis.

Mouse EP17 protein was recombinantly produced using the pBAD/gIII vector (Invitrogen of Carlsbad, Calif.). To confirm the production of EP17 protein, total protein derived from transformed *E. coli* was resolved on a polyacrylamide gel, and Coomassie blue staining revealed two enriched bands of approximately 21 kDa and 23 kDa. Western blot analysis using an anti-his tag antibody revealed the same two proteins, which correspond to the processed and unprocessed EP17 isoforms, respectively (FIG. 17)

Recombinantly produced proteins are useful for a variety of purposes, including structural determination of an EP17 polypeptide, generation of an antibody that recognizes an EP17 polypeptide, and screening assays to identify a chemical compound or peptide that interacts with an EP17 polypeptide, described further herein below.

XI. PRODUCTION OF EP17 ANTIBODIES

In another aspect, the present invention provides a method of producing an antibody immunoreactive with a lipocalin polypeptide, the method comprising recombinantly or synthetically producing an EP17 polypeptide, or portion thereof, to be used as an antigen. The EP17 polypeptide is formulated so that it is used as an effective immunogen. An animal is immunized with the formulated EP17 polypeptide, generating an immune response in the animal. The immune response is characterized by the production of antibodies that can be collected from the blood serum of the animal. Preferred embodiments of the method use a polypeptide as of SEQ ID NO:4 or 6.

The present invention also encompasses antibodies produced by this method.

The foregoing antibodies can be used in methods known in the art relating to the localization and activity of the EP17 polypeptide sequences of the invention, e.g., for cloning of EP17 nucleic acids, immunopurification of EP17 polypeptides, imaging EP17 polypeptides in a biological sample, measuring levels thereof in appropriate biological samples, and in diagnostic methods.

XII. METHOD FOR DETECTING AN EP17 POLYPEPTIDE

In another aspect of the invention, a method is provided for detecting a level of EP17 polypeptide using an antibody that specifically recognizes an EP17 polypeptide, or portion thereof. In a preferred embodiment, biological samples from an experimental subject and a control subject are obtained, and EP17 polypeptide is detected in each sample by immunochemical reaction with the EP17 antibody. More preferably, the antibody recognizes amino acids of SEQ ID NO:4 or 6 and is prepared according to a method of the present invention for producing such an antibody.

In one embodiment, an EP17 antibody is used to screen a biological sample for the presence of a lipocalin polypeptide. A biological sample to be screened can be a biological fluid such as extracellular or intracellular fluid, or a cell or tissue extract or homogenate. A biological sample can also be an isolated cell (e.g., in culture) or a collection of cells such as in a tissue sample or histology sample. A tissue sample can be suspended in a liquid medium or fixed onto a solid support such as a microscope slide. In accordance with a screening assay method, a biological sample is exposed to an antibody immunoreactive with an EP17 polypeptide whose presence is being assayed, and the formation of antibody-polypeptide complexes is detected. Techniques for detecting such antibody-antigen conjugates or complexes are well known in the art and include but are not limited to centrifugation, affinity chromatography and the like, and binding of a labeled secondary antibody to the antibody-candidate receptor complex.

XIII. SCREENING FOR SMALL MOLECULE LIGANDS THAT INTERACT WITH EP17

The present invention further discloses a method for identifying a compound that modulates EP17 function. According to the method, an EP17 polypeptide is exposed to a plurality of compounds, and binding of a compound to the isolated EP17 polypeptide is assayed. A compound is selected that demonstrates specific binding to the isolated EP17 polypeptide. Preferably, the EP17 polypeptide used in the binding assay of the method includes some or all amino acids of SEQ ID NO:4 or 6.

Several techniques can be used to detect interactions between a protein and a chemical ligand without employing an in vivo ligand. Representative methods include, but are not limited to, fluorescence correlation spectroscopy, surface-enhanced laser desorption/ionization, and biacore technology, as described in Example 13. These methods are amenable to automated, high-throughput screening.

Candidate regulators include but are not limited to proteins, peptides, and chemical compounds. Structural analysis of these selectants can provide information about ligand-target molecule interactions that enable the development of pharmaceuticals based on these lead structures.

Similarly, the knowledge of the structure a native EP17 polypeptide provides an approach for rational drug design. The structure of an EP17 polypeptide can be determined by X-ray crystallography or by computational algorithms that generate three-dimensional representations. See Huang et al. (2000) *Pac Symp Biocomput* 230-41; Saqi et al. (1999) *Bioinformatics* 15:521-522. Computer models can further predict binding of a protein structure to various substrate molecules, that can be synthesized and tested. Additional drug design techniques are described in U.S. Pat. Nos. 5,834,228 and 5,872,011.

XIV. ANIMAL MODEL OF MALE INFERTILITY

The present invention further pertains to an animal model of male infertility. Such a model is prepared by several methods.

Using a transgenic approach, knock-out, knock-in, or knock-down mutation of the EP17 gene can suppress fertility. In another embodiment, expression of a toxin, for example, thymidine kinase plus ganciclovir, under the direction of an EP17 promotertargets degeneration of the initial segment of the epididymis and thereby compromises fertility.

The present invention also teaches that an animal model of fertility is prepared by immunizing an animal with an EP17 polypeptide. The resulting immune response in the animal comprises a production of antibodies that specifically bind an EP17 polypeptide, thereby disrupting its biological activity.

A method is also provided for generating an animal model of infertility by administering to an animal a compound that disrupts EP17 expression or function. Such a compound is discovered by methods disclosed herein.

Animal models of male infertility can be characterized according to several measures, including in vivo and in vitro assays of fertility, as described in Examples 14 and 15 below, and morphological inspection of the epididymis.

XV. THERAPEUTIC APPLICATIONS

Another aspect of the present invention is a therapeutic method comprising administering to a subject a substance that modulates lipocalin biological activity. Therapeutic substances include but are not limited to chemical compounds, antibodies, and gene therapy vectors.

Compounds that are discovered by the methods disclosed herein is useful for therapeutic applications related to male fertility. For example, a compound that mimics EP17 function, when administered to an infertile male subject, can regulate fertility by promoting spermatozoa maturation in the epididymis. Conversely, a compound that interferes with EP17 function can act to suppress spermatozoa maturation when administered to a fertile subject.

The present invention also provides a method for disrupting EP17 function by immunizing a subject with an effective dose of the disclosed EP17 polypeptide. The immune system of the subject produces an antibody that specifically recognizes the EP17 polypeptide, and binding of the antibody to the EP17 polypeptide abolishes EP17 function. In a preferred embodiment, the antibody recognizes some or all of the amino acids of SEQ ID NO:4 or 6 and is prepared according to a method of the present invention for producing such an antibody.

Several studies have demonstrated the utility of immunotherapeutic approaches to contraception and teach methods for preparing and administering such vaccines, including U.S. Pat. Nos. 6,132,720 and 6,096,318, Feng et al. (1999), and Naz (1999). U.S. Pat. No. 6,096,318 additionally discloses methods for chemical modification of immunogenic proteins, and fragments thereof, which elicit an amplified immune response in a subject receiving an injection of the modified polypeptide. Briefly, the antigen modification is accomplished by attaching the protein to a carrier such as a bacterial toxin or by polymerization of protein fragments. This method has been used to modify human chorionic gonadotropin, an antigen that is effective for immunological contraception in mammals.

The present invention further provides lipocalin nucleic acid sequences and gene therapy methods for modulating lipocalin activity in a target cell. The gene therapy vector can encode an EP17 lipocalin, preferably comprising the amino acid sequences of SEQ ID NO:4 or 6. Alternatively, a gene therapy vector can include sequences encoding a nucleic acid molecule, peptide, or protein that interacts with an EP17 lipocalin. This modulation can affect spermatozoa maturation in the vicinity of a lipocalin-secreting cell. Additionally, a gene therapy vector can include an EP17 promoter sequence of the present invention to provide tissue specific expression of a gene of interest in a subject. Preferably, the EP17 promoter regions used to perform this method is the nucleotide sequence of SEQ ID NO:1 or 5, or functional portion thereof.

Vehicles for delivery of a gene therapy vector include but are not limited to a liposome, a cell, and a virus. Preferably, a cell is transformed or transfected with the DNA molecule or is derived from such a transformed or transfected cell. An exemplary and preferred transformed or transfected cell is a epididymal cell. Alternatively, the vehicle is a virus, including a retroviral vector, adenoviral vector or vaccinia virus whose genome has been manipulated in alternative ways so as to render the virus non-pathogenic. Methods for creating such a viral mutation are detailed in U.S. Pat. No. 4,769,331. Exemplary gene therapy methods are described in U.S. Pat. Nos. 5,279,833; 5,286,634; 5,399,346; 5,646,008; 5,651,964; 5,641,484; and 5,643,567.

The ability for adenovirus gene therapy vectors to infect male germ cells to the exclusion of embryos fertilized by infected sperm was demonstrated by Hall et al. (2000) *Hum Gene Ther* 11(12):1705-1712. High titers of the vector were injected directly into mouse testis and epididymis, or alternatively, sperm were exposed to the virus immediately prior to or during in vitro fertilization. The vector carried the bacterial lacZ gene under the direction of the Rous sarcoma virus promoter, and infection was assayed by enzymatic or immunologic detection of β-galactosidase. lacZ expression was assayed during the several weeks following injection, and in preimplantation embryos produced by in vitro fertilization with sperm exposed to gene therapy vector. lacZ expression was observed in sperm but not in embryos, supporting a conclusion that adenovirus vectors pose minimal risk for germ line integration when exposed to male reproductive cells. These studies teach methods for construction of a gene therapy vector and effective administration of a vector in the male reproductive system, as proposed for administration of nucleic acids of the present invention.

The invention further provides a method for diminishing the fertile capacity of a subject. According to the method, a chemical compound, peptide, or antibody that interacts with an EP17 polypeptide, preferably the polypeptide of SEQ ID NO:4 or 6, is identified. A pharmaceutical preparation is prepared comprising such a chemical compound, peptide, or antibody, and a carrier. An effective dose of the pharmaceutical composition is administered to a subject, whereby the fertile capacity of the subject is diminished.

The invention further provides a method for promoting the fertile capacity of a subject. In this case, a chemical compound or peptide that interacts with an EP17 polypeptide, preferably the polypeptide of SEQ ID NO:4 or 6, is identified. A pharmaceutical composition comprising the chemical compound or peptide and a carrier is prepared. An effective dose of the pharmaceutical composition is administered to a subject, whereby the fertile capacity of the subject is improved.

XVI. SUMMARY

Summarily, the provisions of an EP17 promoter region, a 3' flanking genomic region of mEP17, a coding sequence of hEP17, and a hEP17 polypeptide are a significant advance in fertility-related research. The disclosed EP17 nucleic acids and polypeptides can be used according to methods of the present invention to generate a mouse model of male infertility, for drug discovery screens, and for therapeutic treatment of fertility-related conditions.

EXAMPLES

The following Examples have been included to illustrate modes of the invention. Certain aspects of the following Examples are described in terms of techniques and procedures found or contemplated by the present co-inventors to work well in the practice of the invention. These Examples illustrate standard laboratory practices of the co-inventors. In light of the present disclosure and the general level of skill in the art, those of skill will appreciate that the following Examples are intended to be exemplary only and that numerous changes, modification and alteration can be employed without departing from the scope of the invention.

Example 1

Cloning of Mouse EP17 Promoter Region

Two clones containing 6.3 kb EcoRV restriction fragments were isolated from the genomic BAC clone 10983 (FIG. 9). The DNA fragments were subcloned in pBluescript SK+ (Promega, Madison, Wis.) using appropriate enzymes. DNA templates for sequencing were purified using the "Plasmid Midi kit" (Qiagen Inc., Santa Clarita, Calif.). Sequencing reactions were performed as described in the Thermo Sequenase™ fluorescent labeled primer cycle sequencing kit (Perkin-Elmer, Foster City, Calif.). DNA fragments were separated in a denaturing PAGE (6% acrylamide gel) and analyzed using an ABI 373A automated sequencer (PE, Applied Biosystems, Foster City, Calif.). Nucleotide sequences were analyzed using the GeneJockey™ software available from Biosoft of Ferguson, Mo. DNA sequencing analysis of both clones revealed that the 6.3 kb fragment contains 5.4 kb 5' flanking region of the mEP17 gene.

Example 2

In Situ Hybridization

Nonisotopic in situ hybridization was performed on 4-6 μm thick cryosections of fresh-frozen mouse epididymis. Sections were fixed in 4% formaldehyde in 0.1 M sodium phosphate buffer pH 7.2 and then incubated for 10 minutes in PBS containing 5 μg/ml proteinase K. See Sambrook et al. (1992) for a description of PBS. After two rinses in PBS, sections were incubated in 0.25% acetic anhydride in 0.1 M triethanolamine pH 8.0 for 15 minutes. Sense and antisense riboprobes were prepared in 20 μl transcription reactions containing SP6 (Promega, Madison, Wis.) or T7 (New England Biolabs, Beverly, Mass.) polymerase, 1× transcription buffer, 1 mM each of ATP, CTP, and GTP, 0.65 mM UTP, 0.35 mM digoxygenin-UTP (Roche Diagnostics Corp, Indianapolis, Ind.), and 1 μg linearized F3 plasmid carrying the mEP17 cDNA. Unincorporated nucleotides were removed on a Chroma Spin-100 STE column (Clontech, Palo Alto, Calif.).

Labeled riboprobes were denatured for 5 minutes at 80° C., diluted in hybridization buffer composed of 50% (vol/vol) formamide, 10% (wt/vol) dextran sulfate, 4×SSC, 1×Denhardt's reagent, 0.5 mg/ml yeast tRNA, and incubated with the sections overnight at 55° C. See Sambrook et al., 1992 for a description of SSC buffer. The slides were washed at room temperature for 5 minutes in 2×SSC, rinsed in STE buffer (500 mM NaCl, 20 mM Tris-HCl pH 7.5, 1 mM EDTA), and then incubated for 30 minutes in STE containing 40 μg/ml RNase A. The sections were washed sequentially for 5 minutes each in 2×SSC, 50% formamide at 50° C., then at room temperature with 1×SSC, and finally with 0.5×SSC.

To detect hybridized probes, slides were rinsed in TN buffer (100 mM Tris-HCl pH 7.5, 150 mM NaCl), blocked for 1 hour in blocking solution (TN buffer containing 2% horse serum and 0.1% Triton X-100), and incubated for 1 hour in 1:500 diluted alkaline phosphatase conjugated antidigoxygenin (Roche Diagnotics Corp.) in blocking solution. Slides were rinsed three times in blocking solution and then in a substrate buffer of 100 mM This-HCl pH 9.5, 100 mM NaCl, 50 mM $MgCl_2$. Color development was in substrate buffer containing 0.17 mM 5-bromo-4-chloro-3-indolyl phosphate, 10 mM N-ethyl-maleimide, and 1 mM levamisole as an inhibitor of endogenous alkaline phosphatase. Color development was stopped with 10 mM This-HCl pH 8.0 and 1 mM EDTA. Sections were examined and photographed with a Zeiss Axiophot using both bright field and phase contrast optics.

Example 3

Cloning Human EP17

To recover a full-length human EP17 gene, a hybridization screen is performed using a human epididymal genomic library probed with the nucleotide sequence of SEQ ID NO:2, 3 or 5, or portion thereof. Positive colonies are selected, a subset sequenced, and a clone corresponding to the full-length cDNA is recovered. Alternatively, primers from the predicted 5' and 3' ends of SEQ ID NO:2 are used in polymerase chain reaction with a human epididymal genomic DNA as template to amplify a fragment representing the full-length clone.

To recover a full-length human EP17 cDNA, a hybridization screen is performed using a human epididymal cDNA library probed with the nucleotide sequence of SEQ ID NO:2 or 3, or portion thereof. Positive colonies are selected, a subset sequenced, and a clone corresponding to the full-length cDNA is recovered. Alternatively, primers from the predicted 5' and 3' ends of SEQ ID NO:3 are used in polymerase chain reaction with a human epididymal cDNA as template to amplify a fragment representing the full-length clone.

Example 4

Primer Extension Analysis to Identify Transcription Initiation Sites

Total RNA was extracted from the mouse epididymis using a method described previously (Chomczynski and Sacchi (1987) *Anal Biochem* 162:156-159). The EP17PE2 primer (SEQ ID NO:7) specific for mEP17 mRNA was radiolabeled using T4 nucleic acid sequence kinase in the presence of 100 μCi [$\gamma$-$^{32}$P]-ATP (3000 Ci/mmol) (Amersham) according to the manufacturer's instructions (New England Biolabs). For each reaction, 10 μg of epididymal total RNA or transfer RNA was hybridized to 1 pmol ($10^5$ dpm) of EP17PE2 primer for 12 hours at 35° C. in 10 μl of a solution containing 0.04 M [1,4]-piperazine diethanesulfonic acid (PIPES), pH 6.4, 1 μM EDTA, and 80% (vol/vol) formamide.

Reverse transcription was performed in 20 μl containing 50 μM Tris-HCl pH 8.3, 30 μM KCl, 8 μM $MgCl_2$, 6 μM DTT, 0.5 mM of each dNTP, and 50 units Avian Myeloblastosis Virus (AMV) reverse transcriptase (Promega, Madison, Wis.). Samples were incubated for 30 minutes at 42° C., and then, 50 units of AMV reverse transcriptase were added again and incubated for 1 hour more. Elongated radiolabeled fragments were loaded on a denaturing PAGE (7% polyacrylamide gel) next to sequencing reactions carried out using the Sequenase sequencing kit (Amersham, USB). The clone pHindIII (shown in FIG. 9) and the EP17PE2 primer (SEQ ID NO:7) were used as template and primer, respectively.

Example 5

Chimeric Gene Expression Constructs

DNA fragments derived from the BAC clone 10983 were generated using appropriate restriction enzymes. DNA fragments were resolved on an agarose gel, purified from the agarose, and ligated into the promoterless pBLCAT3 plasmid (Luckow, 1987) by standard methods. This construction enabled expression of the CAT gene by a mEP17 promoter region fragment.

Example 6

Transient Transfection Assays

Unless otherwise indicated, all media, cell culture and transfection reagents were obtained from GIBCO BRL (Life Technologies, Rockville, Md.). PC-3 and HeLa cells were cultured in F12K Nutrient Mixture (Kaighn's Modification) or Dulbecco's Modified Eagle Medium (DMEM) supplemented with 50 units/ml penicillin, 50 μg/ml streptomycin and 10% (v/v) charcoal/dextran treated fetal bovine serum (FBS, Hyclone, Logan, Utah). Both cultures were maintained at 37° C. in humidified air with 5% $CO_2$. Plasmids were prepared with the QIAGEN™ plasmid kit. Lipofectin reagent and PLUS reagent (Gibco BRL) were used according to the manufacturer's protocol. Briefly, cells were plated at $2\times10^5$ cells/well in 6-well plates the day before transfection. After 24 hours, 5 μl of PLUS reagent, 0.5 μg of chimeric construct, 0.5 μg of androgen or glucocorticoid expression vector and 0.05 μg of pRL-CMV, were diluted in 100 μl of DMEM and incubated for 15 minutes at room temperature. The two solutions were combined, gently mixed, and incubated for 15 minutes at room temperature. Four or eight μl of Lipofectin reagent was diluted in DMEM and incubated for 15 minutes at room temperature. The two solutions were combined, gently mixed, and incubated for 15 minutes at room temperature. While complexes were forming, medium was replaced with 800 μl of fresh DMEM. Following incubation, the transfection mixtures were added to the wells. Cells were incubated for 4 hours at 37° C. at 5% $CO_2$. After incubation, medium was replaced with 2 ml of DMEM containing 10% FBS and appropriate hormones. After 24 hours, cells were washed once with phosphate buffered saline, 500 μl of passive lysis buffer (Promega) were added and cells were incubated for 15 minutes at room temperature in a shaker. The cell lysates were transferred to fresh tubes, centrifuged at 12,000 rpm for 30 seconds to remove debris and stored at −80° C. For efficiency control, *Renilla* luciferase activity (pRL-CMV) was monitored.

Example 7

Transgenic Mice

The chimeric gene comprising the 5.3 kb EP17 promoter region fragment and the CAT reporter gene was excised from the pUC18 vector by restriction enzyme digest. DNA fragments were purified on a 0.8% (w/v) agarose gel using the AgarACE™ enzyme (Promega). Transgenic mice (strain B6D2; Harlan Sprague-Dawley) were generated by microinjection of the DNA into the male pronucleus of a fertilized oocyte using standard techniques (Palmiter and Brinster (1985) *Cell* 41:343-345). Seven independent transgenic lines carrying the CAT reporter gene were obtained. Caput epididymis-specific CAT activity was detected in three transgenic mouse lines. CAT expression was restricted to the initial segment of the caput epididymis as observed for the mEP17 gene. Thus, the 5.3 kb fragment of the mEP17 5' flanking region is sufficient of region-specific expression and can be used for heterologous expression in the initial segment of the caput epididymis.

Example 8

PCR Assay of Transgenic Mice

Transgenic animals were identified by PCR-based screening using DNA isolated from the tail of each animal. Approximately 1 cm of the tail was digested overnight at 55° C. in a Proteinase K digestion mix (10 mM Tris-Cl, pH 7.5, 75 mM NaCl, 25 mM EDTA, 1% SDS, 0.5 mg/ml Proteinase K). DNA was extracted with one volume of phenol/chloroform/isoamyl alcohol (25/24/1) and precipitated at room temperature with two volumes of absolute ethanol. Samples were centrifuged at 10,000×g at 4° C. for 15 minutes, washed with 70% ethanol, centrifuged at 10,000×g at 4° C. for 15 minutes, and dried for 2 hours at room temperature.

500 ng of genomic DNA were mixed with 1×PCR buffer II (Perkin Elmer), 2 units of Taq DNA polymerase (Promega), 1.5 mM $MgCl_2$, 1 μM concentration of each primer (primer 1, SEQ ID NO:8; primer 2, SEQ ID NO:9; casein forward primer, SEQ ID NO:10; casein reverse primer, SEQ ID NO:11), and 0.2 mM dNTP. DNA fragments were amplified for 30 cycles (95° C., 1 minute; 50° C. 45 seconds, 72° C., 45 seconds) and 1 cycle (95° C., 1 minute; 50° C. 45 seconds; 72° C., 10 minutes). PCR products were analyzed on a 2% (w/v) agarose gel.

Example 9

CAT Enzymatic Assay in Transgenic Mice

To monitor CAT activity, organs were dissected from a transgenic animal and homogenized by 20 strokes with a B pestle in a glass Dounce homogenizer in 200 μl of 0.1M Tris-HCl, 0.1% Triton X-100, pH 7.8. Insoluble material was removed by centrifugation (14,500×g at 4° C. for 5 minutes). CAT assays were performed by the two-phase flour diffusion method as described previously (Nachtigal et al. (1989) *Nuc Acid Res* 17:4327-4337). Briefly, cell lysate (50 to 200 μg) is added to a scintillation vial with a lysis buffer to give a total volume of 200 μl. The solution is heated to 65° C. for 10 mintues, cooled to room temperature, and a reaction mix (75 μl), containing 2 μl $^3$H-acetyl CoA (Amersham Pharmacia Biotech), 50 μl of 5 mM chloramphenicol (in water), 7.5 μl of 1M Tris-HCl (pH 7.8) and 15.5 μl of water, was added. The reaction mixture was carefully overlaid with 3 ml of organic phase scintillation cocktail. After 30 minutes, the samples were counted for at least 5 minutes. Quantitative values for CAT activity were determined by regression analysis to give counts per minute, per mg (cpm/min/mg) of protein cell lysate.

Example 10

In Situ Filter Detection

About $10^7$ λgt11 clones of a cDNA expression library are prepared from RNA containing poly$(A)^+$ RNA of the mouse distal caput epididymis. Clones are plated and replicated on nitrocellulose filters. After denaturaion and renaturation, the filter-bound proteins are screened with a concatenated oligonucleotide probe containing the nucleotide sequence of the cis-DNA regulatory element containing the nucleotide sequence of the cis-DNA regulatory element. The probe is prepared by nick translation with a specific activity of $>10^8$/μg. Duplicate screening using a probe carrying a mutated cis-DNA regulatory element is carried out to eliminate false positive clones.

Example 11

Mouse EP17 Knock-Out

To recover genomic DNA sequence necessary for homologous recombination, a 129/SvEv mouse genomic DNA library was screened using mE-RABP cDNA as a probe. BAC clone 170K23 was isolated, having 5.3 kb flanking region and all exons of the mEP17 gene. The targeting vector comprises a 5.3 kb EcoRV-SalI fragment of the 5' promoter region and a 1.9 kb 3' flanking region (FIG. 9). The entire mEP17 coding region is replaced with a PGKneomycin cassette from the pLNTK vector (Gorman et al., 1996), so that the PGKneomycin cassette is positioned between the 5' promoter region and the 3' flanking region. The targeting vector is linearized using an appropriate restriction enzyme, and the linearized vector is electroporated into TL1 embryonic stem (ES) cells. ES cells are selected based on demonstrated resistance to geneticin after 24 hours. Resistant cells are further screened by Southern blot analysis using a probe designed according to sequence of the targeting vector.

Clones bearing the transgene are injected into blastocysts according to standard procedures (Joyner (1993) "*Gene Targeting—A Practical Approach" IRL Press, Oxford). Chimeric mice bearing the transgene are crossed with* C57BL/6 females and agouti offspring are analyzed by PCR and Southern blot analysis for presence of the targeted allele. mEP17 homozygous mutant mice are obtained by crossing heterozygous mice having one native allele and a knock-out allele. mEP17 homozygous mutant mice are confirmed as such by demonstrating a loss of mEP17 expression by standard methods, including Northern blot analysis, RNAse protection assays, Western blot analysis, and immunohistochemistry.

Example 12

Recombinant Production of EP17 Protein

The mature protein coding sequence was cloned into the prokaryotic expression vector pBAD/gIII (Invitrogen). To simplify purification, the pBAD/gIII vector encodes a leader peptide which directs the recombinant protein into bacterial periplasmic space, thereby minimizing any potential toxic effect. The pBAD/gIII vector also encodes a C-terminal polyhistidine tag for detection with an anti-His antibody and for purification with ProBond resin (Invitrogen). The pBAD/gIII vector carrying the mEP17 coding sequence was transformed into *E. coli* according to the manufacturer's conditions. Transformed *E. coli* were cultured and recombinant protein was extracted. To confirm the production of mEP17 protein, protein derived from transformed *E. coli* was resolved on a polyacrylamide gel and Western blot analysis was performed according to standard techniques.

Example 13

In Vitro Binding Assays

Recombinant protein is obtained, for example, according to the approach described in Example 12 herein above. The protein is immobilized on chips appropriate for ligand binding assays. The protein immobilized on the chip is exposed to sample compound in solution according to methods well known in the art. While the sample compound is in contact with the immobilized protein, measurements capable of detecting protein-ligand interactions are conducted. Measurement techniques include, but are not limited to, SEDLI, biacore, and FCS, as described above. Compounds found to bind the protein are readily discovered in this approach and are subjected to further characterization.

Example 14

In Vivo Fertility Assay

Five wild type heterozygous transgenic and five mutant homozygous transgenic male mice are individually mated with five wild type C57BL/6 females during an overnight interval. Females exhibiting a vaginal plug the next morning are isolated. If pregnancy occurs, the genotype of the offspring are analyzed by PCR amplification of tail DNA using primers to detect the transgene. A lower percentage of pregnant females resulting from mating with homozygous mutant males suggests male subfertility.

Example 15

In Vitro Fertility Assay

The method used is essentially that of Wolf and Inoue (1976). In brief, male mice are killed, and each cauda epididymis is rapidly excised and minced in 1 ml of Toyoda's medium pre-equilibrated at 37° C. under 5% (vol/vol) carbon dioxide in air. The minced tissue is left at 37° C. for 30 minutes before the tissues pieces are removed. An aliquot is taken for sperm counting, and the incubation is continued for a further 30 minutes. Female mice are induced to superovulate by injections of PMSG and hCG. The female mice are killed, and their oviducts are removed and placed into Biggers, Whitten, and Whittingham medium (BWW). Under a microscope, the oviduct is pricked, and the cumulus mass is removed and treated with hyaluronidase. The denuded eggs are washed through three changes of medium before being allotted to 100 μl droplets of medium under silicon oil.

Approximately $10^5$ spermatozoa are added to each drop (i.e. $10^6$ sperm/ml), and the dishes are incubated at 37° C. under 5% (vol/vol) carbon dioxide in air for 5 hours. At this time, some eggs are removed and washed by repeated micropipetting before the number of attached spermatozoa is scored. The rest of the eggs are transferred to fresh medium and incubated for a further 24 hours, at which time eggs are scored for evidence of fertilization and development. Experiments are conducted with spermatozoa from a mutant and a wild type male and eggs from a common pool of females.

Example 16

Regulation of EP17 Protein

The regulation of mEP17 protein expression was investigated using Western blotting and immunohistochemistry in castrated mice, castrated testosterone supplemented mice, unilateral castrated mice, unilateral cryptorchid mice, and busulphan-treated mice. As previously observed at the mRNA level (FIGS. 15A-15C), mEP17 protein disappeared from the initial segment two days after bilateral castration and was not restored by testosterone treatment. Similarly, after unilateral castration, mEP17 protein disappeared from the castrated side, but not from the non-castrated side. These data suggest that mEP17 is not regulated by circulating androgens, but can be regulated by testicular factors provided via the efferent ducts.

To determine whether germ cell-associated testicular factors can regulate mEP17, spermatogenesis was disrupted using cryptorchidism or busulphan treatment. One month following cryptorchidism, mEP17 protein was not detected in the initial segment of the cryptorchid epididymis but was detected at normal levels in the scrotal epididymis. In cryptorchidism, the testis and the epididymis are exposed to abdominal temperature. To distinguish the effects of abdominal temperature on the testis or epididymis, spermatogenesis was also disrupted by busulphan treatment. Following a 35-day treatment, the level of mEP17 protein was drastically reduced when compared to untreated controls. Collectively, these observations suggest that mEP17 is regulated by germ cell-associated factors.

REFERENCES

The publications and other materials listed below and/or set forth in the text above to illuminate the background of the invention, and in particular cases, to provide-additional details respecting the practice, are incorporated herein by reference. Materials used herein include but are not limited to the following listed references.

Adelman et al., (1983) *DNA* 2:183-193.
Alam and Cook (1990) *Anal Biochem* 188:245-254.
Altschul et al. (1990) *J Mol Biol* 215:403-410.
Astraudo et al. (1995) *Arch Androl* 35:247-259.
Ausubel et al. (1992) "*Current Protocols in Molecular Biology*", John Wylie and Sons, Inc., New York.
Baird and Glasier (1999) *BMJ* 319:969-972.
Barber and Fayrer-Hosken (2000) *J Reprod Immunol* 46:103-124.
Barton (1998) *Acta Crystallogr D Biol Crystallogr* 54:1139-1146.
Batzer et al. (1991) *Nucleic Acid Res* 19:3619-3623.
Bodanszky, et al. (1976) "*Peptide Synthesis*", John Wiley and Sons, Second Edition, New York.
Brookes (1999) *Gene* 234(2):177-186.
Chomczynski and Sacchi (1987) *Anal Biochem* 162:156-159.
Conner et al. (1983) *Proc Natl Acad Sci USA* 80:278-282.
Cooper and Yeung (1999) *Hum Reprod Update* 5:141-152.
Costa et al. (1997) *Biol Reprod* 56:985-990.
Cornwall et al. (2001) in "*The Epididymis*", Plenum Press.
Cubitt et al. (1995) *Trends Biochem Sci* 20:448-455.
Diekman et al. (1999) *Immunol Rev* 171:203-211.
Feng et al. (1999) *J Reprod Med* 44:759-65.
Fidler and Bernstein (1999) *Public Health Reports* 114:494-511.
Glover, ed. (1985) "*DNA Cloning: A Practical Approach*", MRL Press, Ltd., Oxford, U.K.
Gorman et al. (1996) *Immunity* 5:241-252.
Hall et al. (2000) *Hum Gene Ther* 11(12):1705-1712.
Henikoff et al. (2000) *Electrophoresis* 21(9): 1700-1706.
Henikoff and Henikoff (1989) *Proc Natl Acad Sci USA* 89:10915.
Henikoff and Henikoff (2000) *Adv Protein Chem* 54:73-97.
Harlow and Lane (1988) "*Antibodies: A Laboratory Manual*" Cold Spring Harbor Laboratory Press, Cold Spring Harbor, N.Y.
Huang et al. (2000) *Pac Symp Biocomput* 230-241.
Hutchens and Yip (1993) *Rapid Commun Mass Spectrom* 7: 576-580.
Joyner (1993) "*Gene Targeting—A Practical Approach*" IRL Press, Oxford.
Kamischke and Nieschlag 1999 *Human Reproduction* 14(Suppl. 1): 1-23.
Karlin and Altschul (1993) *Proc Natl Acad Sci USA* 90:5873-87.
Kestila, M., et al. (1998) *Mol Cell* 1(4):575-82.
Krull et al. (1993) *Mol Reprod Dev* 34:16-34.
Kyte et al. (1982) *J. Mol. Biol.* 157:105.
Landgren et al. (1988) *Science* 241:1007.
Landgren et al. (1988) *Science* 242:229-237.
Lareyre, J. J., et al. (1999) *J. Biol. Chem.* 274:8282-8290
Lareyre et al. (2001) *Endocrinology* 142:1296-1308.
Li and Herskowitz (1993) *Science* 262:1870-1874.
Liedberg et al. (1983) *Sensors Actuators* 4:299-304.
Luckow and Schutz (1987) *Nucleic Acids Res* 15:5490.
Lufkin et al. (1993) *Proc Natl Acad Sci USA* 90:7225-7229.
Luo et al. (1996) *Biotechniques* 20(4):564-568.
Luyckx et al. (1999) *Proc Natl Acad Sci USA* 96(21):12174-12179.
Madge et al. (1972) *Phys Rev Lett* 29:705-708.
Maiti et al. (1997) *Proc Natl Acad Sci USA,* 94:11753-11757.
Malmquist (1993) *Nature* 361:186-187.
Mendelsohn et al. (1994) *Development* 120:2749-2771.
Nachtigal et al. (1989) *Nuc Acid Res* 17:4327-4337.
Naz (1999) *Immunol Rev* 171:193-202.
Needleman and Wunsch (1970) *J Mol Biol* 48:443-453.
Nikkanen et al. (2000) *Contraception* 61:401-406.
Ochman et al. (1990) in "*PCR protocols: a Guide to Methods and Applications*" Innis et al. eds., pp. 219-227, Academic Press, San Diego, Calif.
Ohtsuka et al. (1985) *J Biol Chem* 260:2605-2608.
Ong et al. (2000) *Biochim Biophys Acta* 1482:209-17.
Orita et al. (1989) *Proc Natl Acad Sci USA* 86(8):2766-70.
Palmiter and Brinster (1985) *Cell* 41:343-345.
Paterson et al. (2000) *Cells Tissues Organs* 166:228-32.
Pearson and Lipman (1988) *Proc Natl Acad Sci USA* 85: 2444-2448.
Postic et al. (1999) *J Biol Chem* 275(1):305-315.
Rose and Botstein (1983) *Meth Enzymol* 101:167-180.
Rossolini et al. (1994) *Mol Cell Probes* 8:91-98.
Saiki et al. (1985) Bio/Technology 3:1008-1012.
Sambrook et al. eds. (1989) "*Molecular Cloning: A Laboratory Manual*" Cold Spring Harbor Laboratory Press, Cold Spring Harbor, N.Y.
Sauer (1998) *Methods* 14(4):381-392.
Saqi et al. (1999) *Bioinformatics* 15:521-522.
Silhavy et al. (1984) "*Experiments with Gene Fusions*" Cold Spring Harbor Laboratory, Cold Spring Harbor, N.Y.
Singh et al. (1989) *Biotechniques* 7:252-261.
Smith and Waterman (1981) *Adv Appl Math* 2:482.
Sonnenberg-Riethmacher et al. (1996) *Genes Dev* 10:1184-1193.
Srivastav (2000) *J Reprod Fertil* 119:241-252.
Stoneking et al. (1991) *Am J Hum Genet.* 48(2):370-382.

Talwar (1999) *Immunol Rev* 171:173-192.
Tegtmeyer (1975) *J Virol* 15(3):613-618.
Tijssen (1993) in "*Laboratory Techniques in Biochemistry and Molecular Biology-Hybridization with Nucleic Acid Probes*", part 1 chapter 2, Elsevier, New York, N.Y.
Tobin et al. (1979) *Proc Natl Acad Sci USA* 76:4350-4354.
U.S. Pat. No. 4,196,265
U.S. Pat. No. 4,554,101
U.S. Pat. No. 4,736,866
U.S. Pat. No. 4,769,331
U.S. Pat. No. 5,162,215
U.S. Pat. No. 5,234,933
U.S. Pat. No. 5,260,203
U.S. Pat. No. 5,279,833
U.S. Pat. No. 5,286,634
U.S. Pat. No. 5,326,902
U.S. Pat. No. 5,399,346
U.S. Pat. No. 5,489,742
U.S. Pat. No. 5,550,316
U.S. Pat. No. 5,573,933
U.S. Pat. No. 5,614,396
U.S. Pat. No. 5,625,125
U.S. Pat. No. 5,641,484
U.S. Pat. No. 5,643,567
U.S. Pat. No. 5,646,008
U.S. Pat. No. 5,648,061
U.S. Pat. No. 5,651,964
U.S. Pat. No. 5,741,957
U.S. Pat. No. 5,834,228
U.S. Pat. No. 5,837,479
U.S. Pat. No. 5,872,011
U.S. Pat. No. 6,087,111
U.S. Pat. No. 6,096,318
U.S. Pat. No. 6,132,270
Vidal et al. (1996) *Proc Natl Acad Sci USA* 93(19):10315-20.
von Heiji (1986) *Nucleic Acid Res* 14:4683-4690.
Wang et al. (1998) *Science* 280(5366):1077-1082.
WO 93/25521
WO 97/47763
Wolbach (1925) *J Exp Med* 42:753-777.
Wolf and Inoue (1976) *J Exp Zool* 196:27-38.
Worrall et al. (1998) *Anal Biochem* 70:750-756.
Yeung et al. (1999) *Biol Reprod* 61:1062-1069.
Yuan et al. (1999) *Hum Mutat* 14(5):440-446.
Zimmer et al. (1993) "*Peptides*" pp. 393-394, ESCOM Science Publishers, B. V.

It will be understood that various details of the invention can be changed without departing from the scope of the invention. Furthermore, the foregoing description is for the purpose of illustration only, and not for the purpose of limitation—the invention being defined by the claims.

What is claimed is:

1. A chimeric gene comprising an isolated promoter operably linked to a heterologous nucleotide sequence, wherein the isolated promoter comprises a) the nucleotide sequence of SEQ ID NO:1; or b) a nucleic acid molecule comprising a nucleotide sequence at least 99% identical to SEQ ID NO:1.

2. The chimeric gene of claim 1, wherein the isolated promoter comprises a TATA box and at least one cis-acting regulatory sequence selected from the group consisting of a Sp-1 binding site, an AP-1 binding site, a retinoic acid receptor binding site, an androgen receptor binding site, a C-Ets binding site, a SRY binding site, an AP-4 binding site, a C/EBP binding site, and combinations thereof.

3. A vector comprising the chimeric gene of claim 1.

4. An isolated host cell comprising the chimeric gene of claim 1.

5. The host cell of claim 4, wherein the cell is selected from the group consisting of a bacterial cell, a hamster cell, a mouse cell, and a human cell.

* * * * *